US010982221B2

(12) United States Patent
Chen et al.

(10) Patent No.: US 10,982,221 B2
(45) Date of Patent: Apr. 20, 2021

(54) PLANT-DERIVED ANTIBODIES AND DERIVATIVES THAT REDUCE RISK OF ANTIBODY-DEPENDENT ENHANCEMENT (ADE) OF INFECTION

(71) Applicant: ARIZONA BOARD OF REGENTS ON BEHALF OF ARIZONA STATE UNIVERSITY, Scottsdale, AZ (US)

(72) Inventors: Qiang Chen, Chandler, AZ (US); Huafang Lai, Chandler, AZ (US); Jonathan Hurtado, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 424 days.

(21) Appl. No.: 15/113,755

(22) PCT Filed: Jan. 27, 2015

(86) PCT No.: PCT/US2015/013115

§ 371 (c)(1),
(2) Date: Jul. 22, 2016

(87) PCT Pub. No.: WO2015/113055

PCT Pub. Date: Jul. 30, 2015

(65) Prior Publication Data

US 2017/0275639 A1 Sep. 28, 2017

Related U.S. Application Data

(60) Provisional application No. 61/932,033, filed on Jan. 27, 2014.

(51) Int. Cl.

| | |
|---|---|
| ***C12N 15/82*** | (2006.01) |
| ***C07K 16/10*** | (2006.01) |
| *A61K 39/00* | (2006.01) |

(52) U.S. Cl.

CPC ...... *C12N 15/8258* (2013.01); *C07K 16/1081* (2013.01); *C12N 15/8205* (2013.01); *A61K 2039/505* (2013.01); *C07K 2317/13* (2013.01); *C07K 2317/35* (2013.01); *C07K 2317/41* (2013.01); *C07K 2317/622* (2013.01); *C07K 2317/76* (2013.01); *Y02A 50/30* (2018.01)

(58) Field of Classification Search

None

See application file for complete search history.

(56) References Cited

U.S. PATENT DOCUMENTS

| | | | | |
|---|---|---|---|---|
| 9,499,608 | B2 * | 11/2016 | Chen .................. | C07K 16/1081 |
| 2002/0076406 | A1 | 6/2002 | Leung | |
| 2004/0001825 | A1 | 1/2004 | Govindan et al. | |
| 2006/0057149 | A1 | 3/2006 | Johnson et al. | |
| 2008/0170994 | A1 | 7/2008 | Pardridge et al. | |
| 2009/0041763 | A1 | 2/2009 | Kwon | |
| 2009/0110632 | A1 | 4/2009 | Young et al. | |
| 2009/0130123 | A1 | 5/2009 | Fikrig et al. | |
| 2009/0258011 | A1 | 10/2009 | Diamond et al. | |
| 2010/0331192 | A1 | 12/2010 | Zha et al. | |
| 2012/0329994 | A1 * | 12/2012 | Chen .................. | C07K 16/1081 530/387.3 |

FOREIGN PATENT DOCUMENTS

| | | | | |
|---|---|---|---|---|
| EP | 0657538 | A2 * | 6/1995 | ............. C12N 15/82 |
| WO | 2009120922 | A2 | 10/2009 | |

OTHER PUBLICATIONS

Castilho et al. Rapid High Yield Production of Different Glycoforms of Ebola Virus Monoclonal Antibody, PLoSone, 2011; 6(10): e260401, pp. 1-10.*

Schreeder et al. "Cutting edge: FcR-like 6 is an MHC class II receptor", J. Immunol. 2010, 185(1):23-7; 2.*

Sokolowska, et al. Biochimica et Biophysica Acta, 2013; 1834: 1474-1483.*

Ko et al. (A.V. Karasev (ed.) Plant-produced Microbial Vaccines. Current Topics in Microbiology and Immunology 332© Springer-Verlag Berlin Heidelberg 2009; pp. 55-78.*

Castilho et al. Rapid High Yield Production of Different Glycoforms of Ebola Virus Monoclonal Antibody PLoS One. 2011, 6(10): e2604: pp. 1-10.*

Brodzik & Steplewski, Antibody and Its Therapeutic Activity,A.V. Karasev (ed.) Plant-produced Microbial Vaccines. Current Topics in Microbiology and Immunology 332, © Springer-Verlag Berlin Heidelberg 2009.*

Natsume et al. Fucose removal from complex-type oligosaccharide enhances the antibody-dependent cellular cytotoxicity of single-gene-encoded antibody comprising a single-chain antibody linked the antibody constant region. J. Immunolog. Met./ 2005; 306:93-103.*

Castilho et al. Rapid High Yield Production of Different Glycoforms of Ebola Virus Monoclonal Antibody, PLoSone, 2011; 6(10): e260401, pp. 1-10 (Year: 2011).*

Schreeder et al. "Cutting edge: FcR-like 6 is an MHC class II receptor", J. Immunol. 2010, 185(1):23-7; 2-(Year: 2010).*

Sokolowska, et al. Biochimica et Biophysica Acta, 2013; 1834: 1474-1483 (Year: 2013).*

Ko et al. (A.V. Karasev (ed.) Plant-produced Microbial Vaccines. Current Topics in Microbiology and Immunology 332© Springer-Verlag Berlin Heidelberg 2009; pp. 55-78 (Year: 2009).*

Balsitis, et al., "Lethal antibody enhancement of dengue disease in mice is prevented by Fc modification", PLoS Pathog 6(2), e1000790, 13 pages (2010).

(Continued)

*Primary Examiner* — Shanon A. Foley
*Assistant Examiner* — Myron G Hill
(74) *Attorney, Agent, or Firm* — Viksnins Harris Padys Malen LLP

(57) ABSTRACT

The present invention describes the plant-based production of a therapeutic anti-virus antibody.

16 Claims, 25 Drawing Sheets

Specification includes a Sequence Listing.

(56) References Cited

OTHER PUBLICATIONS

Bendandi, et al., "Rapid, high-yield production in plants of individualized idiotype vaccines for non-Hodgkin's lymphoma", Annals of Oncology 21, 2420-2427 (2010).
Boado, et al., "Engineering and expression of a chimeric transferrin receptor monoclonal antibody for blood-brain barrier delivery in the mouse", Biotechnology and Bioengineering 102(4), 1251-1258 (2009).
Boado, et al., "Humanization of anti-human insulin receptor antibody for drug targeting across the human blood-brain barrier", Biotechnol Bioeng 96, 381-391 (2007).
Bode, et al., "West Nile virus disease: a descriptive study of 228 patients hospitalized in a 4-county region of Colorado in 2003", Clinical Infectious Diseases 42, 1234-1240 (2006).
Bosch, et al., "N-glycosylation of plant-produced recombinant proteins", Current Pharmaceutical Design 19, 5503-5512 (2013).
Brown, et al., "Tight junction protein expression and barrier properties of immortalized mouse brain microvessel endothelial cells", Brain Research 1130, 17-30 (2007).
Castilho, et al., "In Planta Protein Sialylation through Overexpression of the Respective Mammalian Pathway", Journal of Biological Chemistry 285(21), 15923-15930 (2010).
Castilho, et al., "Rapid high yield production of different glycoforms of Ebola virus monoclonal antibody", PloS One 6(10), e26040, 10 pages (2011).
Chargelegue, et al., "A murine monoclonal antibody produced in transgenic plants with plantspecific glycans is not immunogenic in mice", Transgenic Research 9, 187-194 (2000).
Chen, et al., "Agroinfiltration as an Effective and Scalable Strategy of Gene Delivery for Production of Pharmaceutical Proteins", Adv Tech Biol Med 1(1), 1-12 (2013).
Chen, "Expression and manufacture of pharmaceutical proteins in genetically engineered horticultural plants", In: MouB, Scorza R, editors. Transgenic Horticultural Crops: Challenges and Opportunities—Essays by Experts. Boca Raton: Taylor & Francis pp. 83-124 (2011).
Chen, "Expression and purification of pharmaceutical proteins in plants", Biological Engineering Transactions 1(4), 291-321 (2008).
Chen, et al., "Geminiviral vectors based on bean yellow dwarf virus for production of vaccine antigens and monoclonal antibodies in plants", Human Vaccines 7, 331-338 (2011).
Chen, "Virus-like Particle Vaccines for Norovirus Gastroenteritis. In: Giese M, editor. Molecular Vaccines. Vienna: Springer", Molecular Vaccines vol. 1, DOI 10.1007/978-3-7091-1419-3_8, 153-181 (2013).
Chung, et al., "Antibodies against West Nile virus non-structural (NS)-1 protein prevent lethal infection through Fc gamma receptor-dependent and independent mechanisms", J. Virol. 80(3), 1340-1351 (2006).
Chung, et al., "Antibody recognition of cell surface-associated NS1 triggers Fc-gamma receptor-mediated phagocytosis and clearance of West Nile Virus-infected cells", J. Virol. 81(17), 9551-9555 (2007).
Coisne, et al., "Mouse syngenic in vitro blood-brain barrier model: a new tool to examine inflammatory events in cerebral endothelium", Lab Invest 85(6), 734-746 (2005).
Cox, et al., "Glycan optimization of a human monoclonal antibody in the aquatic plant Lemna minor", Nature Biotechnology 24, 1591-1597 (2006).
De Muynck, et al., "Production of antibodies in plants: status after twenty years", Plant Biotechnology Journal 8, 529-563 (2010).
Diamond, et al., "A genetic basis for human susceptibility to West Nile virus", Trends Microbiol 14(7), 287-289 (2006).
Diamond, et al., "B cells and antibody play critical roles in the immediate defense of disseminated infection by West Nile encephalitis virus", J. Virol. 77(4), 2578-2586 (2003).
Diamond, et al., "Innate and adaptive immune responses determine protection against disseminated infection by West Nile Encephalitis virus", Viral Immunology 16(3), 259-278 (2003).
Diamond, "Mechanisms of Evasion of the Type I Interferon Antiviral Response by Flaviviruses", Interferon Cytokine Res. 29(9), 521-530 (2009).
Diamond, et al., "Modulation of dengue virus infection in human cells by alpha, beta, and gamma interferons", J. Virol. 74(11), 4957-4966 (2000).
Diamond, "Progress on the development of therapeutics against West Nile virus", Antiviral Res. 83(3), 214-227 (2009).
Ebel et al., "Partial genetic characterization of West Nile Virus strains, New York State, 2000", Emerg. Inf. Dis. 7(4), 650-653 (2001).
Eldadah, et al., "Pathogenesis of West Nile Virus encepahlitis in mice and rats. II. Virus multiplication, evolution of immunofluorescence, and development of histological lesions in the brain", Am J Epidemiol 86(3), 776-790 (1967).
Engle, et al., "Antibody prophylaxis and therapy against West Nile Virus infection in wild type and immunodeficient mice", J Virol 77(24), 12941-12949 (2003).
Eriksson, et al., "MAb Contaminant removal with a multimodal anion exchanger", BioProcess International, 52-56 (2009).
Feige, et al., "An unfolded CH1 domain controls the assembly and secretion of IgG antibodies", Mol Cell 34, 569-579 (2009).
Fischer, et al., "Plant-based production of biopharmaceuticals", Current Opinion in Plant Biology 72, 152-158 (2004).
Fuchs, et al., "The lectin pathway of complement activation contributes to protection from West Nile virus infection", Virology 412, 101-109 (2011).
Furuta, et al., "T-705 (favipiravir) and related compounds: Novel broad spectrum inhibitors of RNA viral infections", Antiviral Res. 82, 95-102 (2009).
Giritch, et al., "Rapid high-yield expression of full-size IgG antibodies in plants coinfected with noncompeting viral rectors", Proceedings of the National Academy of Sciences of the United States of America 103(40), 14701-14706 (2006).
Glass, et al., "CCR5 deficiency increases risk of symptomatic West Nile virus infection", J. Exp. Med. 203, 35-40 (2006).
Gomord, et al., "Plant-specific glycosylation patterns in the context of therapeutic protein production", Plant Biotechnology Journal 8, 564-587 (2010).
Gomord, et al., "Production and glycosylation of plant-made pharmaceuticals: the antibodies as a challenge", Plant Biotechnol. J. 2, 83-100 (2004).
Halstead, et al., "Intrinsic antibody-dependent enhancement of microbial infection in macrophages: disease regulation by immune complexes", Lancet Infect Dis 10, 712-722 (2010).
He, et al., "A Novel System for Rapid and Cost-Effective Production of Detection and Diagnostic Reagents of West Nile Virus in Plants", Journal of Biomedicine and Biotechnology 2012, 1-10 (2012).
Hiatt, et al., "Production of antibodies in transgenic plants", Nature 342, 76-78 (1989).
Houde, et al., "Post-translational modifications differentially affect IgG1 conformation and receptor binding", Mol Cell Proteomics 9, 1716-1728 (2010).
Huang, et al., "A DNA replicon system for rapid high-level production of virus-like particles in plants", Biotechnology and Bioengineering 103, 706-714 (2009).
Huang, et al., "High-level rapid production of full-size monoclonal antibodies in plants by a single-vector DNA replicon system", Biotechnology and Bioengineering 106, 9-17 (2010).
Hubalek, et al., "West Nile fever—a reemerging mosquito-borne viral disease in Europe", Emerg. Inf. Dis. 5(5), 643-650 (1999).
Hudson, et al., "Engineered antibodies", Nat. Med. 9(1), 129-134 (2003).
Hudson, et al., "High avidity scFv multimer; diabodies and triabodies", Journal of Immunological Methods 231, 177-189 (1999).
Huisman, et al., "Vaccine-induced enhancement of viral infections", Vaccine 27, 505-512 (2009).
Jin, et al., "A plant derived human monoclonal antibody induces an anti-carbohydrate immune response in rabbits", Glycobiology 18(3), 235-241 (2008).

(56) References Cited

OTHER PUBLICATIONS

Jung, et al., "Bypassing glycosylation: engineering aglycosylated full-length IgG antibodies for human therapy", Curr Opin Biotechnol 22(6), 858-867 (2011).
Pierson, et al., "A rapid and quantitative assay for measuring antibody-mediated neutralization of West Nile virus infection", Virology 346, 53-65 (2006).
Pierson, et al., "An infectious West Nile Virus that expresses a GFP reporter gene", Virology 334, 28-40 (2005).
Pierson, et al., "The stoichiometry of antibody-mediated neutralization and enhancement of West Nile virus infection", Cell Host & Microbe 1(2), 135-145 (2007).
Raju, "Terminal sugars of Fc glycans influence antibody effector functions of IgGs", Curr. Opin. Immunol. 20, 471-478 (2008).
Roth, et al., "Protein N-glycosylation along the secretory pathway: relationship to organelle topography and function, protein quality control, and cell interactions", Chemical reviews 102, 285-303 (2002).
Royston, et al., "Glycosylation of Recombinant Antibody Therapeutics", Biotechnology Progress 21, 11-16 (2005).
Samuel, et al., "Axonal transport mediates West Nile virus entry into the central nervous system and induces acute flaccid paralysis", Proc. Natl. Acad. Sci. 104(43), 17140-17145 (2007).
Santi, et al., "An efficient plant viral expression system generating orally immunogenic Norwalk virus-like particles", Vaccine 26(15), 1846-1854 (2008).
Santi, et al., "Virus-like particles production in green plants", Methods 40, 66-76 (2006).
Schahs, et al., "Production of a monoclonal antibody in plants with a humanized N-glycosylation pattern", Plant Biotechnology Journal 5, 657-663 (2007).
Schreeder, et al., "Cutting edge: FcR-like 6 is an MHC class II receptor", The Journal of Immunology 185, 23-27 (2010).
Shields, et al., "Lack of fucose on human IgG1 N-linked oligosaccharide improves binding to human Fcgamma RIii and antibody-dependent cellular toxicity", J. Biol. Chem. 277(30), 26733-26740 (2002).
Sokolowska, et al., "Mass spectrometry investigation of glycosylation on the NXS/T sites in recombinant glycoproteins", Biochim Biophys Acta 1834(8), 1474-1483 (2013).
Stadlmann, et al., "Analysis of immunoglobulin glycosylation by LC-ESI-MS of glycopeptides and oligosaccharides", Proteomics 8, 2858-2871 (2008).
Stamatovic, et al., "Potential role of MCP-1 in endothelial cell tight junction 'opening': signaling via Rho and Rho kinase", Journal of Cell Science 116, 4615-4628 (2003).
Stanley, et al., "Monoclonal antibody cure and prophylaxis of lethal Sindbis virus encephalitis in mice", J. Virol. 58, 107-115 (1986).
Strasser, et al., "Generation of glyco-engineered Nicotiana benthamiana for the production of monoclonal antibodies with a homogeneous human-like N-glycan structure", Plant Biotechnology Journal 6, 392-402 (2008).
Strasser, et al., "Improved Virus Neutralization by Plant-produced Anti-HIV Antibodies with a Homogeneous Î$^2$1,4-Galactosylated N-Glycan Profile", Journal of Biological Chemistry 284, 20479-20485 (2009).
Thompson, et al., "A therapeutic antibody against west nile virus neutralizes infection by blocking fusion within endosomes", PLoS Pathog. 5(5), 1-10 (2009).
Villalobos, et al., "Gene Designer: a synthetic biology tool for constructing artificial DNA segments", BMC Bioinformatics 7, 285, 8 pages (2006).
Vitale, et al., "Recombinant pharmaceuticals from plants: the plant endomembrane system as bioreactor", Mol. Interv. 5(4), 216-225 (2005).
Wan, et al., "Production and characterization of a CD25-specific scFv-Fc antibody secreted from Pichia pastoris", Applied Microbiology and Biotechnology 97, 3855-3863 (2013).
Wang, et al., "Mining a yeast library for brain endothelial cell-binding antibodies", Nat. Meth. 4(2), 143-145 (2007).
Wang, et al., "Structural and functional characterization of glycosylation in an immunoglobulin G1 to Cryptococcus neoformans glucuronoxylomannan", Mol. Immunol. 43, 987-998 (2006).
Wang, et al., "Toll-like receptor 3 mediates West Nile virus entry into the brain causing lethal encephalitis", Nat. Med. 10(12), 1366-1373 (2004).
Weiner, et al., "Immunology and immunotherapy of Alzheimer's disease", Nat. Rev. Immunol. 6, 404-416 (2006).
Weintraub, et al., "Clinical trial of a plant-derived antibody on recolonization of mutans streptococci", Caries Research 39, 241-250 (2005).
Wilke et al., "Primary Production of Biopharmaceuticals in Plants—an Economically Attractive Choice?", European Biopharmaceutical Review (Autumn 2003 Issue), 4 pages (2003).
Williams, et al., "Therapeutic efficacy of antibodies lacking FcγR against lethal dengue virus infection is due to neutralizing potency and blocking of enhancing antibodies", PLoS Pathog, 9(2), e1003157, 17 pages (2013).
Wu, et al., "Simultaneous targeting of multiple disease mediators by a dual-variable-domain immunoglobulin", Nat. Biotech. 25, 1290-1297 (2007).
Zeitlin, et al., "A humanized monoclonal antibody produced in transgenic plants for immunoprotection of the vagina against genital herpes", Nat. Biotech. 16(13), 1361-1364 (1998).
Zeitlin, et al., "Enhanced potency of a fucose-free monoclonal antibody being developed as an Ebola virus immunoprotectant", Proceedings of the National Academy of Sciences 108(51), 20690-20694 (2011).
Zhang, et al., "Delivery of beta-galactosidase to mouse brain via the blood-brain barrier transferrin receptor", J. Pharmacol. Exp. Ther. 313(3), 1075-1081 (2005).
Zhang, et al., "Preparation and characterization of the monoclonal antibodies against Japanese encephalitis virus", Acta Virologica 36, 533-540 (1992).
Zhou, et al., "Development of a simple and rapid method for producing nonfucosylated oligomannose containing antibodies with increased effector function", Biotechnology and Bioengineering 99, 652-665 (2008).
Kaiser, "Is the Drought Over for Pharming", Science 320, 473-475 (2008).
Kaneko, et al., "Anti-Inflammatory Activity of Immunoglobulin G Resulting from Fc Sialylation", Science 313, 670-673 (2006).
Ko, et al., "Function and glycosylation of plant-derived antiviral monoclonal antibody", Proc. Natl. Acad. Sci. USA. 100(13), 8013-8018 (2003).
Ko, et al., "Plant biopharming of monoclonal antibodies", Virus Research 111, 93-100 (2005).
Kurane, et al., "Lysis of dengue virus-infected cells by natural cell-mediated cytotoxicity and antibody-dependent cell-mediated cytotoxicity", J. Virol. 52, 223-230 (1984).
Lai, et al., "Bioprocessing of plant-derived virus-like particles of Norwalk virus capsid protein under current Good Manufacture Practice regulations", Plant Cell Reports 31(3), 573-584 (2012).
Lai, et al., "Monoclonal antibody produced in plants efficiently treats West Nile virus infection in mice", Proceedings of the National Academy of Sciences of the United States of America 107(6), 2419-2424 (2010).
Lai, et al., "Robust production of virus-like particles and monoclonal antibodies with geminiviral replicon vectors in lettuce", Plant Biotechnology Journal 10, 95-104 (2012).
Lanciotti, et al., "Rapid detection of west nile virus from human clinical specimens, field-collected mosquitoes, and avian samples by a TaqMan reverse transcriptase—PCR assay", J. Clin. Microbiol. 38(11), 4066-4071 (2000).
Laoprasopwattana, et al., "Antibody-dependent cellular cytotoxicity mediated by plasma obtained before secondary dengue virus infections: potential involvement in early control of viral replication", J. Infect. Dis. 195, 1108-1116 (2007).
Lee, et al., "BiP and immunoglobulin light chain cooperate to control the folding of heavy chain and ensure the fidelity of immunoglobulin assembly", Mol Biol Cell 10, 2209-2219 (1999).

(56) References Cited

OTHER PUBLICATIONS

Lee, et al., "Targeting Rat Anti-Mouse Transferrin Receptor Monoclonal Antibodies through Blood-Brain Barrier in Mouse", Journal of Pharmacology and Experimental Therapeutics 292(3), 1048-1052 (2000).
Leuzinger, et al., "Efficient Agroinfiltration of Plants for High-level Transient Expression of Recombinant Proteins", Journal of Visualized Experiments 77, e50521, 9 pages (2013).
Li, et al., "Genetically engineered brain drug delivery vectors: cloning, expression and in vivo application of an anti-transferrin receptor single chain antibody-streptavidin fusion gene and protein", Protein Eng. 12(9), 787-796 (1999).
Lico, et al., "Viral vectors for production of recombinant proteins in plants", Journal of Cellular Physiology 216, 366-377 (2008).
Lim, et al., "Genetic Deficiency of Chemokine Receptor CCR5 is a Strong Risk Factor for Symptomatic West Nile Virus Infection: A Meta-Analysis of 4 Cohorts in the US Epidemic", Journal of Infectious Diseases 197, 262-265 (2008).
Lim, et al., "Genetic variation in OAS 1 is a risk factor for initial infection with West Nile virus in man", PLoS Pathog. 5(2), 1-12 (2009).
Loos, et al., "Expression of antibody fragments with a controlled N-glycosylation pattern and induction of endoplasmic reticulum-derived vesicles in seeds of *Arabidopsis*", Plant Physiol 155, 2036-2048 (2011).
Loos, et al., "IgG-Fc glycoengineering in non-mammalian expression hosts", Arch Biochem Biophys 526, 167-173 (2012).
Lue, et al., "Modeling Alzheimer's disease immune therapy mechanisms: Interactions of human postmortem microglia with antibody-opsonized amyloid beta peptide", Journal of Neuroscience Research 70, 599-610 (2002).
Ma, et al., "Characterization of a recombinant plant monoclonal secretory antibody and preventive immunotherapy in humans", Nat. Med. 4(5), 601-606 (1998).
Ma, et al., "The production of recombinant pharmaceutical proteins in plants", Nature Reviews Genetics 4, 794-805 (2003).
Marillonnet, et al., "In planta engineering of viral RNA replicons: efficient assembly by recombination of DNA modules delivered by Agrobacterium", Proc. Natl. Acad. Sci. 101(18), 6852-6857 (2004).
McCormick, et al., "Plant-produced idiotype vaccines for the treatment of non-Hodgkin's lymphoma: Safety and immunogenicity in a phase I clinical study", Proc. Natl. Acad. Sci. USA. 105(29), 10131-10136 (2008).
McGrath, et al., "Bifunctional fusion between nerve growth factor and a transferrin receptor antibody", Journal of Neuroscience Research 47, 123-133 (1997).
McLean, et al., "A Human AntiPseudomonas aeruginosa Serotype 06ad Immunoglobulin GI Expressed in Transgenic Tobacco Is Capable of Recruiting Immune System Effector Function In vitro", Antimicrob. Agents Chemother. 51(9), 3322-3328 (2007).
Meguro, et al., "Antibody-dependent cell-mediated cytotoxicity against cells infected with respiratory syncytial virus: characterization of in vitro and in vivo properties", J. Immunol. 122(6), 2521-2526 (1979).
Mehlhop, et al., "C1q Inhibits Antibody-Dependent Enhancement of Flavivirus infection In Vitro and In Vivo in an IgG Subclass Specific Manner", Cell Host Microbe 2(6), 417-426 (2007).
Mehlhop, et al., "C1q reduces the stoichiometric threshold for antibody-mediated neutralization of West Nile virus", Cell Host Microbe. 6(4), 381-391 (2009).
Mehlhop, et al., "Complement activation is required for the induction of a protective antibody response against West Nile virus infection", J. Virol. 79(12), 7466-7477 (2005).
Melnick et al., "Isolation from human sera in Egypt of a virus apparently identical to West Nile virus", Proc. Soc. Exp. Biol. Med. 77, 661-665 (1951).
Morens, "Antibody-dependent of enhancement of infection and the pathogenesis of viral disease", Clin Inf Dis 19, 500-512 (1994).
Morrey, et al., "Defining limits of treatment with humanized neutralizing monoclonal antibody for West Nile virus neurological infection in a hamster model", Antimicrobial Agents and Chemotherapy 51(7): 2396-2402 (2007).
Morrey, et al., "Efficacy of orally administered T-705 pyrazine analog on lethal West Nile virus infection in rodents", Antiviral Res. 80(3), 377-379 (2008).
Morrey, et al., "Humanized monoclonal antibody against West Nile virus envelope protein administered after neuronal infection protects against lethal encephalitis in hamsters", J. Infect. Dis. 194(9), 1300-1308 (2006).
Morrey, et al., "West Nile virus-induced acute flaccid paralysis is prevented by monoclonal antibody treatment when administered after infection of spinal cord neurons", J. Neurovirol. 14(2), 152-163 (2008).
Nakagawa, et al., "A new blood-brain barrier model using primary rat brain endothelial cells, pericytes and astrocytes", Neurochemistry International 54, 253-263 (2009).
Natsume, et al., "Fucose Removal from Complex-Type Oligosaccharide Enhances the Antibody-Dependent Cellular Cytotoxicity of Single-Gene-Encoded Bispecific Antibody Comprising of Two Single-Chain Antibodies Linked to the Antibody Constant Region", J. Biochem. 140, 359-368 (2006).
Nimmerjahn, et al., "Fcgamma receptors as regulators of immune responses", Nat. Rev. Immunol. 8, 34-47 (2008).
Nuttall, et al., "ER-resident chaperone interactions with recombinant antibodies in transgenic plants", Eur. J. Biochem. 269, 6042-6051 (2002).
Oliphant, et al., "Development of a humanized monoclonal antibody with therapeutic potential against West Nile vius", Nature Medicine 11(5), 522-530 (2005).
Oliphant, et al., "Induction of epitope-specific neutralizing antibodies against West Nile virus", Journal of Virology 81(21), 11828-11839 (2007).
Pardridge, et al., "Comparison of in vitro and in vivo models of drug transcytosis through the blood-brain barrier", J. Pharmacol. Exp. Ther. 253(2), 884-891 (1990).
Patent Cooperation Treaty, International Search Report and Written Opinion for PCT/US2012/41121, 15 pages, dated Oct. 16, 2012.
Patent Cooperation Treaty, International Search Report and Written Opinion for PCT/US2011/20635, 10 pages, dated Apr. 22, 2011.
Patent Cooperation Treaty, International Search Report and Written Opinion for PCT/US2015/13115, 18 pages, dated Aug. 5, 2015.
Petersen, et al., "The mannan-binding lectin pathway of complement activation: biology and disease association", Mol. Immunol. 38, 133-149 (2001).
Petersen, et al., "West Nile virus: review of the literature", Jama 310(3), 308-315 (2013).
Phoolcharoen, et al., "A nonreplicating subunit vaccine protects mice against lethal Ebola virus challenge", Proceedings of the National Academy of Sciences 108(51), 20695-20700 (2011).
Phoolcharoen, et al., "Expression of an immunogenic Ebola immune complex in Nicotiana benthamiana", Plant Biotechnology Journal 9, 807-816 (2011).
Genbank , Accession No. KC254888.1, 1 page (Mar. 12, 2013).
Genbank , Accession No. KC254889.1, 1 page (Mar. 12, 2013).

* cited by examiner

Figure 1. Structure and name of N-glycosylation that are covered in this claim. The structure of one isomer is shown for glycans that have multiple physiological isomers.

| | A | B | C | D | E | F | G |
|---|---|---|---|---|---|---|---|
| Glycan Structure | pHu-E16 | pHu-E16scFv-$C_H^{1-3}$ | pHu-E16scFv-$C_H^{1-3}$/ LC | HC/ pHu-E16scFv-$C_L$ | pHu-E16scFv-$C_H^{1-3}$/ pHu-E16 scFv-$C_L$ | mHu-E16 | mHu-E16scFv-$C_H^{1-3}$ |
| GnGnXF | 90 | | 27 | 88 | 19 | | |
| ∑ oligoman | | 90 | 66 | 8 | 72 | | 10 |
| GnGnF6 | | | | | | 78 | 65 |
| AGnF$^6$ | | | | | | 15 | 20 |
| ∑ other | 10 | 10 | 7 | | 9 | 8 | 5 |

Figure 16. . Relative abundance in percentage of major glyco-structures detected on Hu-E16 variants.

∑other complex: sum of glycoforms present at levels below 5 %. The glycan structures are assigned using the ProGlycAn nomenclature (www.proglycan.com). HC: heavy chain, $C_H^{1-3}$: the constant regions 1-3 of HC, LC: light chain, $C_L$: Constant region of LC.

FIGURE 17-1

E60 WT Heavy Chain

*Nucleic Acid Sequence* gaattcacaatgggatggtcttgtatcatcctttttcttggttgcaacagctactggtgttcattctgaggtccaggtgcaacagtctggacctgaactggt
gacgcctggggcctcagtgaagatatcctgcaagacttctggatacactttcactgaatataccgtccactgggtgaagcagagccatggaaagagcc
ttgagtggattggaggcattaatcctaccagtggtggtactaactacaaccagaggttcaggggcaaggccacattgactgtagacaggtcctccagc
acagcctacatggagctccgcagcctgacatctgaggattctgcagtctatttttgtgcaggaaccctctatggctacccttttgacttctggggccaag
gcaccactctcacagtctcctcagctagcaccaagggaccttctgtttttccacttgctccttcttctaagtctacttctggtggaactgctgctttgggttg
tttggtgaaagattactttcctgagccagtgaccgtttcttggaactcaggtgctcttacatctggtgttcatactttcccagctgttcttcaatcttcagga
ctttactcactttcttctgttgttaccgttccttcttcaagcttgggcactcagacctacatctgcaatgtgaatcacaaacccagcaacaccaaggttgac
aagaaagttgagcccaagtcttgtgacaagactcatacgtgtccaccgtgcccagcacctgaacttcttggaggaccgtcagtcttcttgtttcctccaa
agcctaaggataccttgatgatctccaggactcctgaagtcacatgtgtagttgtggatgtgagccatgaagatcctgaggtgaagttcaactggtatg
tggatggtgtggaagtgcacaatgccaagacaaagccgagagaggaacagtacaacagcacgtacagggttgtctcagttctcactgttctccatca
agattggttgaatggcaaagagtacaagtgcaaggtctccaacaaagccctcccagcccccattgagaagaccatttccaaagcgaaagggcaacc
ccgtgaaccacaagtgtacacacttcctccatctcgcgatgaactgaccaagaaccaggtcagcttgacttgcctggtgaaaggcttctatccctctga
catagctgtagagtgggagagcaatgggcaaccggagaacaactacaagactacacctcccgttctcgattctgacggctccttcttcctctacagca
agctcacagtggacaagagcaggtggcaacaagggaatgtcttctcatgctccgtgatgcatgaggctcttcacaatcactacacacagaagagtctc
tccttgtctccgggtaaatgaggatcc (SEQ ID NO:17)

*Amino Acid Sequence*

MGWSCIILFLVATATGVHSEVQVQQSGPELVTPGASVKISCKTSGYTFTEYTVHWVKQSHGKSLEWIGGINPTSGGT
NYNQRFRGKATLTVDRSSSTAYMELRSLTSEDSAVYFCAGTLYGYPFDFWGQGTTLTVSSASTKGPSVFPLAPSSKS
TSGGTAALGCLVKDYFPEPVTVSWNSGALTSGVHTFPAVLQSSGLYSLSSVVTVPSSSLGTQTYICNVNHKPSNTKV
DKKVEPKSCDKTHTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSVMHEALHNHYTQKSLS
LSPGK (SEQ ID NO:18)

E60 Heavy Chain NQ mutant

*Nucleic Acid Sequence*

Gaattcacaatgggatggtcttgtatcatcctttttcttggttgcaacagctactggtgttcattctgaggtccaggtgcaacagtctggacctgaactggt
gacgcctggggcctcagtgaagatatcctgcaagacttctggatacactttcactgaatataccgtccactgggtgaagcagagccatggaaagagcc
ttgagtggattggaggcattaatcctaccagtggtggtactaactacaaccagaggttcaggggcaaggccacattgactgtagacaggtcctccagc
acagcctacatggagctccgcagcctgacatctgaggattctgcagtctatttttgtgcaggaaccctctatggctacccttttgacttctggggccaag
gcaccactctcacagtctcctcagctagcaccaagggaccttctgtttttccacttgctccttcttctaagtctacttctggtggaactgctgctttgggttg
tttggtgaaagattactttcctgagccagtgaccgtttcttggaactcaggtgctcttacatctggtgttcatactttcccagctgttcttcaatcttcagga
ctttactcactttcttctgttgttaccgttccttcttcaagcttgggcactcagacctacatctgcaatgtgaatcacaaacccagcaacaccaaggttgac

FIGURE 17-2 aagaaagttgagcccaagtcttgtgacaagactcatacgtgtccaccgtgcccagcacctgaacttcttggaggaccgtcagtcttcttgtttcctccaa
agcctaaggataccttgatgatctccaggactcctgaagtcacatgtgtagttgtggatgtgagccatgaagatcctgaggtgaagttcaactggtatg
tggatggtgtggaagtgcacaatgccaagacaaagccgagagaggaacagtaccaaagcacgtacagggttgtctcagttctcactgttctccatca
agattggttgaatggcaaagagtacaagtgcaaggtctccaacaaagccctcccagcccccattgagaagaccatttccaaagcgaaagggcaacc
ccgtgaaccacaagtgtacacacttcctccatctcgcgatgaactgaccaagaaccaggtcagcttgacttgcctggtgaaaggcttctatccctctga
catagctgtagagtgggagagcaatgggcaaccggagaacaactacaagactacacctcccgttctcgattctgacggctccttcttcctctacagca
agctcacagtggacaagagcaggtggcaacaagggaatgtcttctcatgctccgtgatgcatgaggctcttcacaatcactacacacagaagagtctc
tccttgtctccgggtaaatgaggatcc (SEQ ID NO:19)

*Amino Acid Sequence*

MGWSCIILFLVATATGVHSEVQVQQSGPELVTPGASVKISCKTSGYTFTEYTVHWVKQSHGKSLEWIGGINPTSGGT
NYNQRFRGKATLTVDRSSSTAYMELRSLTSEDSAVYFCAGTLYGYPFDFWGQGTTLTVSSASTKGPSVFPLAPSSKS
TSGGTAALGCLVKDYFPEPVTVSWNSGALTSGVHTFPAVLQSSGLYSLSSVVTVPSSSLGTQTYICNVNHKPSNTKV
DKKVEPKSCDKTHTCPPCPAPELLGGPSVFLFPPKPKDTLMISRTPEVTCVVVDVSHEDPEVKFNWYVDGVEVHNAK
TKPREEQYQSTYRVVSVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSVMHEALHNHYTQKSLS
LSPGK (SEQ ID NO:20)

E60 Heavy Chain LALA mutant

*Nucleic Acid Sequence* gaattcacaatgggatggtcttgtatcatcctttttcttggttgcaacagctactggtgttcattctgaggtccaggtgcaacagtctggacctgaactggt
gacgcctggggcctcagtgaagatatcctgcaagacttctggatacactttcactgaatataccgtccactgggtgaagcagagccatggaaagagcc
ttgagtggattggaggcattaatcctaccagtggtggtactaactacaaccagaggttcaggggcaaggccacattgactgtagacaggtcctccagc
acagcctacatggagctccgcagcctgacatctgaggattctgcagtctatttttgtgcaggaaccctctatggctacccttttgacttctggggccaag
gcaccactctcacagtctcctcagctagcaccaagggaccttctgtttttccacttgctccttcttctaagtctacttctggtggaactgctgctttgggttg
tttggtgaaagattactttcctgagccagtgaccgtttcttggaactcaggtgctcttacatctggtgttcatactttcccagctgttcttcaatcttcagga
ctttactcactttcttctgttgttaccgttccttcttcaagcttgggcactcagacctacatctgcaatgtgaatcacaaacccagcaacaccaaggttgac
aagaaagttgagcccaagtcttgtgacaagactcatacgtgtccaccgtgcccagcacctgaaGCtGCtggaggaccgtcagtcttcttgtttcctcc
aaagcctaaggataccttgatgatctccaggactcctgaagtcacatgtgtagttgtggatgtgagccatgaagatcctgaggtgaagttcaactggta
tgtggatggtgtggaagtgcacaatgccaagacaaagccgagagaggaacagtacaacagcacgtacagggttgtctcagttctcactgttctccatc
aagattggttgaatggcaaagagtacaagtgcaaggtctccaacaaagccctcccagcccccattgagaagaccatttccaaagcgaaagggcaac
cccgtgaaccacaagtgtacacacttcctccatctcgcgatgaactgaccaagaaccaggtcagcttgacttgcctggtgaaaggcttctatccctctg
acatagctgtagagtgggagagcaatgggcaaccggagaacaactacaagactacacctcccgttctcgattctgacggctccttcttcctctacagc
aagctcacagtggacaagagcaggtggcaacaagggaatgtcttctcatgctccgtgatgcatgaggctcttcacaatcactacacacagaagagtct
ctccttgtctccgggtaaatgaggatcc (SEQ ID NO:21)

*Amino Acid Sequence*

MGWSCIILFLVATATGVHSEVQVQQSGPELVTPGASVKISCKTSGYTFTEYTVHWVKQSHGKSLEWIGGINPTSGGT
NYNQRFRGKATLTVDRSSSTAYMELRSLTSEDSAVYFCAGTLYGYPFDFWGQGTTLTVSSASTKGPSVFPLAPSSKS
TSGGTAALGCLVKDYFPEPVTVSWNSGALTSGVHTFPAVLQSSGLYSLSSVVTVPSSSLGTQTYICNVNHKPSNTKV

FIGURE 17-3

DKRVEPKSCDKTHTCPPCPAPEAAGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSVMHEALHNHYTQKSLS
LSPGK (SEQ ID NO:22)

E60 Heavy Chain LALAGA mutant

*Nucleic Acid Sequence* gaattcacaatgggatggtcttgtatcatcctttttcttggttgcaacagctactggtgttcattctgaggtccaggtgcaacagtctggacctgaactggt
gacgcctggggcctcagtgaagatatcctgcaagacttctggatacactttcactgaatataccgtccactgggtgaagcagagccatggaaagagcc
ttgagtggattggaggcattaatcctaccagtggtggtactaactacaaccagaggttcaggggcaaggccacattgactgtagacaggtcctccagc
acagcctacatggagctccgcagcctgacatctgaggattctgcagtctatttttgtgcaggaaccctctatggctacccttttgacttctggggccaag
gcaccactctcacagtctcctcagctagcaccaagggaccttctgtttttccacttgctccttcttctaagtctacttctggtggaactgctgctttgggttg
tttggtgaaagattactttcctgagccagtgaccgtttcttggaactcaggtgctcttacatctggtgttcatactttcccagctgttcttcaatcttcagga
ctttactcactttcttctgttgttaccgttccttcttcaagcttgggcactcagacctacatctgcaatgtgaatcacaaacccagcaacaccaaggttgac
aagaaagttgagcccaagtcttgtgacaagactcatacgtgtccaccgtgcccagcacctgaaGCtGCtggagCaccgtcagtcttcttgtttcctcc
aaagcctaaggataccttgatgatctccaggactcctgaagtcacatgtgtagttgtggatgtgagccatgaagatcctgaggtgaagttcaactggta
tgtggatggtgtggaagtgcacaatgccaagacaaagccgagagaggaacagtacaacagcacgtacagggttgtctcagttctcactgttctccatc
aagattggttgaatggcaaagagtacaagtgcaaggtctccaacaaagccctcccagcccccattgagaagaccatttccaaagcgaaagggcaac
cccgtgaaccacaagtgtacacacttcctccatctcgcgatgaactgaccaagaaccaggtcagcttgacttgcctggtgaaaggcttctatccctctg
acatagctgtagagtgggagagcaatgggcaaccggagaacaactacaagactacacctcccgttctcgattctgacggctccttcttcctctacagc
aagctcacagtggacaagagcaggtggcaacaagggaatgtcttctcatgctccgtgatgcatgaggctcttcacaatcactacacacagaagagtct
ctccttgtctccgggtaaatgaggatcc (SEQ ID NO:23)

*Amino Acid Sequence*

MGWSCIILFLVATATGVHSEVQVQQSGPELVTPGASVKISCKTSGYTFTEYTVHWVKQSHGKSLEWIGGINPTSGGT
NYNQRFRGKATLTVDRSSSTAYMELRSLTSEDSAVYFCAGTLYGYPFDFWGQGTTLTVSSASTKGPSVFPLAPSSKS
TSGGTAALGCLVKDYFPEPVTVSWNSGALTSGVHTFPAVLQSSGLYSLSSVVTVPSSSLGTQTYICNVNHKPSNTKV
DKKVEPKSCDKTHTCPPCPAPEAAGAPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSVMHEALHNHYTQKSLS
LSPGK (SEQ ID NO:24)

E60 scFv WT

*Nucleic Acid Sequence*

Gaattcacaatgggatggtcttgtatcatcctttttcttggttgcaacagctactggtgttcattctgaggtccaggtgcaacagtctggacctgaactggt
gacgcctggggcctcagtgaagatatcctgcaagacttctggatacactttcactgaatataccgtccactgggtgaagcagagccatggaaagagcc
ttgagtggattggaggcattaatcctaccagtggtggtactaactacaaccagaggttcaggggcaaggccacattgactgtagacaggtcctccagc
acagcctacatggagctccgcagcctgacatctgaggattctgcagtctatttttgtgcaggaaccctctatggctacccttttgacttctggggccaag

Figure 17-4:
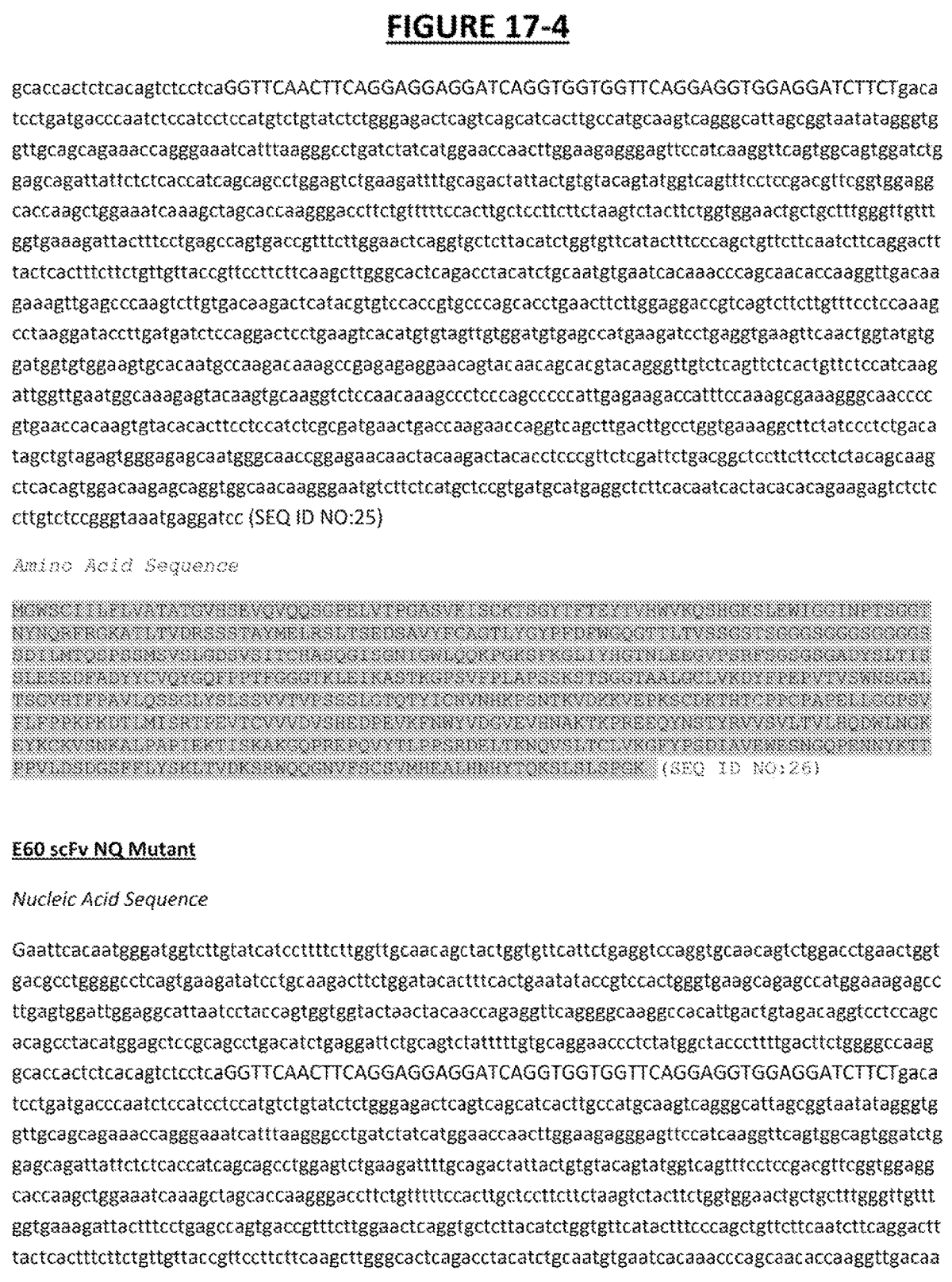

FIGURE 17-4 gcaccactctcacagtctcctcaGGTTCAACTTCAGGAGGAGGATCAGGTGGTGGTTCAGGAGGTGGAGGATCTTCTgaca
tcctgatgacccaatctccatcctccatgtctgtatctctgggagactcagtcagcatcacttgccatgcaagtcagggcattagcggtaatatagggtg
gttgcagcagaaaccagggaaatcatttaagggcctgatctatcatggaaccaacttggaagagggagttccatcaaggttcagtggcagtggatctg
gagcagattattctctcaccatcagcagcctggagtctgaagattttgcagactattactgtgtacagtatggtcagtttcctccgacgttcggtggagg
caccaagctggaaatcaaagctagcaccaagggacccttctgtttttccacttgctccttcttctaagtctacttctggtggaactgctgctttgggttgttt
ggtgaaagattactttcctgagccagtgaccgtttcttggaactcaggtgctcttacatctggtgttcatactttcccagctgttcttcaatcttcaggactt
tactcactttcttctgttgttaccgttccttcttcaagcttgggcactcagacctacatctgcaatgtgaatcacaaacccagcaacaccaaggttgacaa
gaaagttgagcccaagtcttgtgacaagactcatacgtgtccaccgtgcccagcacctgaacttcttggaggaccgtcagtcttcttgtttcctccaaag
cctaaggataccttgatgatctccaggactcctgaagtcacatgtgtagttgtggatgtgagccatgaagatcctgaggtgaagttcaactggtatgtg
gatggtgtggaagtgcacaatgccaagacaaagccgagagaggaacagtacaacagcacgtacagggttgtctcagttctcactgttctccatcaag
attggttgaatggcaaagagtacaagtgcaaggtctccaacaaagccctcccagcccccattgagaagaccatttccaaagcgaaagggcaacccc
gtgaaccacaagtgtacacacttcctccatctcgcgatgaactgaccaagaaccaggtcagcttgacttgcctggtgaaaggcttctatccctctgaca
tagctgtagagtgggagagcaatgggcaaccggagaacaactacaagactacacctcccgttctcgattctgacggctccttcttcctctacagcaag
ctcacagtggacaagagcaggtggcaacaagggaatgtcttctcatgctccgtgatgcatgaggctcttcacaatcactacacacagaagagtctctc
cttgtctccgggtaaatgaggatcc (SEQ ID NO:25)

*Amino Acid Sequence*

MGWSCIILFLVATATGVHSEVQVQQSGPELVTPGASVKISCKTSGYTFTEYTVHWVKQSHGKSLEWIGGINPTSGG
NYNQRFRGKATLTVDRSSSTAYMELRSLTSEDSAVYFCAGTLYGYPFDFWGQGTTLTVSSGSTSGGGSGGGSGGGS
SDILMTQSPSSMSVSLGDSVSITCHASQGISGNIGWLQQKPGKSFKGLIYHGTNLEDGVPSRFSGSGSGADYSLTIS
SLESEDFADYYCVQYGQFPPTFGGGTKLEIKASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK (SEQ ID NO:26)

E60 scFv NQ Mutant

*Nucleic Acid Sequence*

Gaattcacaatgggatggtcttgtatcatccttttcttggttgcaacagctactggtgttcattctgaggtccaggtgcaacagtctggacctgaactggt
gacgcctggggcctcagtgaagatatcctgcaagacttctggatacactttcactgaatataccgtccactgggtgaagcagagccatggaaagagcc
ttgagtggattggaggcattaatcctaccagtggtggtactaactacaaccagaggttcaggggcaaggccacattgactgtagacaggtcctccagc
acagcctacatggagctccgcagcctgacatctgaggattctgcagtctatttttgtgcaggaaccctctatggctacccttttgacttctggggccaag
gcaccactctcacagtctcctcaGGTTCAACTTCAGGAGGAGGATCAGGTGGTGGTTCAGGAGGTGGAGGATCTTCTgaca
tcctgatgacccaatctccatcctccatgtctgtatctctgggagactcagtcagcatcacttgccatgcaagtcagggcattagcggtaatatagggtg
gttgcagcagaaaccagggaaatcatttaagggcctgatctatcatggaaccaacttggaagagggagttccatcaaggttcagtggcagtggatctg
gagcagattattctctcaccatcagcagcctggagtctgaagattttgcagactattactgtgtacagtatggtcagtttcctccgacgttcggtggagg
caccaagctggaaatcaaagctagcaccaagggacccttctgtttttccacttgctccttcttctaagtctacttctggtggaactgctgctttgggttgttt
ggtgaaagattactttcctgagccagtgaccgtttcttggaactcaggtgctcttacatctggtgttcatactttcccagctgttcttcaatcttcaggactt
tactcactttcttctgttgttaccgttccttcttcaagcttgggcactcagacctacatctgcaatgtgaatcacaaacccagcaacaccaaggttgacaa

FIGURE 17-5 gaaagttgagcccaagtcttgtgacaagactcatacgtgtccaccgtgcccagcacctgaacttcttggaggaccgtcagtcttcttgtttcctccaaag
cctaaggataccttgatgatctccaggactcctgaagtcacatgtgtagttgtggatgtgagccatgaagatcctgaggtgaagttcaactggtatgtg
gatggtgtggaagtgcacaatgccaagacaaagccgagagaggaacagtaccaaagcacgtacagggttgtctcagttctcactgttctccatcaag
attggttgaatggcaaagagtacaagtgcaaggtctccaacaaagccctcccagcccccattgagaagaccatttccaaagcgaaagggcaacccc
gtgaaccacaagtgtacacacttcctccatctcgcgatgaactgaccaagaaccaggtcagcttgacttgcctggtgaaaggcttctatccctctgaca
tagctgtagagtgggagagcaatgggcaaccggagaacaactacaagactacacctcccgttctcgattctgacggctccttcttcctctacagcaag
ctcacagtggacaagagcaggtggcaacaagggaatgtcttctcatgctccgtgatgcatgaggctcttcacaatcactacacacagaagagtctctc
cttgtctccgggtaaatgaggatcc (SEQ ID NO:27)

*Amino Acid Sequence*

MGWSCIILFLVATATGVHSEVQVQQSGPELVTPGASVKISCKTSGYTFTEYTVHWVKQSHGKSLEWIGGINPTSGGT
NYNQRFRGKATLTVDRSSSTAYMELRSLTSEDSAVYFCAGTLYGYIFDFWGQGTTLTVSSGSTSGGGSGGGSGGGS
SDILMTQSPSSMSVSLGDSVSITCHASQGISGNIGWLQQKPGKSFKGLIYHGTNLEGVPSRFSGSGSGADYSLTIS
SLESEDFADYYCVQYGQFPPTFGGGTKLEIKASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYQSTYRVVSVLTVLHQDWLNGK
EYKCKVSNKALPAPIEKTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK (SEQ ID NO:28)

E60 scFv LALA Mutant

*Nucleic Acid Sequence* gaattcacaatgggatggtcttgtatcatcctttttcttggttgcaacagctactggtgttcattctgaggtccaggtgcaacagtctggacctgaactggt
gacgcctggggcctcagtgaagatatcctgcaagacttctggatacactttcactgaatataccgtccactgggtgaagcagagccatggaaagagcc
ttgagtggattggaggcattaatcctaccagtggtggtactaactacaaccagaggttcaggggcaaggccacattgactgtagacaggtcctccagc
acagcctacatggagctccgcagcctgacatctgaggattctgcagtctattttgtgcaggaaccctctatggctaccctttttgacttctggggccaag
gcaccactctcacagtctcctcaGGTTCAACTTCAGGAGGAGGATCAGGTGGTGGTTCAGGAGGTGGAGGATCTTCTgaca
tcctgatgacccaatctccatcctccatgtctgtatctctgggagactcagtcagcatcacttgccatgcaagtcagggcattagcggtaatatagggtg
gttgcagcagaaaccagggaaatcatttaagggcctgatctatcatggaaccaacttggaagagggagttccatcaaggttcagtggcagtggatctg
gagcagattattctctcaccatcagcagcctggagtctgaagattttgcagactattactgtgtacagtatggtcagtttcctccgacgttcggtggagg
caccaagctggaaatcaaagctagcaccaagggaccttctgtttttccacttgctccttcttctaagtctacttctggtggaactgctgctttgggttgttt
ggtgaaagattactttcctgagccagtgaccgtttcttggaactcaggtgctcttacatctggtgttcatactttcccagctgttcttcaatcttcaggactt
tactcactttcttctgttgttaccgttccttcttcaagcttgggcactcagacctacatctgcaatgtgaatcacaaacccagcaacaccaaggttgacaa
gaaagttgagcccaagtcttgtgacaagactcatacgtgtccaccgtgcccagcacctgaaGCtGCtggaggaccgtcagtcttcttgtttcctccaa
agcctaaggataccttgatgatctccaggactcctgaagtcacatgtgtagttgtggatgtgagccatgaagatcctgaggtgaagttcaactggtatg
tggatggtgtggaagtgcacaatgccaagacaaagccgagagaggaacagtacaacagcacgtacagggttgtctcagttctcactgttctccatca
agattggttgaatggcaaagagtacaagtgcaaggtctccaacaaagccctcccagcccccattgagaagaccatttccaaagcgaaagggcaacc
ccgtgaaccacaagtgtacacacttcctccatctcgcgatgaactgaccaagaaccaggtcagcttgacttgcctggtgaaaggcttctatccctctga
catagctgtagagtgggagagcaatgggcaaccggagaacaactacaagactacacctcccgttctcgattctgacggctccttcttcctctacagca

FIGURE 17-6 agctcacagtggacaagagcaggtggcaacaagggaatgtcttctcatgctccgtgatgcatgaggctcttcacaatcactacacacagaagagtctc
tccttgtctccgggtaaatgaggatcc (SEQ ID NO:29)

*Amino Acid Sequence*

MGWSCIILFLVATATGVHSEVQVQQSGPELVTPGASVKISCKTSGYTFTEYTVHWVKQSHGKSLEWIGGINPTSGGT
NYNQRFRGKATLTVDRSSSTAYMELRSLTSEDSAVYFCAGTLYGYPFDFWGQGTTLTVSSGSTSGGGSGGGSGGGGS
SDILMTQSPSSMSVSLGDSVSITCHASQGISGNIGWLQQKPGKSFKGLIYHGTNLEEGVPSRFSGSGSGADYSLTIS
SLESEDFADYYCVQYGQFPPTFGGGTKLEIKASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKKVEPKSCDKTHTCPPCPAPEAAGGPSV
FLFPPKPKDTLMISRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK (SEQ ID NO:30)

E60 scFv LALAGA Mutant

*Nucleic Acid Sequence* gaattcacaatgggatggtcttgtatcatccttttcttggttgcaacagctactggtgttcattctgaggtccaggtgcaacagtctggacctgaactggt
gacgcctggggcctcagtgaagatatcctgcaagacttctggatacactttcactgaatataccgtccactgggtgaagcagagccatggaaagagcc
ttgagtggattggaggcattaatcctaccagtggtggtactaactacaaccagaggttcaggggcaaggccacattgactgtagacaggtcctccagc
acagcctacatggagctccgcagcctgacatctgaggattctgcagtctattttgtgcaggaaccctctatggctacccttttgacttctggggccaag
gcaccactctcacagtctcctcaGGTTCAACTTCAGGAGGAGGATCAGGTGGTGGTTCAGGAGGTGGAGGATCTTCTgaca
tcctgatgacccaatctccatcctccatgtctgtatctctgggagactcagtcagcatcacttgccatgcaagtcagggcattagcggtaatatagggtg
gttgcagcagaaaccagggaaatcatttaagggcctgatctatcatggaaccaacttggaagagggagttccatcaaggttcagtggcagtggatctg
gagcagattattctctcaccatcagcagcctggagtctgaagattttgcagactattactgtgtacagtatggtcagtttcctccgacgttcggtggagg
caccaagctggaaatcaaagctagcaccaagggaccttctgtttttccacttgctccttcttctaagtctacttctggtggaactgctgctttgggttgttt
ggtgaaagattactttcctgagccagtgaccgtttcttggaactcaggtgctcttacatctggtgttcatactttcccagctgttcttcaatcttcaggactt
tactcactttcttctgttgttaccgttccttcttcaagcttgggcactcagacctacatctgcaatgtgaatcacaaacccagcaacaccaaggttgacaa
gaaagttgagcccaagtcttgtgacaagactcatacgtgtccaccgtgcccagcacctgaaGCtGCtggagCaccgtcagtcttcttgtttcctccaa
agcctaaggataccttgatgatctccaggactcctgaagtcacatgtgtagttgtggatgtgagccatgaagatcctgaggtgaagttcaactggtatg
tggatggtgtggaagtgcacaatgccaagacaaagccgagagaggaacagtacaacagcacgtacagggttgtctcagttctcactgttctccatca
agattggttgaatggcaaagagtacaagtgcaaggtctccaacaaagccctcccagcccccattgagaagaccatttccaaagcgaaagggcaacc
ccgtgaaccacaagtgtacacacttcctccatctcgcgatgaactgaccaagaaccaggtcagcttgacttgcctggtgaaaggcttctatccctctga
catagctgtagagtgggagagcaatgggcaaccggagaacaactacaagactacacctcccgttctcgattctgacggctccttcttcctctacagca
agctcacagtggacaagagcaggtggcaacaagggaatgtcttctcatgctccgtgatgcatgaggctcttcacaatcactacacacagaagagtctc
tccttgtctccgggtaaatgaggatcc (SEQ ID NO:31)

*Amino Acid Sequence*

MGWSCIILFLVATATGVHSEVQVQQSGPELVTPGASVKISCKTSGYTFTEYTVHWVKQSHGKSLEWIGGINPTSGGT
NYNQRFRGKATLTVDRSSSTAYMELRSLTSEDSAVYFCAGTLYGYPFDFWGQGTTLTVSSGSTSGGGSGGGSGGGGS
SDILMTQSPSSMSVSLGDSVSITCHASQGISGNIGWLQQKPGKSFKGLIYHGTNLEEGVPSRFSGSGSGADYSLTIS
SLESEDFADYYCVQYGQFPPTFGGGTKLEIKASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKKVEPKSCDKTHTCPPCPAPEAAGAPSV

FIGURE 17-7

FLFPPKPKDTLMISRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK (SEQ ID NO:32)

E16 WT Heavy Chain

*Nucleic Acid Sequence*

Gaattcacaatgggatggtcttgtatcatccttttcttggttgcaacagctactggtgttcattctcaagttcaattggtgcagtcaggtgctgaggtgaa
gaaaccaggtgcttcagttaaggtttcttgtaaggcttctggttacacattcacagattattggattgaatgggtgagacaagctcctggtcagggtctt
gagtggatgggagatattctttgtggaactggaagaactagatacaacgagaaacttaaggctagagttactatgactgctgatacctctacatctact
gcttacatggaacttagatctttgagatcagatgacactgctgtgtactattgtgctaggtcagcttcttatggagactacgctgactattggggacaag
gtactactgttactgtgtcttctgcttctaccaagggaccttctgtttttccacttgctccttcttctaagtctacttctggtggaactgctgctttgggttgttt
ggtgaaagattactttcctgagccagtgaccgtttcttggaactcaggtgctcttacatctggtgttcatactttcccagctgttcttcaatcttcaggactt
tactcactttcttctgttgttaccgttccttcttcaagcttgggcactcagacctacatctgcaatgtgaatcacaaacccagcaacaccaaggttgacaa
gaaagttgagcccaagtcttgtgacaagactcatacgtgtccaccgtgcccagcacctgaacttcttggaggaccgtcagtcttcttgtttcctccaaag
cctaaggataccttgatgatctccaggactcctgaagtcacatgtgtagttgtggatgtgagccatgaagatcctgaggtgaagttcaactggtatgtg
gatggtgtggaagtgcacaatgccaagacaaagccgagagaggaacagtacaacagcacgtacagggttgtctcagttctcactgttctccatcaag
attggttgaatggcaaagagtacaagtgcaaggtctccaacaaagccctcccagcccccattgagaagaccatttccaaagcgaaagggcaacccc
gtgaaccacaagtgtacacacttcctccatctcgcgatgaactgaccaagaaccaggtcagcttgacttgcctggtgaaaggcttctatccctctgaca
tagctgtagagtgggagagcaatgggcaaccggagaacaactacaagactacacctcccgttctcgattctgacggctccttcttcctctacagcaag
ctcacagtggacaagagcaggtggcaacaagggaatgtcttctcatgctccgtgatgcatgaggctcttcacaatcactacacacagaagagtctctc
cttgtctccgggtaaatgaggatcc (SEQ ID NO:33)

*Amino Acid Sequence*

MGWSCIILFLVATATGVHSQVQLVQSGAEVKKPGASVKVSCKASGYTFTDYWIEWVRQAPGQGLEWMGDILCGTGRT
RYNEKLKARVTMTADTSTSTAYMELRSLRSDDTAVYYCARSASYGDYADYWGQGTTVTVSSASTKGPSVFPLAPSSK
STSGGTAALGCLVKDYFPEPVTVSWNSGALTSGVHTFPAVLQSSGLYSLSSVVTVPSSSLGTQTYICNVNHKPSNTK
VDKKVEPKSCDKTHTCPPCPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCSVMHEALHNHYTQKSL
SLSPGK (SEQ ID NO:34)

E16 Heavy Chain NQ Mutant

*Nucleic Acid Sequence*

Gaattcacaatgggatggtcttgtatcatccttttcttggttgcaacagctactggtgttcattctcaagttcaattggtgcagtcaggtgctgaggtgaa
gaaaccaggtgcttcagttaaggtttcttgtaaggcttctggttacacattcacagattattggattgaatgggtgagacaagctcctggtcagggtctt
gagtggatgggagatattctttgtggaactggaagaactagatacaacgagaaacttaaggctagagttactatgactgctgatacctctacatctact
gcttacatggaacttagatctttgagatcagatgacactgctgtgtactattgtgctaggtcagcttcttatggagactacgctgactattggggacaag
gtactactgttactgtgtcttctgcttctaccaagggaccttctgtttttccacttgctccttcttctaagtctacttctggtggaactgctgctttgggttgttt

FIGURE 17-8 ggtgaaagattactttcctgagccagtgaccgtttcttggaactcaggtgctcttacatctggtgttcatactttcccagctgttcttcaatcttcaggactt
tactcactttcttctgttgttaccgttccttcttcaagcttgggcactcagacctacatctgcaatgtgaatcacaaacccagcaacaccaaggttgacaa
gaaagttgagcccaagtcttgtgacaagactcatacgtgtccaccgtgcccagcacctgaacttcttggaggaccgtcagtcttcttgtttcctccaaag
cctaaggataccttgatgatctccaggactcctgaagtcacatgtgtagttgtggatgtgagccatgaagatcctgaggtgaagttcaactggtatgtg
gatggtgtggaagtgcacaatgccaagacaaagccgagagaggaacagtacCaAagcacgtacagggttgtctcagttctcactgttctccatcaag
attggttgaatggcaaagagtacaagtgcaaggtctccaacaaagccctcccagcccccattgagaagaccatttccaaagcgaaagggcaacccc
gtgaaccacaagtgtacacacttcctccatctcgcgatgaactgaccaagaaccaggtcagcttgacttgcctggtgaaaggcttctatccctctgaca
tagctgtagagtgggagagcaatgggcaaccggagaacaactacaagactacacctcccgttctcgattctgacggctccttcttcctctacagcaag
ctcacagtggacaagagcaggtggcaacaagggaatgtcttctcatgctccgtgatgcatgaggctcttcacaatcactacacacagaagagtctctc
cttgtctccgggtaaatgaggatcc (SEQ ID NO:35)

*Amino Acid Sequence*

MGWSCIILFLVATATGVHSQVQLVQSGAEVKKPGASVKVSCKASGYTFTDYWIEWVRQAPGQGLEWMGDILCGTGR
FYNEKLKARVTMTADTSTSTAYMELRSLRSDDTAVYYCARSASYGDYADYWGQGTTVTVSSASTKGPSVFPLAPSSK
STSGGTAALGCLVKDYFPEPVTVSWNSGALTSGVHTFPAVLQSSGLYSLSSVVTVPSSSLGTQTYICNVNHKPSNTK
VDKRVEPKSCDKTHTCPPCPAPELLGGPSVFLFPPKPKDTLMISRTPEVTCVVVDVSHEDPEVKFNWYVDGVEVHNA
KTKPREEQYQSTYRVVSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCSVMHEALHNHYTQKS
SLSPGK (SEQ ID NO:36)

E16 Heavy Chain LALA Mutant

*Nucleic Acid Sequence*

Gaattcacaatgggatggtcttgtatcatcctttttcttggttgcaacagctactggtgttcattctcaagttcaattggtgcagtcaggtgctgaggtgaa
gaaaccaggtgcttcagttaaggtttcttgtaaggcttctggttacacattcacagattattggattgaatgggtgagacaagctcctggtcagggtctt
gagtggatgggagatattctttgtggaactggaagaactagatacaacgagaaacttaaggctagagttactatgactgctgatacctctacatctact
gcttacatggaacttagatctttgagatcagatgacactgctgtgtactattgtgctaggtcagcttcttatggagactacgctgactattggggacaag
gtactactgttactgtgtcttctgcttctaccaagggaccttctgtttttccacttgctccttcttctaagtctacttctggtggaactgctgctttgggttgttt
ggtgaaagattactttcctgagccagtgaccgtttcttggaactcaggtgctcttacatctggtgttcatactttcccagctgttcttcaatcttcaggactt
tactcactttcttctgttgttaccgttccttcttcaagcttgggcactcagacctacatctgcaatgtgaatcacaaacccagcaacaccaaggttgacaa
gaaagttgagcccaagtcttgtgacaagactcatacgtgtccaccgtgcccagcacctgaaGCtGCtggaggaccgtcagtcttcttgtttcctccaa
agcctaaggataccttgatgatctccaggactcctgaagtcacatgtgtagttgtggatgtgagccatgaagatcctgaggtgaagttcaactggtatg
tggatggtgtggaagtgcacaatgccaagacaaagccgagagaggaacagtacaacagcacgtacagggttgtctcagttctcactgttctccatca
agattggttgaatggcaaagagtacaagtgcaaggtctccaacaaagccctcccagcccccattgagaagaccatttccaaagcgaaagggcaacc
ccgtgaaccacaagtgtacacacttcctccatctcgcgatgaactgaccaagaaccaggtcagcttgacttgcctggtgaaaggcttctatccctctga
catagctgtagagtgggagagcaatgggcaaccggagaacaactacaagactacacctcccgttctcgattctgacggctccttcttcctctacagca
agctcacagtggacaagagcaggtggcaacaagggaatgtcttctcatgctccgtgatgcatgaggctcttcacaatcactacacacagaagagtctc
tccttgtctccgggtaaatgaggatcc (SEQ ID NO:37)

FIGURE 17-9

*Amino Acid Sequence*

MGWSCIILFLVATATGVHSQVQLVQSGAEVKKPGASVKVSCKASGYTFTDYWIEWVRQAPGQGLEWMGDILCGTGRTRYNEKLKARVTMTADTSTSTAYMELRSLRSDDTAVYYCARSASYGDYADYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO:38)

E16 Heavy Chain LALAGA Mutant

*Nucleic Acid Sequence*

GaattcacaatgggatggtcttgtatcatccttttcttggttgcaacagctactggtgttcattctcaagttcaattggtgcagtcaggtgctgaggtgaagaaaccaggtgcttcagttaaggtttcttgtaaggcttctggttacacattcacagattattggattgaatgggtgagacaagctcctggtcagggtcttgagtggatgggagatattctttgtggaactggaagaactagatacaacgagaaacttaaggctagagttactatgactgctgatacctctacatctactgcttacatggaacttagatctttgagatcagatgacactgctgtgtactattgtgctaggtcagcttcttatggagactacgctgactattggggacaaggtactactgttactgtgtcttctgcttctaccaagggaccttctgtttttccacttgctccttcttctaagtctacttctggtggaactgctgctttgggttgtttggtgaaagattactttcctgagccagtgaccgtttcttggaactcaggtgctcttacatctggtgttcatactttcccagctgttcttcaatcttcaggacttttactcactttcttctgttgttaccgttccttcttcaagcttgggcactcagacctacatctgcaatgtgaatcacaaacccagcaacaccaaggttgacaagaaagttgagcccaagtcttgtgacaagactcatacgtgtccaccgtgcccagcacctgaaGCtGCtggagCaccgtcagtcttcttgtttcctccaaagcctaaggataccttgatgatctccaggactcctgaagtcacatgtgtagttgtggatgtgagccatgaagatcctgaggtgaagttcaactggtatgtggatggtgtggaagtgcacaatgccaagacaaagccgagagaggaacagtacaacagcacgtacagggttgtctcagttctcactgttctccatcaagattggttgaatggcaaagagtacaagtgcaaggtctccaacaaagccctcccagcccccattgagaagaccatttccaaagcgaaagggcaaccccgtgaaccacaagtgtacacacttcctccatctcgcgatgaactgaccaagaaccaggtcagcttgacttgcctggtgaaaggcttctatccctctgacatagctgtagagtgggagagcaatgggcaaccggagaacaactacaagactacacctcccgttctcgattctgacggctccttcttcctctacagcaagctcacagtggacaagagcaggtggcaacaagggaatgtcttctcatgctccgtgatgcatgaggctcttcacaatcactacacacagaagagtctctccttgtctccgggtaaatgaggatcc (SEQ ID NO:39)

*Amino Acid Sequence*

MGWSCIILFLVATATGVHSQVQLVQSGAEVKKPGASVKVSCKASGYTFTDYWIEWVRQAPGQGLEWMGDILCGTGRTRYNEKLKARVTMTADTSTSTAYMELRSLRSDDTAVYYCARSASYGDYADYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO:40)

PLANT-DERIVED ANTIBODIES AND DERIVATIVES THAT REDUCE RISK OF ANTIBODY-DEPENDENT ENHANCEMENT (ADE) OF INFECTION

RELATED APPLICATION

This application claims the benefit under 35 U.S.C. § 119(e) of U.S. Provisional Application No. 61/932,033, filed Jan. 27, 2014, the entire contents of which is hereby incorporated by reference.

FEDERALLY SPONSORED RESEARCH OR DEVELOPMENT

This invention was made with government support under U01 AI075549 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 3, 2015, is named 17555.024WO1_SL.txt and is 94,428 bytes in size.

BACKGROUND OF THE INVENTION

The development and implementation of targeted monoclonal antibody (MAb) therapy has provided new opportunities for controlling a wide range of clinical diseases. Although MAbs produced in mammalian cell culture systems have achieved remarkable clinical success, their high cost, long manufacturing time, and restricted production capacity have limited the availability, utility and potential of these drugs. Several of these challenges might be overcome by using plant expression systems, because they offer highly scalable production of MAbs at low cost with a low risk of introducing adventitious human or animal pathogens. Functional antibody production requires a eukaryotic host cell that can assemble four antibody polypeptides into a heterotetramer and perform complex N-linked glycosylation. Despite this complexity, a MAb was successfully expressed in tobacco plants only three years after the first plant-made biologic (Hiatt A, Cafferkey R, Bowdish K (1989) Production of antibodies in transgenic plants. Nature 342: 76-78). Since then, a variety of MAbs and their derivatives, such as IgG, IgA, single-chain variable fragments (scFv), and diabodies have been produced in plants (De Muynck B, Navarre C, Boutry M (2010) Production of antibodies in plants: status after twenty years. Plant Biotechnology Journal 8: 529-563). The largest reported MAb-based molecule produced in plants is a recombinant immune complex (RIC) (Phoolcharoen W, Bhoo S H, Lai H, Ma J, Arntzen C J, et al. (2011) Expression of an immunogenic Ebola immune complex in *Nicotiana benthamiana*. Plant Biotechnology Journal 9: 807-816). The ability of plants to express and assemble larger or more complex MAb-derived molecules such as tetravalent MAbs or bifunctional MAbs has not been described.

N-linked glycosylation of proteins occurs as a series of post-translational modification steps in host cells and depends on the proper folding of the target protein and its transport to the appropriate endomembrane compartment (Roth J (2002) Protein N-glycosylation along the secretory pathway: relationship to organelle topography and function, protein quality control, and cell interactions. Chemical reviews 102: 285-303). As such, MAb variants with significant polypeptide structural differences from the native molecule also may have appreciable differences in glycan structures. This potential structural difference may impact the pharmacokinetics, antigen binding, stability, effector functions, immunogenicity, and efficacy of a MAb and its derivatives. Currently, the difference of N-glycosylation between the parent MAb and its structural variants and the precise cause of these differences are not fully understood.

BRIEF SUMMARY OF THE INVENTION

In certain embodiments, the present invention describes the plant-based production of a therapeutic antibody.

In certain embodiments, the present invention provides a plant-produced monoclonal antibody (MAb) specific for a target virus, the MAb comprising a defined and highly-uniform N-glycoform, wherein the MAb has reduced antibody-dependent enhancement (ADE) as compared to a mammalian-produced MAb, and wherein the MAb has equivalent antigen binding affinity and kinetics, neutralization activity, and in vivo therapeutic activity against a target virus infection as compared to an antibody produced from non-plant cells including mammalian, yeast and bacterial cells. In certain embodiments, the comparison is to a mammalian cell culture-produced MAb. In certain embodiments, the N-glycoform is $GnGnXF_3$, Man5, Man7, Man8, Man9, GnGn, AGn, GnA, AA, GnGn $F_6$, $AGnF_6$, $GnAF_6$, $AAF_6$, GnNa, NaGn, NaA, ANa, NaNa, $GnNaF_6$, $NaGnF_6$, $NaAF_6$, $ANaF_6$, $NaNaF_6$, GnGnbi, $GnGnbiF_6$, AGnbi, GnAbi, AAbi, NaGnbi, GnNabi, NaAbi, ANabi, NaNabi, $AGnbiF_6$, $GnAbiF_6$, $AAbiF_6$, $NaGnbiF_6$, $GnNabiF_6$, $NaAbiF_6$, $ANabiF_6$, $NaNabiF_6$ (GnGn)(GnGn), $(GnGn)(GnGn)F_6$, $(AA)(AA)F_6$, $(Na)(Na)F_6$ (FIG. 1). In certain embodiments, the N-glycoform is $GnGnXF_3$, Man5, Man7, Man8, Man9, GnGn, AGn, GnA, AA, or GnGn $F_6$. In certain embodiments the N-glycoform is $GnGnXF_3$, Man5, Man7, Man8, or Man9. As used herein the antigen binding affinity and kinetics is measured by Surface plasmon resonance (SPR) and expressed by parameters of "on rate" $k_a$, "off rate" $k_d$, and binding constant $K_D$. As used herein the neutralization activity measures the ability of inhibition of an antibody on the infectivity of a specific virus, and expressed by EC50, the concentration of an antibody that induces half of the maximal inhibition. As used herein, the in vivo therapeutic activity is defined as the minimal concentrations of an antibody or its derivatives that prevent or clear infection of a virus in an animal model.

In certain embodiments, the plant-produced MAb is anti-West Nile virus (WNV) MAb E16:

Light chain nucleotide sequence:

```
                                     (SEQ ID NO: 1)
ATGGGATGGTCTTGTATCATCCTTTTCTTGGTTGCAACAGCTACTGGTGT

TCATTCTGATATCGTTATGACACAATCTCCAGATTCTTTGGCTGTTTCTC

TTGGAGAGAGGGCTACTATCAATTGCAAGGCTTCTCAAGATGTTTCTACT

GCTGTTGCTTGGTACCAACAGAAACCTGGACAGCCACCAAAACTTCTTAT

CTCTTGGGCATCTACTAGGCACACTGGAGTTCCAGATAGATTTTCTGGAT

CTGGATCTGGAACAGATTTCACTCTTACTATCTCATCTCTTCAAGCTGAG

GATGTTGCAGTTTATTACTGTCAGCAACATTATACAACTCCACTTACTTT
```

-continued

CGGACAAGGAACTAAGTTGGAGATCAAAAGAACTGTTGCTGCACCATCTG

TTTTCATCTTCCCTCCATCTGATGAGCAGTTGAAATCTGGAACTGCTTCT

GTTGTGTGCCTTCTTAATAACTTCTATCCTAGAGAGGCTAAAGTTCAGTG

GAAGGTGGATAACGCACTTCAATCTGGTAACTCTCAAGAGTCTGTTACAG

AGCAAGATTCTAAGGACTCAACTTACTCTCTTTCATCTACACTTACTTTG

TCAAAAGCAGATTACGAGAAACACAAAGTTTACGCATGCGAAGTTACTCA

TCAAGGACTTTCTTCACCAGTTACAAAGTCTTTCAATAGAGGAGAGTGTT

AA.

Heavy chain nucleotide sequence:

(SEQ ID NO: 2)

ATGGGATGGTCTTGTATCATCCTTTTCTTGGTTGCAACAGCTACTGGTGT

TCATTCTCAAGTTCAATTGGTGCAGTCAGGTGCTGAGGTGAAGAAACCAG

GTGCTTCAGTTAAGGTTTCTTGTAAGGCTTCTGGTTACACATTCACAGAT

TATTGGATTGAATGGGTGAGACAAGCTCCTGGTCAGGGTCTTGAGTGGAT

GGGAGATATTCTTTGTGGAACTGGAAGAACTAGATACAACGAGAAACTTA

AGGCTAGAGTTACTATGACTGCTGATACCTCTACATCTACTGCTTACATG

GAACTTAGATCTTTGAGATCAGATGACACTGCTGTGTACTATTGTGCTAG

GTCAGCTTCTTATGGAGACTACGCTGACTATTGGGGACAAGGTACTACTG

TTACTGTGTCTTCTGCTTCTACCAAGGGACCTTCTGTTTTTCCACTTGCT

CCTTCTTCTAAGTCTACTTCTGGTGGAACTGCTGCTTTGGGTTGTTTGGT

GAAAGATTACTTTCCTGAGCCAGTGACCGTTTCTTGGAACTCAGGTGCTC

TTACATCTGGTGTTCATACTTTCCCAGCTGTTCTTCAATCTTCAGGACTT

TACTCACTTTCTTCTGTTGTTACCGTTCCTTCTTCAAGCTTGGGCACTCA

GACCTACATCTGCAATGTGAATCACAAACCCAGCAACACCAAGGTTGACA

AGAAAGTTGAGCCCAAGTCTTGTGACAAGACTCATACGTGTCCACCGTGC

CCAGCACCTGAACTTCTTGGAGGACCGTCAGTCTTCTTGTTTCCTCCAAA

GCCTAAGGATACCTTGATGATCTCCAGGACTCCTGAAGTCACATGTGTAG

TTGTGGATGTGAGCCATGAAGATCCTGAGGTGAAGTTCAACTGGTATGTG

GATGGTGTGGAAGTGCACAATGCCAAGACAAAGCCGAGAGAGGAACAGTA

CAACAGCACGTACAGGGTTGTCTCAGTTCTCACTGTTCTCCATCAAGATT

GGTTGAATGGCAAAGAGTACAAGTGCAAGGTCTCCAACAAAGCCCTCCCA

GCCCCCATTGAGAAGACCATTTCCAAAGCGAAAGGGCAACCCCGTGAACC

ACAAGTGTACACACTTCCTCCATCTCGCGATGAACTGACCAAGAACCAGG

TCAGCTTGACTTGCCTGGTGAAAGGCTTCTATCCCTCTGACATAGCTGTA

GAGTGGGAGAGCAATGGGCAACCGGAGAACAACTACAAGACTACACCTCC

CGTTCTCGATTCTGACGGCTCCTTCTTCCTCTACAGCAAGCTCACAGTGG

ACAAGAGCAGGTGGCAACAAGGGAATGTCTTCTCATGCTCCGTGATGCAT

GAGGCTCTTCACAATCACTACACACAGAAGAGTCTCTCCTTGTCTCCGGG

TAAATGA.

In certain embodiments, the E16 WT MAb may also comprise an alternative heavy chain, which comprises a signal peptide (e.g., MGWSCIILFLVATATGVHS SEQ ID NO:41) at its N-terminus that targets the HC into the endomembrane system for secretion (see, e.g., SEQ ID NO:34). Accordingly, an alternative heavy chain nucleotide sequence for E16 WT heavy chain is shown in FIG. 17 (SEQ ID NO:33).

In certain embodiments, the plant-produced MAb is a single chain variant of E16 (scFv-Fc fusion molecule).

In certain embodiments, the plant-produced MAb is a single chain variant of E16 (scFv-$C_H^{1-3}$ fusion molecule). The DNA sequence of the variable region of HC ($V_H$) and LC ($V_L$) of pHu-E16 was fused together first to generate pHu-E16scFv, and then fused to the coding sequence of the $C_H^{1-3}$ of human IgG to form scFv-$C_H^{1-3}$.

scFv-$C_H^{1-3}$ sequence:

(SEQ ID NO: 3)

ATGGGATGGTCTTGTATCATCCTTTTCTTGGTTGCAACAGCTACTGGTGT

TCATTCTCAAGTTCAATTGGTGCAGTCAGGTGCTGAGGTGAAGAAACCAG

GTGCTTCAGTTAAGGTTTCTTGTAAGGCTTCTGGTTACACATTCACAGAT

TATTGGATTGAATGGGTGAGACAAGCTCCTGGTCAGGGTCTTGAGTGGAT

GGGAGATATTCTTTGTGGAACTGGAAGAACTAGATACAACGAGAAACTTA

AGGCTAGAGTTACTATGACTGCTGATACCTCTACATCTACTGCTTACATG

GAACTTAGATCTTTGAGATCAGATGACACTGCTGTGTACTATTGTGCTAG

GTCAGCTTCTTATGGAGACTACGCTGACTATTGGGGACAAGGTACTACTG

TTACTGTGTCTTCTGGTTCAACTTCAGGAGGAGGATCAGGTGGTGGTTCA

GGAGGTGGAGGATCTTCTGATATCGTTATGACACAATCTCCAGATTCTTT

GGCTGTTTCTCTTGGAGAGAGGGCTACTATCAATTGCAAGGCTTCTCAAG

ATGTTTCTACTGCTGTTGCTTGGTACCAACAGAAACCTGGACAGCCACCA

AAACTTCTTATCTCTTGGGCATCTACTAGGCACACTGGAGTTCCAGATAG

ATTTTCTGGATCTGGATCTGGAACAGATTTCACTCTTACTATCTCATCTC

TTCAAGCTGAGGATGTTGCAGTTTATTACTGTCAGCAACATTATACAACT

CCACTTACTTTCGGACAAGGAACTAAGTTGGAGATCAAAGCTAGCACCAA

GGGACCTTCTGTTTTTCCACTTGCTCCTTCTTCTAAGTCTACTTCTGGTG

GAACTGCTGCTTTGGGTTGTTTGGTGAAAGATTACTTTCCTGAGCCAGTG

ACCGTTTCTTGGAACTCAGGTGCTCTTACATCTGGTGTTCATACTTTCCC

AGCTGTTCTTCAATCTTCAGGACTTTACTCACTTTCTTCTGTTGTTACCG

TTCCTTCT*TCAAGCTT*GGGCACTCAGACCTACATCTGCAATGTGAAT

CACAAACCCAGCAACACCAAGGTTGACAAGAAAGTTGAGCCCAAGTCTTG

TGACAAGACTCATACGTGTCCACCGTGCCCAGCACCTGAACTTCTTGGAG

GACCGTCAGTCTTCTTGTTTCCTCCAAAGCCTAAGGATACCTTGATGATC

TCCAGGACTCCTGAAGTCACATGTGTAGTTGTGGATGTGAGCCATGAAGA

TCCTGAGGTGAAGTTCAACTGGTATGTGGATGGTGTGGAAGTGCACAATG

CCAAGACAAAGCCGAGAGAGGAACAGTACAACAGCACGTACAGGGTTGTC

TCAGTTCTCACTGTTCTCCATCAAGATTGGTTGAATGGCAAAGAGTACAA

GTGCAAGGTCTCCAACAAACCCTCCCAGCCCCCATTGAGAAGACCATTTC

CAAAGCGAAAGGGCAACCCCGTGAACCACAAGTGTACACACTTCCTCCAT

CTCGCGATGAACTGACCAAGAACCAGGTCAGCTTGACTTGCCTGGTGAAA

-continued

GGCTTCTATCCCTCTGACATAGCTGTAGAGTGGGAGAGCAATGGGCAACC

GGAGAACAACTACAAGACTACACCTCCCGTTCTCGATTCTGACGGCTCCT

TCTTCCTCTACAGCAAGCTCACAGTGGACAAGAGCAGGTGGCAACAAGGG

AATGTCTTCTCATGCTCCGTGATGCATGAGGCTCTTCACAATCACTACAC

ACAGAAGAGTCTCTCCTTGTCTCCGGGTAAATGA.

In certain embodiments, the plant-produced MAb is a single chain variant of E16 (scFv-$C_H^{1-3}$ molecule) consists of a single-chain variable fragment (scFv) of pHu-E16 fused to the heavy chain (HC) constant domains ($C_H^{1-3}$) of human IgG.

In certain embodiments, the plant-produced MAb is pHu-E16scFv-$C_H^{1-3}$.

In certain embodiments, the N-glycoform selectively binds to Fc receptors or C1q. In certain embodiments, the N-glycoform is $GnGnXF_3$, Man5, Man7, Man8, Man9, GnGn, AGn, GnA, AA, GnGn $F_6$, $AGnF_6$, $GnAF_6$, or $AAF_6$ In certain embodiments, the MAb is bivalent or tetravalent variant. In certain embodiments, the MAb is Tetra pHu-E16.

In certain embodiments, the MAb comprises a signal peptide (e.g., MGWSCIILFLVATATGVHS SEQ ID NO:41) at its N-terminus that targets the HC into the endomembrane system for secretion.

In certain embodiments, the present invention provides an anti-Dengue virus (DV) MAb E60. MAb E60 is a full antibody with mouse LC variable domain ($V_L$) fused to human LC constant domain ($C_L$, kappa) and HC variable domain ($V_H$) to human constant domains ($CH^{1-3}$) of IgG1. The development of mouse E60 full MAb was described in Oliphant et al, (2006) Journal of Virology, 80: 12149-12159.

In certain embodiments, the plant-produced MAb is DV MAb E60.

Light chain nucleotide sequence:

(SEQ ID NO: 4)

ATGGGATGGTCTTGTATCATCCTTTTCTTGGTTGCAACAGCTACTGGTGT

TCATTCTGACATCCTGATGACCCAATCTCCATCCTCCATGTCTGTATCTC

TGGGAGACTCAGTCAGCATCACTTGCCATGCAAGTCAGGGCATTAGCGGT

AATATAGGGTGGTTGCAGCAGAAACCAGGGAAATCATTTAAGGGCCTGAT

CTATCATGGAACCAACTTGGAAGAGGGAGTTCCATCAAGGTTCAGTGGCA

GTGGATCTGGAGCAGATTATTCTCTCACCATCAGCAGCCTGGAGTCTGAA

GATTTTGCAGACTATTACTGTGTACAGTATGGTCAGTTTCCTCCGACGTT

CGGTGGAGGCACCAAGCTGGAAATCAAAGCTAGCAGAACTGTTGCTGCAC

CATCTGTTTTCATCTTCCCTCCATCTGATGAGCAGTTGAAATCTGGAACT

GCTTCTGTTGTGTGCCTTCTTAATAACTTCTATCCTAGAGAGGCTAAAGT

TCAGTGGAAGGTGGATAACGCACTTCAATCTGGTAACTCTCAAGAGTCTG

TTACAGAGCAAGATTCTAAGGACTCAACTTACTCTCTTTCATCTACACTT

ACTTTGTCAAAAGCAGATTACGAGAAACACAAAGTTTACGCATGCGAAGT

TACTCATCAAGGACTTTCTTCACCAGTTACAAAGTCTTTCAATAGAGGAG

AGTGTTAA.

Heavy chain nucleotide sequence:

(SEQ ID NO: 5)

ATGGGATGGTCTTGTATCATCCTTTTCTTGGTTGCAACAGCTACTGGTGT

TCATTCTGAGGTCCAGGTGCAACAGTCTGGACCTGAACTGGTGACGCCTG

GGGCCTCAGTGAAGATATCCTGCAAGACTTCTGGATACACTTTCACTGAA

TATACCGTCCACTGGGTGAAGCAGAGCCATGGAAAGAGCCTTGAGTGGAT

TGGAGGCATTAATCCTACCAGTGGTGGTACTAACTACAACCAGAGGTTCA

GGGGCAAGGCCACATTGACTGTAGACAGGTCCTCCAGCACAGCCTACATG

GAGCTCCGCAGCCTGACATCTGAGGATTCTGCAGTCTATTTTTGTGCAGG

AACCCTCTATGGCTACCCTTTTGACTTCTGGGGCCAAGGCACCACTCTCA

CAGTCTCCTCAGCTAGCACCAAGGGACCTTCTGTTTTTCCACTTGCTCCT

TCTTCTAAGTCTACTTCTGGTGGAACTGCTGCTTTGGGTTGTTTGGTGAA

AGATTACTTTCCTGAGCCAGTGACCGTTTCTTGGAACTCAGGTGCTCTTA

CATCTGGTGTTCATACTTTCCCAGCTGTTCTTCAATCTTCAGGACTTTAC

TCACTTTCTTCTGTTGTTACCGTTCCTTCTTCAAGCTTGGGCACTCAGAC

CTACATCTGCAATGTGAATCACAAACCCAGCAACACCAAGGTTGACAAGA

AAGTTGAGCCCAAGTCTTGTGACAAGACTCATACGTGTCCACCGTGCCCA

GCACCTGAACTTCTTGGAGGACCGTCAGTCTTCTTGTTTCCTCCAAAGCC

TAAGGATACCTTGATGATCTCCAGGACTCCTGAAGTCACATGTGTAGTTG

TGGATGTGAGCCATGAAGATCCTGAGGTGAAGTTCAACTGGTATGTGGAT

GGTGTGGAAGTGCACAATGCCAAGACAAAGCCGAGAGAGGAACAGTACAA

CAGCACGTACAGGGTTGTCTCAGTTCTCACTGTTCTCCATCAAGATTGGT

TGAATGGCAAAGAGTACAAGTGCAAGGTCTCCAACAAAGCCCTCCCAGCC

CCCATTGAGAAGACCATTTCCAAAGCGAAAGGGCAACCCCGTGAACCACA

AGTGTACACACTTCCTCCATCTCGCGATGAACTGACCAAGAACCAGGTCA

GCTTGACTTGCCTGGTGAAAGGCTTCTATCCCTCTGACATAGCTGTAGAG

TGGGAGAGCAATGGGCAACCGGAGAACAACTACAAGACTACACCTCCCGT

TCTCGATTCTGACGGCTCCTTCTTCCTCTACAGCAAGCTCACAGTGGACA

AGAGCAGGTGGCAACAAGGGAATGTCTTCTCATGCTCCGTGATGCATGAG

GCTCTTCACAATCACTACACACAGAAGAGTCTCTCCTTGTCTCCGGGTAA

ATGA.

In certain embodiments, the E60 WT MAb may also comprise an alternative heavy chain, which comprises a signal peptide (e.g, MGWSCIILFLVATATGVHS SEQ ID NO:41) at its N-terminus that targets the HC into the endomembrane system for secretion (see, e.g., SEQ ID NO:18). Accordingly, in certain embodiments, an alternative heavy chain nucleotide sequence for E60 WT is shown in FIG. 17 (SEQ ID NO:17).

In certain embodiments, the plant-produced MAb is a single chain variant of DV MAb E60 (scFv-Fc fusion molecule).

In certain embodiments, the plant-produced MAb is a single chain variant of DV

MAb E60 (scFv-$C_H^{1-3}$).

(SEQ ID NO: 6)

ATGGGATGGTCTTGTATCATCCTTTTCTTGGTTGCAACAGCTACTGGTGT

TCATTCTGAGGTCCAGGTGCAACAGTCTGGACCTGAACTGGTGACGCCTG

GGGCCTCAGTGAAGATATCCTGCAAGACTTCTGGATACACTTTCACTGAA

TATACCGTCCACTGGGTGAAGCAGAGCCATGGAAAGAGCCTTGAGTGGAT

TGGAGGCATTAATCCTACCAGTGGTGGTACTAACTACAACCAGAGGTTCA

GGGGCAAGGCCACATTGACTGTAGACAGGTCCTCCAGCACAGCCTACATG

GAGCTCCGCAGCCTGACATCTGAGGATTCTGCAGTCTATTTTTGTGCAGG

AACCCTCTATGGCTACCCTTTTGACTTCTGGGGCCAAGGCACCACTCTCA

CAGTCTCCTCAGGTTCAACTTCAGGAGGAGGATCAGGTGGTGGTTCAGGA

GGTGGAGGATCTTCTGGATGGTCTTGTATCATCCTTTTCTTGGTTGCAAC

AGCTACTGGTGTTCATTCTGACATCCTGATGACCCAATCTCCATCCTCCA

TGTCTGTATCTCTGGGAGACTCAGTCAGCATCACTTGCCATGCAAGTCAG

GGCATTAGCGGTAATATAGGGTGGTTGCAGCAGAAACCAGGGAAATCATT

TAAGGGCCTGATCTATCATGGAACCAACTTGGAAGAGGGAGTTCCATCAA

GGTTCAGTGGCAGTGGATCTGGAGCAGATTATTCTCTCACCATCAGCAGC

CTGGAGTCTGAAGATTTTGCAGACTATTACTGTGTACAGTATGGTCAGTT

TCCTCCGACGTTCGGTGGAGGCACCAAGCTGGAAATCAAAGCAGCACCAA

GGGACCTTCTGTTTTTCCACTTGCTCCTTCTTCTAAGTCTACTTCTGGTG

GAACTGCTGCTTTGGGTTGTTTGGTGAAAGATTACTTTCCTGAGCCAGTG

ACCGTTTCTTGGAACTCAGGTGCTCTTACATCTGGTGTTCATACTTTCCC

AGCTGTTCTTCAATCTTCAGGACTTTACTCACTTTCTTCTGTTGTTACCG

TTCCTTCTTCAAGCTTGGGCACTCAGACCTACATCTGCAATGTGAATCAC

AAACCCAGCAACACCAAGGTTGACAAGAAAGTTGAGCCCAAGTCTTGTGA

CAAGACTCATACGTGTCCACCGTGCCCAGCACCTGAACTTCTTGGAGGAC

CGTCAGTCTTCTTGTTTCCTCCAAAGCCTAAGGATACCTTGATGATCTCC

AGGACTCCTGAAGTCACATGTGTAGTTGTGGATGTGAGCCATGAAGATCC

TGAGGTGAAGTTCAACTGGTATGTGGATGGTGTGGAAGTGCACAATGCCA

AGACAAAGCCGAGAGAGGAACAGTACAACAGCACGTACAGGGTTGTCTCA

GTTCTCACTGTTCTCCATCAAGATTGGTTGAATGGCAAAGAGTACAAGTG

CAAGGTCTCCAACAAAGCCCTCCCAGCCCCCATTGAGAAGACCATTTCCA

AAGCGAAAGGGCAACCCCGTGAACCACAAGTGTACACACTTCCTCCATCT

CGCGATGAACTGACCAAGAACCAGGTCAGCTTGACTTGCCTGGTGAAAGG

CTTCTATCCCTCTGACATAGCTGTAGAGTGGGAGAGCAATGGGCAACCGG

AGAACAACTACAAGACTACACCTCCCGTTCTCGATTCTGACGGCTCCTTC

TTCCTCTACAGCAAGCTCACAGTGGACAAGAGCAGGTGGCAACAAGGGAA

TGTCTTCTCATGCTCCGTGATGCATGAGGCTCTTCACAATCACTACACAC

AGAAGAGTCTCTCCTTGTCTCCGGGTAAATGA.

In certain embodiments, the N-glycoform selectively binds to Fc receptors or C1q.

In certain embodiments, the plant-produced MAb is a bivalent or tetravalent variant.

In certain embodiments, the MAb comprises a signal peptide (e.g., MGWSCIILFLVATATGVHS SEQ ID NO:41) at its N-terminus that targets the HC into the endomembrane system for secretion.

In certain embodiments, the plant-produced MAb is specific for a flavivirus, coronavirus, paramyxovirus, lentivirus, or other virus that is prone to ADE.

In certain embodiments, the present invention provides a nucleic acid molecule that encodes DV MAb E60.

In certain embodiments, a plant-produced MAb described herein further comprises a heavy chain (HC) comprising one or more amino acid mutations that affect Fc receptor or/and C1q binding. As described herein these mutations may decrease overall Fc receptor and/or C1q binding and/or increase the selectivity of the binding.

As used herein, L234, L235 and G237 refer to amino acids in the mature heavy chain of IgG1. As described herein, these amino acids may be mutated to affect Fc receptor and/or C1q binding. Additionally, mutations may alternatively be made at equivalent positions in other MAb isotypes and their subtypes and amino acids that correspond to, or align with, amino acids L234, L235 and G237 may be readily determined by one skilled in the art using known techniques (e.g., BLAST or ALIGN). The numbering of the amino acids may also vary with other alterations to the heavy chain, e.g., the inclusion of a signal peptide. For example, in FIG. 17, E16 and E60 HC constructs are shown: L234 is equivalent to L254 in E60 and L255 in E16; L235 is equivalent to L255 in E60 and L256 in E16; and G237 is equivalent G257 in E60 and G258 in E16.

Accordingly, in certain embodiments, the heavy chain of the antibody is a human IgG1 isotype and the one or more mutations are selected from L234AL235A, wherein the leucines at positions 234 and 235 are mutated to alanine, and L234AL235AG237A, wherein the leucines at positions 234 and 235 are mutated to alanine; and glycine at position 237 is mutated to alanine, or mutations that correspond to, or align with, L234AL235A and L234AL235AG237A. In certain embodiments, corresponding mutations may alternatively be made at equivalent positions in other MAb isotypes and their subtypes. In certain embodiments, the plant-produced MAb is a E16 mutant or an E16 scFv mutant, e.g., an E16 mutant comprising an amino acid sequence shown in FIG. 17, such as an E16 heavy chain LALA mutant (SEQ ID NO:38) or an E16 heavy chain LALAGA mutant (SEQ ID NO:40). In certain embodiments, the plant-produced MAb is a E60 mutant or an E60 scFv mutant, e.g., an E60 mutant comprising an amino acid sequence shown in FIG. 17, such as an E60 heavy chain LALA mutant (SEQ ID NO:22), an E60 heavy chain LALAGA mutant (SEQ ID NO:24), an E60 scFv LALA mutant (SEQ ID NO:30) or an E60 scFv LALAGA mutant (SEQ ID NO:32).

As described herein, MAbs that only need neutralization activities for their function, but cause ADE, may be mutated to eliminate glycosylation and Fc receptor and/or C1q binding, thereby reducing ADE.

Accordingly, certain embodiments of the invention provide a plant-produced monoclonal antibody (MAb) specific for a target virus, wherein the MAb is aglycosylated and comprises a heavy chain (HC) comprising one or more amino acid mutations that result in an aglycosylated MAb, wherein the MAb has reduced antibody-dependent enhancement (ADE) as compared to a mammalian-produced MAb. In certain embodiments, the MAb has equivalent antigen binding affinity and kinetics, neutralization activity, and in vivo therapeutic activity against a target virus infection as compared to an antibody produced from non-plant cells including mammalian, yeast and bacterial cells.

Accordingly, certain embodiments of the invention also provide a plant-produced monoclonal antibody (MAb) specific for a target virus, wherein the MAb is aglycosylated and comprises a heavy chain (HC) comprising one or more amino acid mutations that eliminate Fc receptor or/and C1q binding, wherein the MAb has reduced antibody-dependent enhancement (ADE) as compared to a mammalian-produced MAb. In certain embodiments, the MAb has equivalent antigen binding affinity and kinetics, neutralization activity, and in vivo therapeutic activity against a target virus infection as compared to an antibody produced from non-plant cells including mammalian, yeast and bacterial cells. In certain embodiments, the MAb comprises two or more mutations.

In certain embodiments, an N-glycosylation site in the MAb is mutated, wherein the mutation results in aglycosylation of the MAb (i.e., the N-glycan is eliminated and not attached to the antibody). In certain embodiments, the N-glycosylation site consensus sequence N-X-S/T is mutated, wherein N is asparagine, X is any amino acid, and S/T is serine or threonine.

As used herein, N297 refers to an amino acid in the mature heavy chain of IgG1. As described herein, this amino acid may be mutated to result in an aglycosylated MAb. Additionally, a mutation may alternatively be made at equivalent positions in other MAb isotypes and their subtypes and an amino acid that corresponds to, or aligns with, amino acid N297 may be readily determined by one skilled in the art using known techniques (e.g., BLAST or ALIGN). The numbering of the amino acids may also vary with other alterations to the heavy chain, e.g., the inclusion of a signal peptide. For example, in FIG. 17, E16 and E60 HC constructs are shown: N297 is equivalent to N317 in E60 and N318 in E16.

Accordingly, in certain embodiments, the N in the consensus sequence is at the position of 297 in human IgG1 or its equivalent position for other MAb isotypes and their subtypes (e.g., a position that corresponds to, or aligns with, N297). In certain embodiments, the HC is a human IgG1 isotype, and the mutation is N297Q (or an N to Q mutation at a position that corresponds to, or aligns with 297). In certain embodiments, a corresponding mutation may alternatively be made at an equivalent position in other MAb isotypes and their subtypes. In certain embodiments, the plant-produced aglycosylated MAb is a E16 mutant or an E16 scFv mutant, e.g., an E16 mutant comprising an N to Q mutation as shown in SEQ ID NO:36. In certain embodiments, the plant-produced MAb is a E60 mutant or an E60 scFv mutant, e.g., comprising an N to Q mutation as shown in SEQ ID NO:20 or SEQ ID NO:28, respectively.

In certain embodiments, the heavy chain of the aglycosylated MAb is a human IgG1 isotype and the one or more mutations that eliminate Fc receptor or/and C1q binding are selected from L234AL235A and L234AL235AG237A (see, e.g., FIG. 17, wherein mutations were made at corresponding positions in various constructs). In certain embodiments, corresponding mutations may alternatively be made at equivalent positions in other MAb isotypes and their subtypes.

As described above, certain HC mutations may decrease overall Fc receptor and/or C1q binding and/or increase the selectivity of the binding, thereby reducing ADE. Accordingly, certain embodiments of the invention provide a plant-produced monoclonal antibody (MAb) specific for a target virus, wherein the MAb comprises a heavy chain (HC) comprising one or more amino acid mutations that alter Fc receptor or/and C1q binding, wherein the MAb has reduced antibody-dependent enhancement (ADE) as compared to a mammalian-produced MAb, and wherein the MAb has equivalent antigen binding affinity and kinetics, neutralization activity, and in vivo therapeutic activity against a target virus infection as compared to an antibody produced from non-plant cells including mammalian, yeast and bacterial cells. In certain embodiments, the heavy chain comprises two or three amino acid mutations. In certain embodiments, the heavy chain is a human IgG1 isotype and the mutations are selected from L234AL235A and L234AL235AG237A (see, e.g., FIG. 17, wherein mutations were made at corresponding positions in various constructs). In certain embodiments, corresponding mutations may alternatively be made at equivalent positions in other MAb isotypes and their subtypes.

In certain embodiments, the present invention provides a population of plant-produced monoclonal antibodies (MAb) specific for a target virus, the MAbs comprising a defined and highly-uniform N-glycoform, wherein the N-glycoform is $GnGnXF_3$, Man5, Man7, Man8, Man9, GnGn, AGn, GnA, AA, GnGn $F_6$, $AGnF_6$, $GnAF_6$, $AAF_6$, GnNa, NaGn, NaA, ANa, NaNa, $GnNaF_6$, $NaGnF_6$, $NaAF_6$, $ANaF_6$, $NaNaF_6$, GnGnbi, $GnGnbiF_6$, AGnbi, GnAbi, AAbi, NaGnbi, GnNabi, NaAbi, ANabi, NaNabi, $AGnbiF_6$, $GnAbiF_6$, $AAbiF_6$, $NaGnbiF_6$, $GnNabiF_6$, $NaAbiF_6$, $ANabiF_6$, $NaNabiF_6$ (GnGn)(GnGn), $(GnGn)(GnGn)F_6$, $(AA)(AA)F_6$, or $(Na)(Na)F_6$ as depicted in FIG. 1, wherein the MAbs have reduced antibody-dependent enhancement (ADE) as compared to mammalian-produced MAbs, and wherein the MAbs have equivalent antigen binding affinity and kinetics, neutralization activity, and in vivo therapeutic activity against a target virus infection as compared to an antibody produced from non-plant cells including mammalian, yeast and bacterial cells.

Certain embodiments of the invention provide a population of plant-produced monoclonal antibodies (MAbs) specific for a target virus, wherein the MAbs are aglycosylated and comprises a heavy chain (HC) comprising one or more amino acid mutations that eliminate Fc receptor or/and C1q binding, wherein the MAbs have reduced antibody-dependent enhancement (ADE) as compared to a mammalian-produced MAb. In certain embodiments, the MAbs have equivalent antigen binding affinity and kinetics, neutralization activity, and in vivo therapeutic activity against a target virus infection as compared to an antibody produced from non-plant cells including mammalian, yeast and bacterial cells.

Certain embodiments of the invention provide a population of plant-produced monoclonal antibodies (MAbs) specific for a target virus, wherein the MAbs comprise a heavy chain (HC) comprising one or more amino acid mutations that alter Fc receptor or/and C1q binding, wherein the MAbs have reduced antibody-dependent enhancement (ADE) as compared to a mammalian-produced MAb, and wherein the MAbs have equivalent antigen binding affinity and kinetics, neutralization activity, and in vivo therapeutic activity against a target virus infection as compared to an antibody produced from non-plant cells including mammalian, yeast and bacterial cells.

In certain embodiments, the present invention provides a method of modulating antibody-dependent enhancement (ADE) of an antibody comprising contacting the antibody with an N-glycan. In certain embodiments, the N-glycan is $GnGnXF_3$, Man5, Man7, Man8, Man9, GnGn, AGn, GnA, AA, or GnGn $F_6$. In certain embodiments, the N-glycan is $GnGnXF_3$, Man5, Man7, Man8, or Man9. In certain embodiments, the methods further comprise mutating the antibody heavy chain (e.g., L234AL235A or L234AL235AG237A, or equivalent mutations at corresponding/alignable positions). In certain embodiments, corresponding mutations may alternatively be made at equivalent positions in other MAb isotypes and their subtypes.

In certain embodiments, the present invention provides a method of modulating antibody-dependent enhancement (ADE) of an antibody comprising mutating the amino acid sequence of the antibody heavy chain. In certain embodiments, the amino acid sequence of the antibody heavy chain is a human IgG1 isotype and comprises mutations L234AL235A or L234AL235AG237A or mutations that correspond to, or align with, these positions. In certain embodiments, corresponding mutations may alternatively be made at equivalent positions in other MAb isotypes and their subtypes.

In certain embodiments, the present invention provides a method of producing a MAb having a defined and highly-uniform N-glycoform, wherein the N-glycoform is $GnGnXF_3$, Man5, Man7, Man8, Man9, GnGn, AGn, GnA, AA, GnGn $F_6$, $AGnF_6$, $GnAF_6$, $AAF_6$, GnNa, NaGn, NaA, ANa, NaNa, $GnNaF_6$, $NaGnF_6$, $NaAF_6$, $ANaF_6$, $NaNaF_6$, GnGnbi, $GnGnbiF_6$, AGnbi, GnAbi, AAbi, NaGnbi, GnNabi, NaAbi, ANabi, NaNabi, $AGnbiF_6$, $GnAbiF_6$, $AAbiF_6$, $NaGnbiF_6$, $GnNabiF_6$, $NaAbiF_6$, $ANabiF_6$, $NaNabiF_6$ (GnGn)(GnGn), $(GnGn)(GnGn)F_6$, $(AA)(AA)F_6$, $(Na)(Na)F_6$ as depicted in FIG. 1 comprising (a) growing a plant comprising a nucleic acid encoding the MAb, and (b) isolating the MAb, wherein the MAb has reduced antibody-dependent enhancement (ADE) as compared to a mammalian-produced MAb, and wherein the MAb has equivalent antigen binding affinity and kinetics, neutralization activity and in vivo therapeutic activity against a target virus infection as compared to an antibody produced from non-plant cells including mammalian, yeast and bacterial cells. In certain embodiments, the plant is a wild-type *Nicotiana benthamiana* or a glycol-engineered *N. benthamiana* plant that produces N-glycoforms of $GnGnXF_3$, Man5, Man7, Man8, Man9, GnGn, AGn, GnA, AA, $GnGnF_6$, AAF6, NaNa, NaNaF6, GnGnbi, or (GnGn)(GnGn) (See FIG. 1) as described in reference (Castilho, A. and H. Steinkellner (2012). "Glyco-engineering in plants to produce human-like N-glycan structures." *Biotechnology Journal* 7(9): 1088-1098).

In certain embodiments, the nucleic acid encodes a MAb with one or more amino acid mutations in its heavy chain (HC) that affect Fc receptor and/or C1q binding. In certain embodiments, the HC is a human IgG1 isotype and the one or more mutations are selected from L234AL235A and L234AL235AG237A, or equivalent mutations at corresponding/alignable positions. In certain embodiments, corresponding mutations may alternatively be made at equivalent positions in other MAb isotypes and their subtypes.

In certain embodiments, the plant is a wild-type *Nicotiana benthamiana* or a glycol-engineered *N. benthamiana* plant that produce N-glycoforms of $GnGnXF_3$, Man5, Man7, Man8, Man9, GnGn, AGn, GnA, AA, $GnGnF_6$, AAF6, NaNa, NaNaF6, GnGnbi, or (GnGn)(GnGn) as depicted in FIG. 1).

In certain embodiments, the present invention provides another method of producing a MAb having a defined and highly-uniform N-glycoform $GnGnXF_3$, Man5, Man7, Man8, Man9, GnGn, AGn, GnA, AA, GnGn $F_6$ comprising (a) growing a plant;

(b) transiently expressing MAb and glycol-enzymes in the plant by co-infiltrating plant with *Agrobacterium* stains containing the genetic constructs of MAb heavy chain (HC), light chain (LC), and glycol-enzymes; and (c) isolating the MAb, wherein the MAb has reduced antibody-dependent enhancement (ADE) as compared to a mammalian-produced MAb, and wherein the MAb has equivalent antigen binding affinity and kinetics, neutralization activity kinetics and in vivo therapeutic activity kinetics against a target virus infection as compared to an antibody produced from non-plant cells including mammalian, yeast and bacterial cells.

In certain embodiments, the MAb HC construct encodes a HC comprising one or more amino acid mutations that affect Fc receptor and/or C1q binding. In certain embodiments, the HC of a MAb is altered at two or three positions that affect its interaction with C1q or/and Fc receptors. In certain embodiments, the MAb HC construct encodes a human IgG1 HC isotype and the one or more mutations are selected from L234AL235A and L234AL235AG237A, or equivalent mutations at corresponding/alignable positions (Hezareh, et al. (2001). "Effector Function Activities of a Panel of Mutants of a Broadly Neutralizing Antibody against Human Immunodeficiency Virus Type 1." *Journal of Virology* 75(24): 12161-12168). In certain embodiments, the MAb HC construct may encode an alternative MAb isotype/subtype with corresponding mutations.

In certain embodiments, the HC of a MAb is tagged with an endoplasmic reticulum (ER)-retention/retrieval signal.

In certain embodiments, the ER-retention/retrieval signal is a peptide sequence containing the four amino acid H/KDEL (SEQ ID NO:7) or its variant attached to the carboxyl-terminus of the heavy chain of an antibody.

In certain embodiments, the HC of the MAb is tagged with a signal peptide (e.g., MGWSCIILFLVATATGVHS SEQ ID NO:41) at the N-terminus of the heavy chain (HC), which targets the HC into the endomembrane system for secretion.

In certain embodiments, the plant is wild-type *Nicotiana benthamiana* or a glycol-engineered *N. benthamiana* plant that produces N-glycoform of GnGn (See FIG. 1) as described in reference (Castilho, A. and H. Steinkellner (2012). "Glyco-engineering in plants to produce human-like N-glycan structures." *Biotechnology Journal* 7(9): 1088-1098). In certain embodiments, the glyco-enzyme is β1,4-galactosyltranserase (GalT), α1,6-fucosyltransferase (FUT8), human β1,4-mannosyl-β1,4-N-acetylglucosaminyltransferase (GnTIII), α1,3-mannosyl-β1,4-N-acetylglucosaminyltransferase (GnTIV), α1,6-mannosyl-β1,6-N-acetylglucosaminyltransferase (GnTV), UDP-N-acetylglucosamine 2-epimerase/N-acetylmannosamine-kinase (GNE), N-acetylneuraminic acid phosphate-synthase (NANS), CMP-Neu5Ac transporter (CST), or α2,6-or α2,3-sialyltransferase.

In certain embodiments, the genetic construct of one glycol-enzyme is co-infiltrated into a plant with those of MAb LC and HC. In certain embodiments, the genetic constructs of more than one glycol-enzymes are co-infiltrated into a plant with those of MAb LC and HC. In certain embodiments, the plant is a wild-type *Nicotiana benthamiana* or a glycol-engineered *N. benthamiana* plant that produces N-glycoform of GnGn.

Certain embodiments of the invention provide a method of producing an aglycosylated MAb comprising (a) growing a plant comprising a nucleic acid encoding the MAb, wherein the encoded MAb comprises a mutation that results in aglycosylation of the MAb (e.g, a mutation at an N-glycosylation site in the MAb heavy chain (HC)), and (b) isolating the MAb, wherein the MAb has reduced antibody-dependent enhancement (ADE) as compared to a mammalian-produced MAb. In certain embodiments, the MAb has equivalent antigen binding affinity and kinetics, neutralization activity, and in vivo therapeutic activity against a target virus infection as compared to an antibody produced from non-plant cells including mammalian, yeast and bacterial cells.

In certain embodiments, a N-glycosylation site consensus sequence N-X-S/T in the MAb HC is mutated, and wherein N is asparagine, X is any amino acid, and S/T is serine or threonine. In certain embodiments, the HC is a human IgG1 isotype, and the mutation is N297Q, or an equivalent mutation that corresponds to, or aligns with, this position. In certain embodiments, corresponding a mutation may alternatively be made at an equivalent position in other MAb isotypes and their subtypes.

In certain embodiments, the encoded MAb further comprises one or more amino acid mutations that eliminate Fc receptor or/and C1q binding. In certain embodiments, the HC is a human IgG1 isotype and the one or more mutations are selected from L234AL235A and L234AL235AG237A, or equivalent mutations that correspond to, or align with, these positions. In certain embodiments, corresponding mutations may alternatively be made at equivalent positions in other MAb isotypes and their subtypes.

Certain embodiments of the invention provide a method of producing an aglycosylated MAb comprising (a) growing a plant; (b) transiently expressing the MAb in the plant by co-infiltrating the plant with *Agrobacterium* strains containing the genetic constructs of MAb HC and LC, wherein the genetic construct of the MAb HC comprises a mutation that results in aglycosylation of the MAb (e.g, a mutation altering an N-glycosylation site); and (c) isolating the MAb, wherein the MAb has reduced antibody-dependent enhancement (ADE) as compared to a mammalian-produced MAb. In certain embodiments, the MAb has equivalent antigen binding affinity and kinetics, neutralization activity kinetics and in vivo therapeutic activity kinetics against a target virus infection as compared to an antibody produced from non-plant cells including mammalian, yeast and bacterial cells.

In certain embodiments, the genetic construct of the MAb HC comprises a mutation that alters an N-glycosylation site consensus sequence N-X-S/T, and wherein N is asparagine, X is any amino acid, and S/T is serine or threonine. In certain embodiments, the genetic construct of the MAb HC encodes a human IgG1 isotype comprising an N297Q mutation, or an N to Q mutation at a corresponding/alignable position. In certain embodiments, a corresponding mutation may alternatively be made at an equivalent position in other MAb isotypes and their subtypes.

In certain embodiments, the MAb HC genetic construct encodes an HC further comprising one or more mutations that eliminate Fc receptor or/and C1q binding. In certain embodiments, the HC is an IgG1 isotype and the one or more mutations are selected from L234AL235A and L234AL235AG237A, or equivalent mutations at corresponding/alignable positions. In certain embodiments, corresponding mutations may alternatively be made at equivalent positions in other MAb isotypes and their subtypes.

In certain embodiments, the plant is a wild-type *Nicotiana benthamiana* or any glyco-engineered *N. benthamiana* plants.

Certain embodiments of the invention provide a method of producing a MAb having altered Fc receptor and/or C1q binding comprising (a) growing a plant comprising a nucleic acid encoding the MAb, wherein the encoded MAb comprises one or more amino acid mutations in its heavy chain that alter Fc receptor and/or C1q binding, (b)isolating the MAb, wherein the MAb has reduced antibody-dependent enhancement (ADE) as compared to a mammalian-produced MAb, and wherein the MAb has equivalent antigen binding affinity and kinetics, neutralization activity, and in vivo therapeutic activity against a target virus infection as compared to an antibody produced from non-plant cells including mammalian, yeast and bacterial cells.

Certain embodiments of the invention provide a method of producing a MAb having altered Fc receptor and/or C1q binding comprising (a) growing a plant; (b) transiently expressing MAb in the plant by co-infiltrating the plant with *Agrobacterium* strains containing the genetic constructs of MAb HC and LC, wherein the HC genetic construct encodes an HC comprising one or more mutations that alter Fc receptor and/or C1q binding; and (c) isolating the MAb, wherein the MAb has reduced antibody-dependent enhancement (ADE) as compared to a mammalian-produced MAb, and wherein the MAb has equivalent antigen binding affinity and kinetics, neutralization activity kinetics and in vivo therapeutic activity kinetics against a target virus infection as compared to an antibody produced from non-plant cells including mammalian, yeast and bacterial cells.

In certain embodiments, the MAb HC is an IgG1 isotype and the one or more mutations are selected from L234AL235A and L234AL235AG237A, or equivalent mutations at corresponding/alignable positions. In certain embodiments, corresponding mutations may alternatively be made at equivalent positions in other MAb isotypes and their subtypes.

In certain embodiments, the MAb binds to Fc receptors and/or C1q with increased selectivity. In certain embodiments, the MAb binding to Fc receptors and/or C1q is reduced. In certain embodiments, the method further comprises transiently expressing a glyco-enzyme(s) in the plant by infiltrating the plant with an *Agrobacterium* strain(s) containing the genetic construct of a glycol-enzyme(s). In certain embodiments, the glyco-enzyme is β1,4-galactosyltranserase (GalT), α1,6-fucosyltransferase (FUT8), human β1,4-mannosyl-β1,4-N-acetylglucosaminyltransferase (GnTIII), α1,3-mannosyl-β1,4-N-acetylglucosaminyltransferase (GnTIV), α1,6-mannosyl-β1,6-N-acetylglucosaminyltransferase (GnTV), UDP-N-acetylglucosamine 2-epimerase/N-acetylmannosamine-kinase (GNE), N-acetylneuraminic acid phosphate-synthase (NANS), CMP-Neu5Ac transporter (CST), or α2,6-or α2,3-sialyltransferase.

In certain embodiments, the genetic construct of one glycol-enzyme is co-infiltrated into a plant with those of MAb LC and HC. In certain embodiments, the genetic constructs of more than one glycol-enzymes are co-infiltrated into a plant with those of MAb LC and HC.

In certain embodiments, the plant is a wild-type *Nicotiana benthamiana* or a glyco-engineered *N. benthamiana* plant that produce N-glycoforms of $GnGnXF_3$, Man5, Man7, Man8, Man9, GnGn, AGn, GnA, AA, $GnGnF_6$, AAF6, NaNa, NaNaF6, GnGnbi, or (GnGn)(GnGn) as depicted in FIG. 1. In certain embodiments, the plant is a wild-type

*Nicotiana benthamiana* or a glyco-engineered *N. benthamiana* plant that produces N-glycoform of GnGn.

BRIEF DESCRIPTION OF THE DRAWINGS

FIG. 16. Relative abundance in percentage of major glyco-structures detected on HuE16 variants.

FIG. 17. Nucleic acid and amino acid sequences for various E60 and E16 constructs. Each nucleic acid construct also includes a sequence that encodes a signal peptide (MGWSCIILFLVATATGVHS SEQ ID NO:41) at the N-terminus of the heavy chain (HC), which targets the HC into the endomembrane system for secretion.

DETAILED DESCRIPTION OF THE INVENTION

One of the major impediments towards developing vaccines and antibody-based therapeutics for many viruses is the risk of antibody-dependent enhancement (ADE), which may render vaccinated or anti-viral antibody treated subjects more susceptible to infection. The ability of obtaining MAb variants with specific and selective interaction with Fc receptors or C1q is crucial for reducing ADE. N-glycosylation of a MAb plays an important role in its interaction with the Fc receptors and C1q. Therefore, the ability of obtaining highly uniform N-glycans for MAb drug is crucial for identifying MAb variants with reduced or eliminated ADE. Previous studies on this subject have been limited by the difficulty in obtaining antibodies with a homogenous glycoform due to the heterogeneous N-glycan nature of mammalian cells. Previous attempts to obtain various defined glycoforms for selecting the right glycoforms to reduce ADE were unsuccessful. This is due to the fact that current approaches to alter the glycoform of IgGs by glycosylation inhibitors or treatment with glycosidases are inadequate in producing specifically defined glycoforms. Other attempts were made to use aglycosylated MAbs (MAbs have no N-glycosylation) for reducing ADE. While aglycosylated MAbs cannot bind FcγRs or cause ADE, they may become less stable and lose the necessary effector function (CDC or ADCC) required for their full therapeutic effect. Accordingly, aglycosylated MAbs with reduced ADE may be useful where only neutralization activities are needed for their function.

The present study indicated that it is possible to use plants to produce monoclonal antibody (MAb) drugs to reduce or even eliminate their ability to induce ADE. In certain embodiments, the present plant system is superior in producing MAbs with highly uniform N-glycans. This reduces the risk of ADE and enhances the safety of many MAb drugs for viral infections. Because in certain embodiments the present plant-produced MAbs are still glycosylated, they are stable and retain selective ADCC and CDC activity for full therapeutic function and potency, while losing or greatly reducing ADE.

Figure 13:
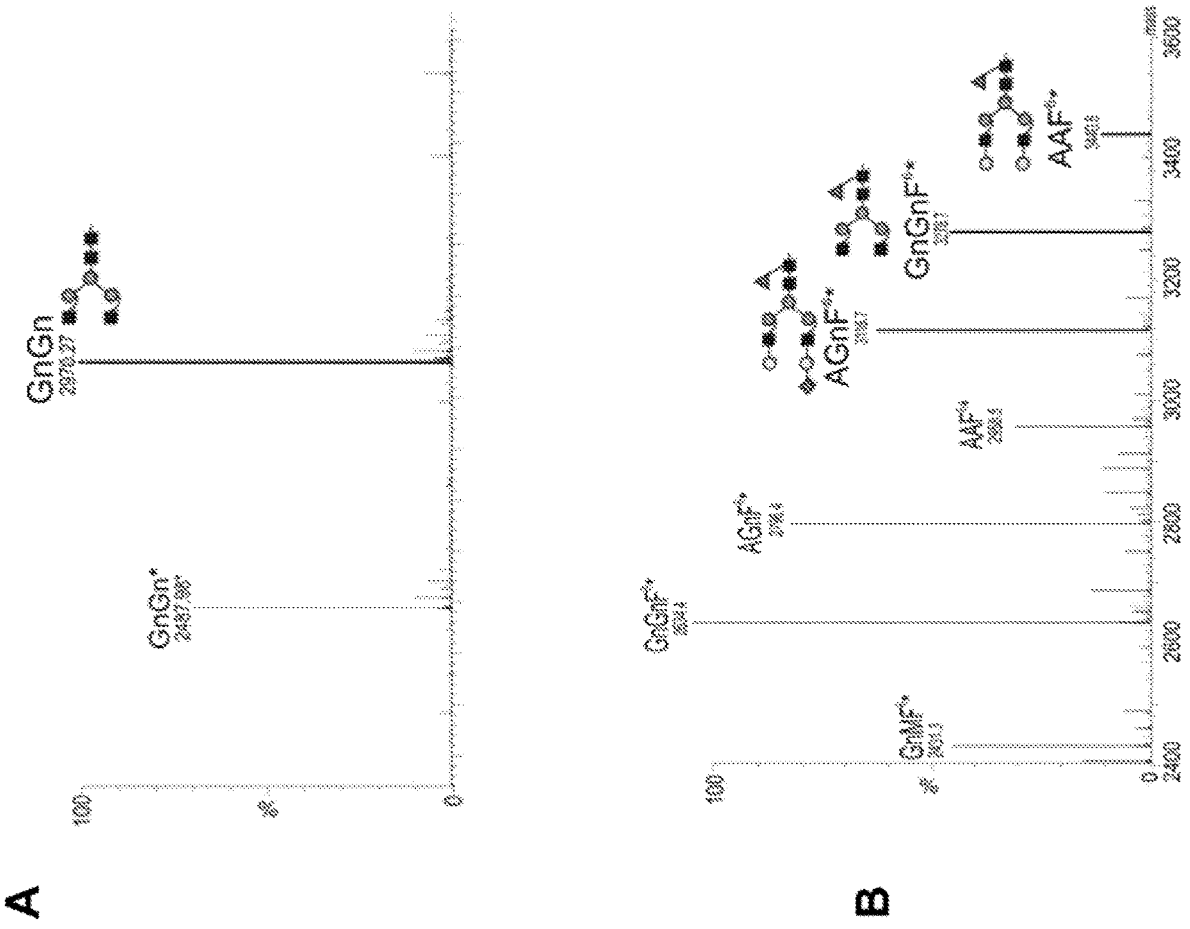
FIG. 13. N-linked glycan analysis of E16 antibody produced in glycoengineered *N. benthamiana*. Glycosylated peptides containing the Asn297 residue of the CH region were obtained from E16 purified from ΔXF Plants (A) or mammalian cells E16 (B) by tryptic digestion, and analyzed by LC-ESI-MS. Due to an incomplete tryptic digestion two glycopeptides were generated that differ by 482 Da. Glycopeptide (GP) 1 is indicated with an asterisk, GP 2 is highlighted.

Plants are uniquely able to produce MAb or MAb derivatives with highly homogeneous or uniform N-glycosylation patterns. For example, >90% of pE16 MAb produced in wild-type (WT) *N. benthamiana* plants display the N-glycosylation form of GnGnXF3 (FIG. 16). If an endoplasmic reticulum (ER)-retention/retrieval signal such as a peptide sequence containing the four amino acid H/KDEL (SEQ ID NO:7) or its variant is attached to the carboxyl-terminus of the heavy chain of an antibody, predominantly ER-type oligomannosidic (Man7, Man8 and Man9, FIG. 1) N-linked glycans will be produced for MAbs by WT and other plant lines. In addition, when fused to part of heavy chain, single-chain variants of an MAb such as scFv-Fc and scFv-$CH^{1-3}$ molecules also displayed Man8 and Man9-types of oligomannosidic structures when expressed in plants. Several plant lines have been developed by genetically suppressing or eliminating enzymes for the biosynthesis of plant-specific glycans and by introducing glycoenzymes from mammalian cells (Lai, H., M. Engle, et al. (2010). "Monoclonal antibody produced in plants efficiently treats West Nile virus infection in mice." Proceedings of the National Academy of Sciences of the United States of America 107(6): 2419-2424). For example, a *N. benthamiana* plant line (ΔXF) was generated by RNA interference (RNAi) technology with down-regulated expression of the endogenous β1,2-xylosyltransferase and α1,3-fucosyltransferase genes. N-glycan analysis showed that ΔXF line-produced endogenous glycoproteins exhibited a profile with complex-type N-glycans virtually lacking the plant-specific xylose and a significant reduction of α1,3-fucose for endogenous proteins (Loos, A., B. Van Droogenbroeck, et al. (2011). "Expression of antibody fragments with a controlled N-glycosylation pattern and induction of endoplasmic reticulum-derived vesicles in seeds of *Arabidopsis*." Plant Physiol 155(4): 2036-48). Moreover, MAbs produced in this plant line have a homogenous mammalian N-glycoform with terminal N-acetylglucosamine (Gn) residues (i.e., GnGn structures), lacking unwanted β1,2-xylose and core α1,3-fucose residues (FIG. 13) (Loos, A., B. Van Droogenbroeck, et al. (2011). "Expression of antibody fragments with a controlled N-glycosylation pattern and induction of endoplasmic reticulum-derived vesicles in seeds of *Arabidopsis*." Plant Physiol 155(4): 2036-48). Similarly, the plant lines with down-regulated or knocked-out endogenous β1,2-xylosyltransferase and α1,3-fucosyltransferase genes have been generated for the aquatic plant *Lemna minor*, the moss *Physcomitrella patens, Medicago sativa* and rice cells. Other glycol-engineered plant lines include *N. benthamiana* lines that perform β-1,4-galactosylation (produces AA N-glycans, created by expressing human β1,4-galactosyltranserase (GalT) fused to the amino-terminal cytoplasmic-transmembrane-stem (CTS) region of rat α2,6-sialyltransferase (ST)), and α1,6-fucosylation (expressing human α1,6-fucosyltransferase (FUT8)). Plant lines that produce bisected, tri- and tetra-antennary N-glycans (for example, GnGnbi, and (GnGn)(GnGn), FIG. 1) (by expressing human β1,4-mannosyl-β1,4-N-acetylglucosaminyltransferase (GnTIII), α1,3-mannosyl-β1,4-N-acetylglucosaminyltransferase (GnTIV) and α1,6-mannosyl-β1,6-N-acetylglucosaminyltransferase (GnTV)) and terminal sialylation (by expressing UDP-N-acetylglucosamine 2-epimerase/N-acetylmannosamine-kinase (GNE), N-acetylneuraminic acid phosphate-synthase (NANS), CMP-Neu5Ac transporter (CST), GalT, and α2,6-or α2,3-sialyltransferase (ST)) are also developed.

Figure 1:
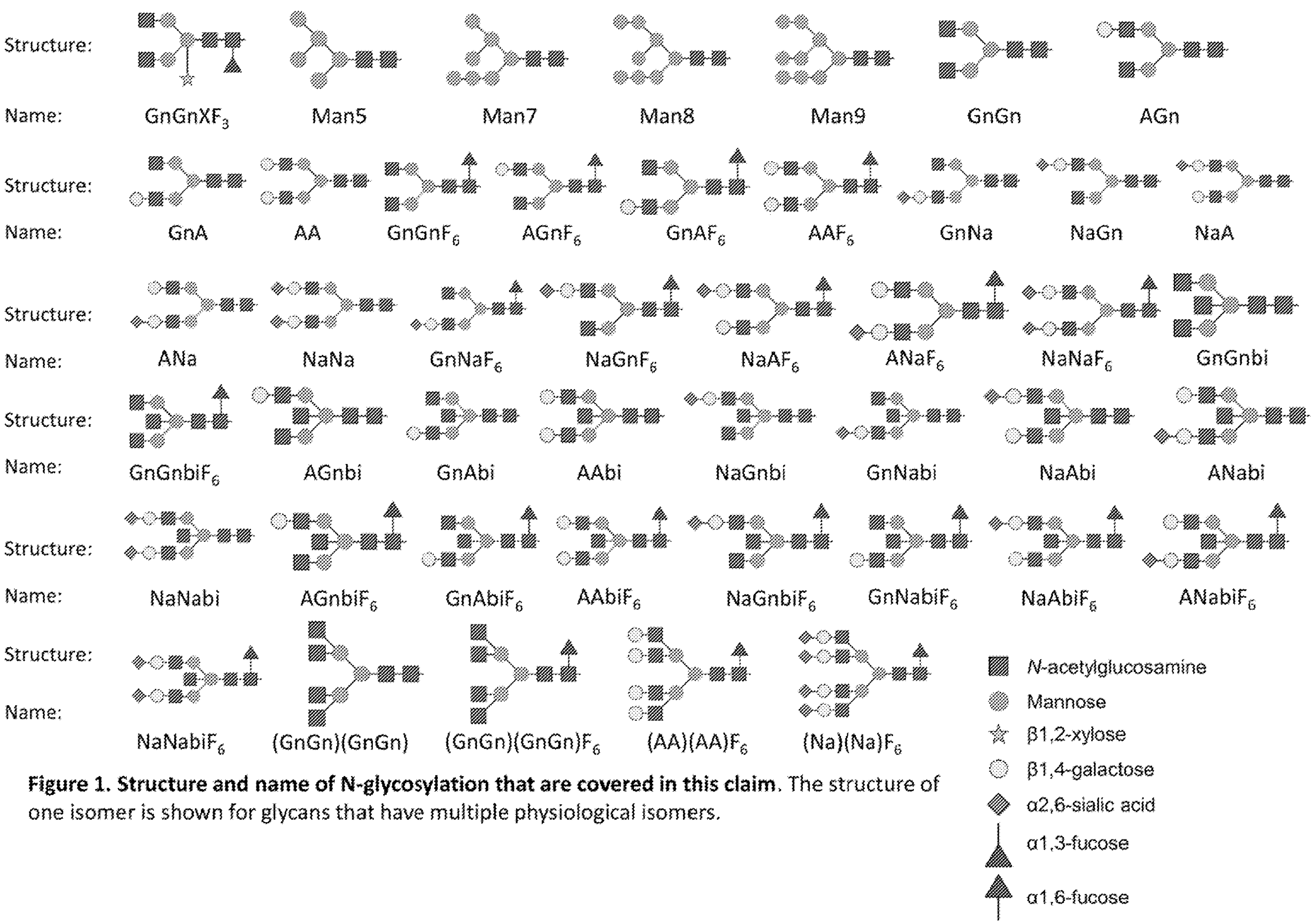
FIG. 1. Structure and name of N-glycosylation forms that are provided in certain embodiments. The structure of one major isomer is shown for glycans that have multiple physiological isomers.

WT plants and each of these plant lines produces a defined glycoform for MAbs as shown in FIG. 1 with $GnGnXF_3$, Man5, Man7, Man8, Man9, GnGn, AGn, GnA, AA, GnGn $F_6$ as the most promising glycoforms. In addition to these stable plant lines, MAbs with particular glycoforms can also be produced by transiently co-expressing the genetic construct of glycol-enzymes individually or in combinations (including GalT, FUT8, GnTIII, GnTIV, GnTV, GNE, MANS, CST and ST) with the MAb HC and LC constructs in either WT or ΔXF plant lines through plant transient expression systems. Both of these approaches allow the selection of particular glycoforms that reduce or eliminate ADE, while maintain the therapeutic potency of the MAb. In addition to N-glycosylation, amino acid replacement in the HC of a MAb, e.g. L234AL235A and L234AL235AG237A (Hezareh, et al. (2001). "Effector Function Activities of a Panel of Mutants of a Broadly Neutralizing Antibody against Human Immunodeficiency Virus Type 1." *Journal of Virology* 75(24): 12161-12168) has also been used to alter the antibody interaction with Fc receptors and C1q. Such glycoforms and glycoforms+HC amino acid replacement combinations have been identified by the present studies for an anti-West Nile virus antibody and an anti-Dengue virus antibody. This approach is applicable to many other antibodies or antibody-derivative-based drugs that treat viruses that are prone to ADE.

Dengue Virus (DV)

Dengue virus (DV) is a member of the Flavivirus genus of the Flaviviridae family. DV is the most common mosquito-transmitted viral disease in the world, with ~50 to 100 million infections per year. DV infection causes a spectrum of disease ranging from Dengue fever (DF) to the life-threatening Dengue hemorrhagic fever/Dengue shock syndrome (DHF/DSS). DV is a category A NIAID priority pathogen, a potential bioterrorism agent, and imposes a substantial economic and social liability, as it remains a leading cause of hospitalization and death of children in at least eight Southeast Asian countries. One of the major impediments towards developing vaccines and antibody-based therapeutics for DV and other viruses is the risk of ADE, which may render vaccinated or anti-DV antibody treated subjects more susceptible to infection. ADE occurs because pre-existing sub-neutralizing concentrations of antibodies (including therapeutic monoclonal antibodies (MAbs)) and the infecting DV form complexes that bind to Fc-γ receptor (FcγR)-bearing cells, resulting in increased virus uptake and replication. The binding of human IgG to FcγR is highly sensitive to the presence and the nature of the N-linked glycosylation at position N297 in its CH2 domain. Previous studies on this subject have been limited by the difficulty in obtaining antibodies with a homogenous glycoform due to the heterogeneous N-glycan nature of mammalian cells and incompetent chemical modification method. While aglycosylated MAbs cannot bind FcγRs or cause ADE, they may become less stable, have shorter half-life in circulation (altered pharmacokinetics) and lose the necessary effector function required for their full therapeutic effect. Therefore, aglycosylated MAbs are only desirable when they function solely through neutralization. Recent progress in plant glycoengineering has allowed the generation of transgenic plant lines that produce MAbs with defined and uniform mammalian N-linked glycans. This progress has allowed the study of how Fc glycosylation of MAbs affects ADE.

West Nile Virus (WNV)

West Nile virus (WNV) is a member of the Flavivirus genus of the Flaviviridae family, which also includes the Japanese encephalitis virus (JE), Tick-borne encephalitis virus (TBE), St. Louis Encephalitis virus (SLEV), Murray Valley encephalitis virus, dengue virus (including the four serotypes of: DEN-1, DEN-2, DEN-3, and DEN-4), and the family prototype, yellow fever virus (YF). Flavivirus infections are a global public health with about half of the flaviviruses causing human diseases.

WNV is a neurotropic, enveloped virus with a single-stranded, positive polarity, 11 kilobase RNA genome. Until 1999, WNV was found in the Eastern Hemisphere, with wide distribution in Africa, Asia, the Middle East, and Europe. In 1999, WNV entered the Western Hemisphere as a point introduction in New York City. Greater than 29,000 human cases have been diagnosed with severe WNV infection in the continental United States during the last decade, and many more have been infected and remain undiagnosed. Advanced age is by far the greatest risk factor for severe neurological disease, long-term morbidity, and death, although a genetic basis of susceptibility has also been recently identified.

Historically, there has been a lack of effective and specific antiviral treatment for infection by WNV or other flaviviruses. While several small molecules compounds have been recently described with antiviral activity against WNV in vitro, only few have demonstrated efficacy in vivo. Interferon (IFN), which is used as part of combination therapy against the distantly related hepatitis C virus, potently inhibits flaviviruses including WNV when used as prophylaxis. However, its effect is markedly attenuated once viral replication has commenced as flavivirus non-structural proteins antagonize IFN signaling pathways. Current treatment for WNV infection is supportive and no vaccine or therapeutic agent has been approved for human use. New threats of WNV globally and lack of available treatments warrant studies to develop effective therapeutics and production technologies that can rapidly transfer the candidates into the clinical care settings in a cost-conscious manner.

Recently, a plant-derived humanized murine MAb was developed with promising therapeutic potential. This MAb (E16) binds to a highly conserved epitope on the envelope protein of WNV in all North American isolates, blocks viral fusion, and shows promising post-exposure therapeutic activity. Nonetheless, detailed studies show that while the E16 is therapeutically effective, peripheral delivery of this antibody has a limited window of efficacy in rodents. For example, administration of a single dose of hu-E16 through an intravenous or intraperitonreal route at day 5 postinfection or earlier improves survival rates. However, delivery of E16 directly into the brain at day 6 after infection can protect hamsters against lethal WNV infection.

Even though antibodies have been identified as potential prophylactic and or therapeutic medicaments for WNV or other infectious diseases, their ultimate application as beneficial therapeutics is limited lack of efficacy due to the short therapeutic window and the risk of antibody-dependent enhancement (ADE). Thus, there remains a need for effective, safe vaccines. In addition, the there is a need to alleviate the high production costs and scalability associated with the mammalian cell culture production system. Moreover, if biological drugs are too costly to produce for resource poor health care systems and cannot be easily made into generics, their therapeutic potential may never be realized. As such, the development of production platforms that are cost-effective, scalable, and safe for biological therapeutics is urgently needed.

Despite annual WNV outbreaks in North America there is a lack of effective and specific antiviral treatment. The high production costs and limited scalability associated with mammalian cell culture production may restrict the use of therapeutic antibodies against WNV and other flaviviruses in resource-poor settings in the future. Here, the feasibility of producing in plants a candidate MAb therapeutic against WNV infection was investigated. The inventors have shown that plant-derived MAb therapeutics have similar potency as their mammalian-cell counterparts, and production of biological therapeutics in plants provides a platform that can address the cost and scalability issues associated with the mammalian cell culture production system. Further, these plant-derived therapeutics circumvent the issue of ADE.

In this invention, the inventors generated several monoclonal antibody (MAb) therapeutics in plants and in mammalian culture cells that can effectively treat West Nile virus (WNV) infection, do not induce ADE, and can also be rapidly scaled-up for commercial production.

The plant-derived MAbs retain the biological and therapeutic activity of the parental MAb in high-affinity binding and potent neutralizing activity in vitro against the target virus, and in protecting mice against viral-induced mortality.

Most of the current antibodies and their fragments are developed in either mammalian cell or bacterial cultures. Generation of these molecules in current systems has been hindered by difficulties especially in obtaining properly folded full-length molecules in sufficient quantities that retain conformationally-sensitive epitopes. The present invention showed that in addition to mammalian cells, plants can also be readily used to produce a MAb successfully without any of these production issues. Since plants can rapidly express, accumulate and assemble MAb, and this can be expanded for commercial production without high-capital investments.

Transgenic plants are suitable for MAb production as they can be rapidly expanded in commercial production without the high-capital investment associated with traditional MAb bioreactor facilities. pHu-E16 was expressed rapidly in *N. benthamiana* leaves within 4 to 8 days of infiltration and efficiently assembled into a native IgG form. Without any genetic optimization, pHu-E16 accumulated at an average of 0.8 mg/g of fresh leaf weight, greater than the highest expression level for MAbs in plants ever reported (Giritch A, et al. (2006) Rapid high-yield expression of full-size IgG antibodies in plants coinfected with noncompeting viral vectors. *Proc Natl Acad Sci USA*. 103: 14701-14706). The rapid high-level production and assembly of pHu-E16 convincingly demonstrate the viability of this system for the more large-scale cost effective production of MAbs.

It is well-known that downstream processing is an important component of a pharmaceutical protein production technology. In the present invention, there is described a simple three-step extraction and purification scheme that can be used to purify plant-generated MAb efficiently and in a manner that is scalable for mass production and conforms to cGMP regulations, thereby providing a method for the production of a pharmaceutically acceptable preparation of MAb. The rapid high-level accumulation of MAb in plants and the availability of a scalable and cGMP compliant processing scheme provides advantages over the mammalian cell culture for future low-cost commercial production of MAb.

The N-linked glycosylation of proteins in plants is generally similar to that in mammalian cells. However, plants have unique plant-specific β-1,2-xylose and core α-1,3-fucose residues on complex N-linked glycans and lack terminal β-1,4-Gal and N acetylneuraminic acid (Neu5Ac) residues (Gomord V, et al. (2004) Production and glycosylation of plant-made pharmaceuticals: the antibodies as a challenge. *Plant Biotechnol* J. 2: 83-100). The impact of such differences on the activity of MAb therapeutics in vivo has not been evaluated, although glycan variations in the Fc region of IgG modulate the binding and activation of C1 q (Raju T S (2008) Terminal sugars of Fc glycans influence antibody effector functions of IgGs. *Curr Opin Immunol*. 20: 471-478; Wang F, et al. (2006) Structural and functional characterization of glycosylation in an immunoglobulin G1 to Cryptococcus neoformans glucuronoxylomannan. *Mol Immunol*. 43: 987-998). Since pHu-E16 HC has an ER-retention KDEL (SEQ ID NO:8) sequence, it is likely retained in the ER resulting in a predominately high mannose form of glycosylation (Ko K, et al. (2003) Function and glycosylation of plant-derived antiviral monoclonal antibody. *Proc Natl Acad Sci USA*. 100: 8013-8018), which contributes to the reduced affinity to C1q (Qun Z, et al. (2008) Development of a simple and rapid method for producing non-fucosylated oligomannose containing antibodies with increased effector function. *Biotechnol Bioeng*. 99: 652-665).

The difference between plant and mammalian glycosylation patterns raises concerns for the immunogenicity of plant-derived MAb therapeutics. The possibility of inducing plant-glycan specific antibodies could reduce therapeutic efficacy by accelerating clearance from plasma, or cause potential adverse effects through immune complex formation. Immunization studies with plant glycoproteins in different animal models have yielded inconsistent results: rats and rabbits develop antibodies to plant specific xylose and α-1,3-fucose, yet mice generate no antibody response against these glycans (Chargelegue D, et al. (2000) A murine monoclonal antibody produced in transgenic plants with plant-specific glycans is not immunogenic in mice. *Transgenic Res*. 9: 187-194; Jin C, et al. (2008) A plant derived human monoclonal antibody induces an anticarbohydrate immune response in rabbits. *Glycobiology*). Moreover, no adverse effects were observed in patients with topical application of plant-produced MAbs with plant unique carbohydrates (Zeitlin L, et al. (1998) A humanized monoclonal antibody produced in transgenic plants for immunoprotection of the vagina against genital herpes. *Nat Biotech.* 16: 1361-1364; Ma J K, et al. (1998) Characterization of a recombinant plant monoclonal secretory antibody and preventive immunotherapy in humans. *Nat Med.* 4: 601-606). To date, the immunogenicity of systemic administered plant-produced MAbs has not been evaluated in humans.

To avoid problems associated with plant-specific glycans, "humanized" *N. benthamiana, Arabidopsis thaliana* and *Lemna minor* plant lines have been generated by genetic knockout or RNA interference (RNAi) strategies (Schahs M, et al. (2007) Production of a monoclonal antibody in plants with a humanized N-glycosylation pattern. *Plant Biotechnol J* 5: 657-663; Strasser R, et al. (2008) Generation of glyco-engineered Nicotiana benthamiana for the production of monoclonal antibodies with a homogeneous human-like N glycan structure. *Plant Biotechnol J.* 6: 392-402; Cox K M, et al. (2006) Glycan optimization of a human monoclonal antibody in the aquatic plant *Lemna minor. Nat Biotechnol.* 24: 1591-1597). In these plants, enzymes for the biosynthesis of plant specific glycans are inactivated, resulting in structurally equivalent MAbs as those derived in mammalian cells. Moreover, the glycan uniformity of MAbs produced by these optimized plant lines is better than those from mammalian cell cultures. Indeed, an anti-human CD30 MAb produced from these genetically modified plants had only a single predominant N-glycan species and showed improved antibody-dependent cell-mediated cytotoxicity (ADCC) compared to the same MAb produced in mammalian cells (Cox K M, et al. (2006) Glycan optimization of a human monoclonal antibody in the aquatic plant *Lemna minor. Nat Biotechnol.* 24: 1591-1597). This improvement is most likely due to the removal of fucose, which results in improved FcγR binding of MAbs (Shields R L, et al. (2002) Lack of fucose on human IgG1N-linked oligosaccharide improves binding to human Fcgamma RIII and antibody-dependent cellular toxicity. *J Biol Chem.* 277: 26733-26740). The therapeutic utility of pHu-E16 can be improved by expression in such "humanized" *N. benthamiana* lines.

In brief, the Example provided below demonstrates that plant-derived MAbs can function effectively as post-exposure therapy against a potentially lethal infectious disease. Plants are an efficient platform to produce Hu-E16 with high-yield, speed, enhanced scalability, and cost-effectiveness, satisfying all major metrics for a successful therapeutic candidate. This technology can be readily applied in the future to antiviral antibodies against other emerging infectious disease threats, and may be most useful in resource poor settings such as the developing world.

E16 is a monoclonal antibody that strongly neutralizes WNV and a humanized version of this antibody has been described in the art that retains its neutralizing activity and avidity (Oliphant T, et al. (2005) Development of a humanized monoclonal antibody with therapeutic potential against West Nile virus. *Nat Med.* 11: 522-530).

The generalized structure of antibodies or immunoglobulin is well known to those of skill in the art, these molecules are heterotetrameric glycoproteins, typically of about 150,000 daltons, composed of two identical light (L) chains and two identical heavy (H) chains. Each light chain is covalently linked to a heavy chain by one disulfide bond to form a heterodimer, and the heterotrameric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain (VH), followed by three or four constant domains (CH1, CH2, CH3, and CH4), as well as a hinge region between CH1 and CH2. Each light chain has two domains, an amino-terminal variable domain (VL) and a carboxy-terminal constant domain (CL). The VL domain associates non-covalently with the VH domain, whereas the CL domain is commonly covalently linked to the CH1 domain via a disulfide bond. Particular amino acid residues are believed to form an interface between the light and heavy chain variable domains (Chothia et al., 1985, J. Mol. Biol. 186:651-663.)

Certain domains within the variable domains differ extensively between different antibodies i.e., are "hypervariable." These hypervariable domains contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, 5th Ed. Public Health Service, National Institutes of Health, Bethesda, Md., whereas HVLs are structurally defined according to the three-dimensional structure of the variable domain, as described by Chothia and Lesk, 1987, J. Mol. Biol. 196: 901-917. Where these two methods result in slightly different identifications of a CDR, the structural definition is preferred. As defined by Kabat, CDR-L1 is positioned at about residues 24-34, CDR-L2, at about residues 50-56, and CDR-L3, at about residues 89-97 in the light chain variable domain; CDR-H1 is positioned at about residues 31-35, CDR-H2 at about residues 50-65, and CDR-H3 at about residues 95-102 in the heavy chain variable domain. The CDR1, CDR2, CDR3 of the heavy and light chains therefore define the unique and functional properties specific for a given antibody.

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains into close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding.

The terms, "antibody", is used herein in the broadest sense and specifically encompass monoclonal antibodies (including full length monoclonal antibodies), polyclonal antibodies, multispecific antibodies (e.g., bispecific antibodies), and antibody fragments such as variable domains and other portions of antibodies that exhibit a desired biological activity, e.g., WNV binding and or neutralizing.

The term "monoclonal antibody" (MAb) refers to an antibody of a population of substantially homogeneous antibodies; that is, the individual antibodies in that population are identical except for naturally occurring mutations that may be present in minor amounts. Monoclonal antibodies are highly specific, being directed against a single antigenic determinant, an "epitope". Therefore, the modifier "monoclonal" is indicative of a substantially homogeneous population of antibodies directed to the identical epitope and is not to be construed as requiring production of the antibody by any particular method. It should be understood that monoclonal antibodies can be made by any technique or methodology known in the art; including e.g., the hybridoma method (Kohler et al., 1975, Nature 256:495), or recombinant DNA methods known in the art (see, e.g., U.S. Pat. No. 4,816,567), or methods of isolation of monoclonal recombinantly produced using phage antibody libraries, using techniques described in Clackson et al., 1991, Nature 352: 624-628, and Marks et al., 1991, J. Mol. Biol. 222: 581-597.

Chimeric antibodies consist of the heavy and light chain variable regions of an antibody from one species (e.g., a non-human mammal such as a mouse) and the heavy and light chain constant regions of another species (e.g., human) antibody and can be obtained by linking the DNA sequences encoding the variable regions of the antibody from the first species (e.g., mouse) to the DNA sequences for the constant regions of the antibody from the second (e.g., human) species and transforming a host with an expression vector containing the linked sequences to allow it to produce a chimeric antibody. Alternatively, the chimeric antibody also could be one in which one or more regions or domains of the heavy and/or light chain is identical with, homologous to, or a variant of the corresponding sequence in a monoclonal antibody from another immunoglobulin class or isotype, or from a consensus sequence. Chimeric antibodies can include fragments of such antibodies, provided that the antibody fragment exhibits the desired biological activity of its parent antibody, for example binding to the same epitope (see, e.g., U.S. Pat. No. 4,816,567; and Morrison et al., 1984, Proc. Natl. Acad. Sci. USA 81: 6851-6855).

The methods of the invention can also be used to prepare antibody fragments. The term "antibody fragment" refers to a portion of a full length antibody, in which a variable region or a functional capability is retained, for example, specific West Nile Virus epitope binding. Examples of antibody fragments include, but are not limited to, a Fab, Fab', F(ab')2, Fd, Fv, scFv and scFv-Fc fragment, a diabody, a linear antibody, a single-chain antibody, a minibody, a diabody formed from antibody fragments, and multispecific antibodies formed from antibody fragments.

Full length antibodies can be treated with enzymes such as papain or pepsin to generate useful antibody fragments. Papain digestion is used to produces two identical antigen-binding antibody fragments called "Fab" fragments, each with a single antigen-binding site, and a residual "Fc" fragment. The Fab fragment also contains the constant domain of the light chain and the CH1 domain of the heavy chain. Pepsin treatment yields a F(ab')2 fragment that has two antigen-binding sites and is still capable of cross-linking antigen.

Fab' fragments differ from Fab fragments by the presence of additional residues including one or more cysteines from the antibody hinge region at the C-terminus of the CH1 domain. F(ab')2 antibody fragments are pairs of Fab' fragments linked by cysteine residues in the hinge region. Other chemical couplings of antibody fragments are also known.

"Fv" fragment is contains a complete antigen-recognition and binding site consisting of a dimer of one heavy and one light chain variable domain in tight, non-covalent association. In this configuration, the three CDRs of each variable domain interact to define an antigen-biding site on the surface of the VH-VL dimer. Collectively, the six CDRs confer antigen-binding specificity to the antibody.

A "single-chain Fv" or "scFv" antibody fragment is a single chain Fv variant comprising the VH and VL domains of an antibody where the domains are present in a single polypeptide chain. The single chain Fv is capable of recognizing and binding antigen. The scFv polypeptide may optionally also contain a polypeptide linker positioned between the VH and VL domains in order to facilitate formation of a desired three-dimensional structure for antigen binding by the scFv (see, e.g., Pluckthun, 1994, In The Pharmacology of monoclonal Antibodies, Vol. 113, Rosenburg and Moore eds., Springer-Verlag, New York, pp. 269-315).

Other recognized antibody fragments include those that comprise a pair of tandem Fd segments (VH-CH1-VH-CH1) to form a pair of antigen binding regions. These "linear antibodies" can be bispecific or monospecific as described in, for example, Zapata et al. 1995, Protein Eng. 8(10):1057-1062.

Any of the above antibody fragments or variants can be produced by the methods described herein and isolated for use as therapeutic and or prophylactic medicaments. As such, the antibody compositions of the invention may advantageously be prepared as pharmaceutical formulations in suitable pharmaceutical excipients or deliver vehicles. The antibody formulations will be prepared by at least one purification step in which the recombinant cellular material is removed. The methods described below are scaleable for the production of large quantities of the huE16 antibody for therapeutic and or prophylactic uses against WNV infection.

Example

Generation and Analysis of Novel Plant-Derived Antibody-Based Therapeutic Molecules Against West Nile Virus and Dengue Virus Previously, a plant-derived monoclonal antibody (MAb) (pHu-E16) was engineered that efficiently treated West Nile virus (WNV) infection in mice. In this study, a plant-derived MAb against dengue virus (DENY, pE60) was engineered. Several pHu-E16 and pE60 variants were also developed to improve its efficacy. These variants included a single-chain variable fragment (scFv) of pHu-E16 fused to the heavy chain (HC) constant domains ($C_H^{1-3}$) of human IgG (pHu-E16scFv-$C_H^{1-3}$) and a tetravalent molecule (Tetra pHu-E16) assembled from pHu-E16scFv-$C_H^{1-3}$ with a second pHu-E16scFv fused to the light chain (LC) constant region. pE60, pHu-E16scFv-$C_H^{1-3}$ and Tetra pHu-E16 were efficiently expressed and assembled in Wild-type (WT) and glycoengineered plants. To assess the impact of differences in N-linked glycosylation on pHu-E16 variant assembly and function, additional pHu-E16 variants were expressed with various combinations of HC and LC components. The study revealed that proper pairing of HC and LC was essential for the complete N-glycan processing of antibodies in both plant and animal cells. Associated with their distinct N-glycoforms, pHu-E16, pHu-E16scFv-$C_H^{1-3}$ and Tetra pHu-E16 exhibited differential binding to C1q and specific Fc receptors (FcγR). Notably, none of the plant-derived Hu-E16 variants showed antibody-dependent enhancement (ADE) activity in $CD32A^+$ cells, suggesting the potential of plant-produced antibodies to minimize the adverse effect of ADE. Importantly, all plant-derived MAb variants exhibited at least equivalent in vitro neutralization and in vivo protection in mice compared to mammalian cell-produced Hu-E16 or E60. This study demonstrates the capacity of plants to express and assemble a large, complex and functional IgG-like tetravalent mAb variant and also provides insight into the relationship between MAb N-glycosylation, FcγR and C1q binding, and ADE. These new insights may allow the development of safer and cost effective MAb-based therapeutics for flaviviruses.

West Nile virus (WNV) is a neurotropic virus that infects the central nervous system (CNS) of human and animals. Historically, WNV was an Old World disease found mostly in the Eastern Europe, Africa, and the Middle East. However, in 1999, WNV entered the Western hemisphere and subsequently spread across the United States (US), Canada, the Caribbean region and Latin America (Petersen, et al. (2013). "West Nile virus: review of the literature." *Jama* 310(3): 308-315). In the US, the frequency and severity of WNV outbreaks have increased significantly in recent years with 2012 as the deadliest (286 fatalities) on record. Elderly and immunocompromised humans are the most vulnerable for developing severe neurological disease, long-term morbidity, and death (Bode, A. V., J. J. Sejvar, et al. (2006). "West Nile virus disease: a descriptive study of 228 patients hospitalized in a 4-county region of Colorado in 2003." Clinical Infectious Diseases 42(9): 1234-40), although genetic factors also are associated with an increased risk of disease. Currently, there is no vaccine or therapeutic approved for human use. The global threat of WNV epidemics and the lack of treatment warrant the development of antiviral therapeutics and production platforms that can expeditiously bring products to market at low cost. A plant-derived, humanized murine MAb (pHu-E16) that binds to an epitope on domain III (DIII) of WNV envelope (E) protein was previously reported, as a post-exposure therapeutic candidate for WNV (Lai H, Engle M, Fuchs A, Keller T, Johnson S, et al. (2010) Monoclonal antibody produced in plants efficiently treats West Nile virus infection in mice. Proceedings of the National Academy of Sciences of the United States of America 107: 2419-2424). It was demonstrated that pHu-E16 was produced at high levels and assembled efficiently in both *Nicotiana benthamiana* and lettuce plants (Lai H, Engle M, Fuchs A, Keller T, Johnson S, et al. (2010) Monoclonal antibody produced in plants efficiently treats West Nile virus infection in mice. Proceedings of the National Academy of Sciences of the United States of America 107: 2419-2424; Lai H, He J, Engle M, Diamond M S, Chen Q (2012) Robust production of virus-like particles and monoclonal antibodies with geminiviral replicon vectors in lettuce. Plant Biotechnology Journal 10: 95-104). pHu-E16 also retained antigen binding specificity and affinity, and neutralized WNV infection equivalently relative to the mammalian cell-produced Hu-E16 (mHu-E16). Furthermore, pHu-E16 also protected mice from WNV infection and mortality equivalently compared to mHu-E16 in both pre- and post-exposure treatment models. Because WNV is a neurotropic virus, peripheral delivery of pHu-E16, however, likely will have a limited window of efficacy due to its inability to efficiently cross the blood brain barrier (BBB) and accumulate in the brain at concentrations sufficient for neutralization. Thus, it would be desirable to develop pHu-E16 variants, such as bifunctional MAbs, that can cross the BBB while retaining targeted therapeutic activity.

To test the ability of plants in producing such complex MAb variants, several pHu-E16 derivatives were expressed including a pHu-E16scFv fused to the heavy chain (HC) constant domains ($C_H^{1-3}$) of human IgG (pHu-E16scFv-$C_H^{1-3}$) and a large tetravalent molecule (Tetra pHu-E16) assembled from pHu-E16scFv-$C_H^{1-3}$ with another pHu-E16scFv fused to the light chain (LC) constant region ($C_L$) (pHu-E16scFv-$C_L$). It was demonstrated that plants can express and assemble these pHu-E16 variants efficiently. These pHu-E16 variants also showed at least equivalent protection as the parent pHu-E16 or mHu-E16 against a lethal WNV challenge in a mouse model. The results also revealed differences in N-linked glycosylation pattern between different MAb variants, and demonstrated that the proper pairing of HC and LC was essential for the complete N-glycan processing of antibodies in both plant and animal cells. It was also found that pHu-E16, pHu-E16scFv-$C_H^{1-3}$ and Tetra pHu-E16 exhibited differential binding to specific Fc receptors (FcγRs) and C1q, the complement opsonin that activates the classical complement pathway C3 convertase. Furthermore, in K562 cells, none of the plant-derived Hu-E16 variants showed significant antibody-dependent enhancement (ADE) activity, a phenomenon that is a major impediment for developing MAb-based therapeutics against flaviviruses, such as the related Dengue virus. Overall, this study demonstrates the capacity of a plant to express and assemble efficiently a large and complex IgG-like tetravalent MAb biologic, which offers a step forward toward the development of bifunctional MAbs in plants. This study also contributes to the understanding of the basic biological process of antibody glycosylation, and the relationship between MAb N-linked glycosylation, FcγR and C1q binding, and ADE.

Results

Expression and Assembly of pHu-E16 scFv-$C_H^{1-3}$ in *N. Benthamiana*

Figure 2:
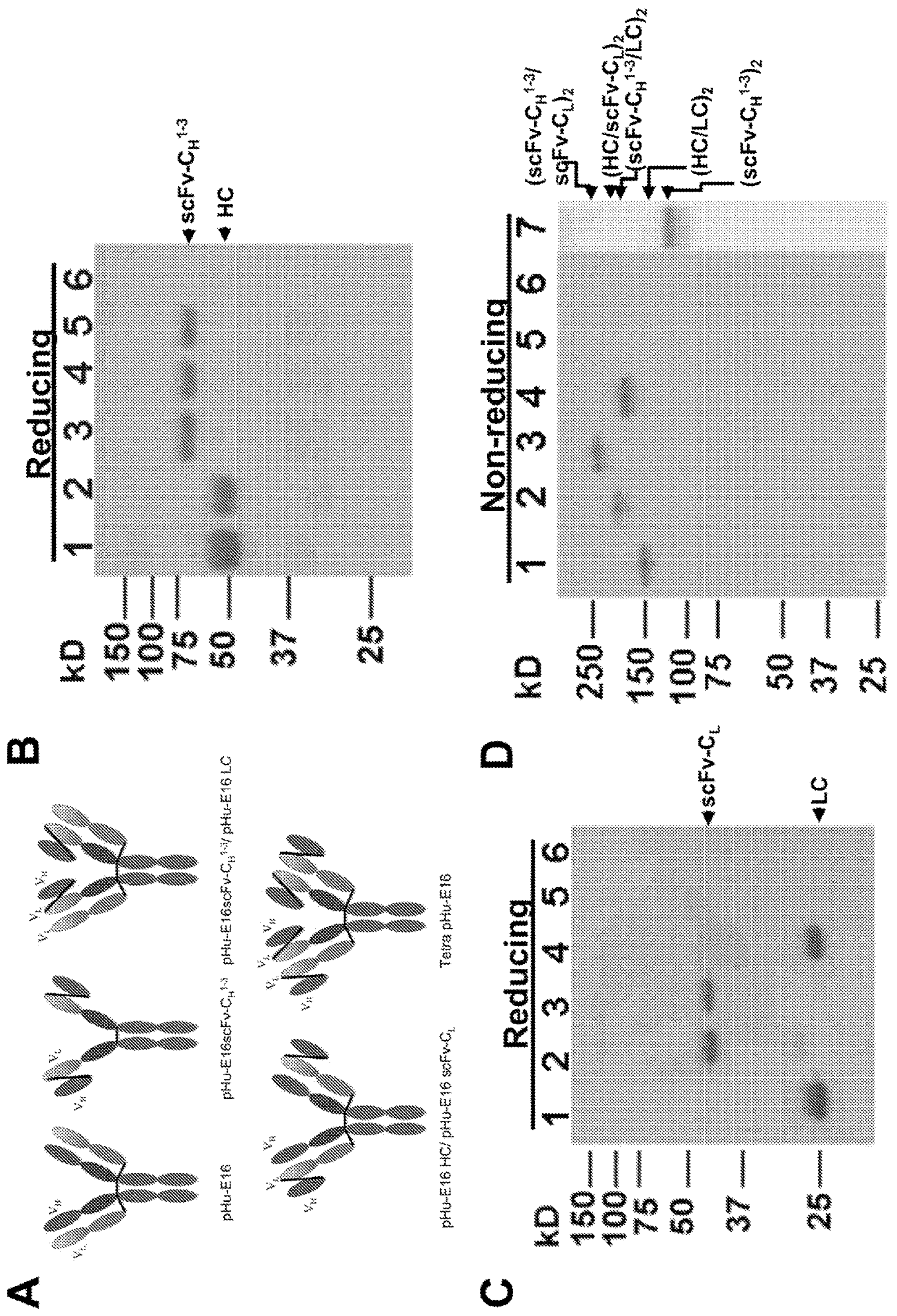
FIG. 2. Western blot analysis of pHu-E16 variants. A. Designs of Hu-E16 variants in this study. B-D. Western blot analysis. Hu-E16 variants were extracted from *N. benthamiana* leaves and were separated on SDS-PAGE gels under reducing (B and C) or non-reducing (D) conditions and blotted onto PVDF membranes. The membranes were incubated with a goat anti-human gamma chain antibody or a goat anti-human kappa chain antibody to detect heavy chain (B and Lane 7 of D) or light chain (C and Lanes 1-6 of D). Lane 1, pHu-E16 as a reference standard; lane 2, Protein sample extracted from leaves co-infiltrated with pHu-E16 HC and pHu-E16scFv-$C_L$ constructs; lane 3, Sample from leaves co-infiltrated with pHu-E16scFv-$C_H^{1-3}$ and pHu-E16scFv-$C_L$; lane 4, Sample from leaves co-infiltrated with pHu-E16scFv-$C_H^{1-3}$ and pHu-E16 LC; lanes 5 and 7, Sample from leaves infiltrated with pHu-E16scFv-$C_H^{13}$; lane 6, Sample from un-infiltrated leaves. HC: heavy chain, scFv: single-chain variable fragment; $C_H^{1-3}$: the constant region domains 1 to 3 of HC; LC: light chain; $C_L$: Constant region of LC; $V_L$: variable region of LC; $V_H$: variable region of HC.
Figure 3:
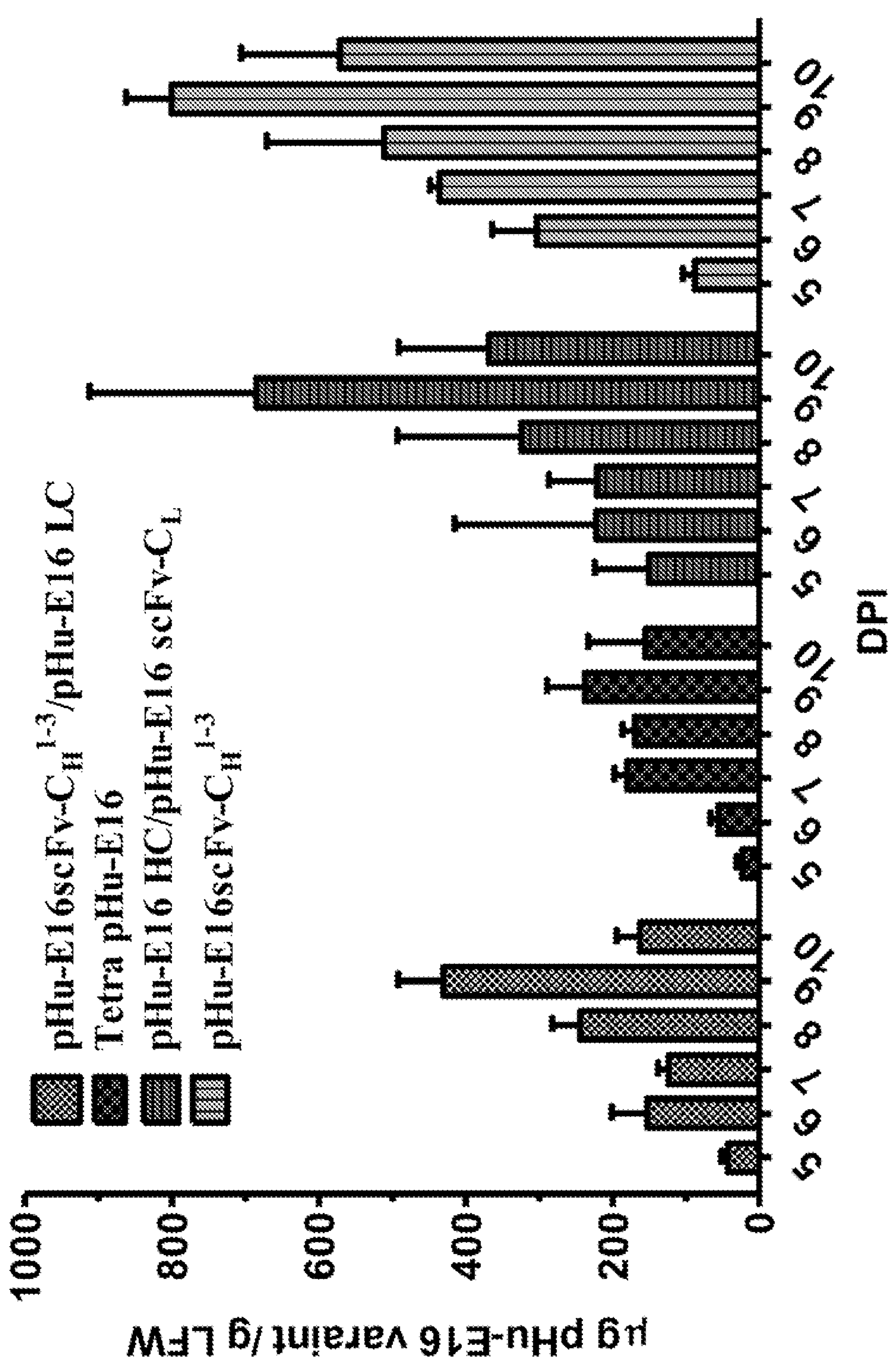
FIG. 3. Time course of pHu-E16 expression in *N. benthamiana* plants. Total proteins from leaves infiltrated or co-infiltrated with pHu-E16scFv-$C_H^{1-3}$, pHu-E16 HC/pHu-E16scFv-$C_L$, pHu-E16scFv-$C_H^{1-3}$pHu-E16scFv-$C_L$ (Tetra pHu-E16), or pHu-E16scFv-$C_H^{1-3}$/pHu-E16 LC were extracted on days 5-10 post infiltration and analyzed by ELISA that detects the assembled form of pHu-E16 MAb variants, Mean±SD of samples from three independent infiltrations are presented.

An important prerequisite for the generation of bifunctional Hu-E16 MAb is the correct assembly of its functional component: pHu-E16scFv-$C_H^{1-3}$. The DNA sequence of the variable region of HC ($V_H$) and LC ($V_L$) of pHu-E16 (Lai H, Engle M, Fuchs A, Keller T, Johnson S, et al. (2010) Monoclonal antibody produced in plants efficiently treats West Nile virus infection in mice. Proceedings of the National Academy of Sciences of the United States of America 107: 2419-2424) was fused together first to generate pHu-E16scFv, and then fused to the coding sequence of the $C_H^{1-3}$ of human IgG (FIG. 2A). The resulting coding sequence of pHu-E16scFv-$C_H^{1-3}$ was cloned into a MagnICON-based plant expression vector (Giritch A, Marillonnet S, Engler C, van Eldik G, Botterman J, et al. (2006) Rapid high-yield expression of full-size IgG antibodies in plants coinfected with noncompeting viral vectors. Proceedings of the National Academy of Sciences of the United States of America 103: 14701-14706), and transformed into *Agrobacterium tumefacient. A. tumefacient* strains containing the pHu-E16scFv-$C_H^{1-3}$ construct were co-delivered into *N. benthamiana* leaves along with the promoter module and an integrase construct through agroinfiltration (Leuzinger K, Dent M, Hurtado J, Stahnke J, Lai H, et al. (2013) Efficient Agroinfiltration of Plants for High-level Transient Expression of Recombinant Proteins. Journal of Visualized Experiments: doi:10.3791/50521; Chen Q, Lai H, Hurtado J, Stahnke J, Leuzinger K, et al. (2013) Agroinfiltration as an Effective and Scalable Strategy of Gene Delivery for Production of Pharmaceutical Proteins. Adv Tech Biol Med 1: 9). Western blot analysis after reducing or non-reducing gel electrophoresis confirmed that pHu-E16scFv-$C_H^{1-3}$ was produced in leaves with the expected molecular weight (FIG. 2B, Lane 5), and that it assembled into a dimer (FIG. 2D, Lane 7). ELISA results also indicated that pHu-E16scFv-$CH^{1-3}$ reached the highest level of accumulation 9 days post infiltration (dpi) with *A. tumefacient*, with an average accumulation of 0.8 mg/g leaf fresh weight (LFW) (FIG. 3). This level is similar that of the parent pHu-E16 MAb was reported previously, which is among the highest expression levels for MAbs in plants ever reported (De Muynck B, Navarre C, Boutry M (2010) Production of antibodies in plants: status after twenty years. Plant Biotechnology Journal 8: 529-563; Lai H, Engle M, Fuchs A, Keller T, Johnson S, et al. (2010) Monoclonal antibody produced in plants efficiently treats West Nile virus infection in mice. Proceedings of the National Academy of Sciences of the United States of America 107: 2419-2424; Bendandi M, Marillonnet S, Kandzia R, Thieme F, Nickstadt A, et al. (2010) Rapid, high-yield production in plants of individualized idiotype vaccines for non-Hodgkin's lymphoma. Annals of Oncology 21: 2420-2427). Similar expression pattern and level was observed when pHu-E16scFv-$CH^{1-3}$ was expressed in a glycoengineered ΔXF *N. benthamiana* line which decorates proteins with mammalian type GnGn glycans (He, et al. (2014). "Generation and Analysis of Novel Plant-Derived Antibody-Based Therapeutic Molecules against West Nile Virus." *PLoS ONE* 9(3): e93541 DOI:93510.91371/journal-.pone.0093541; Lai, et al. (2014). "Structural and functional characterization of an anti-West Nile virus monoclonal antibody and its single-chain variant produced in glycoengineered plants." *Plant Biotechnology Journal* 12(8): 1098-1107.

E60 mAb Expression and Assembly in *N. benthamiana*

Figure 9:
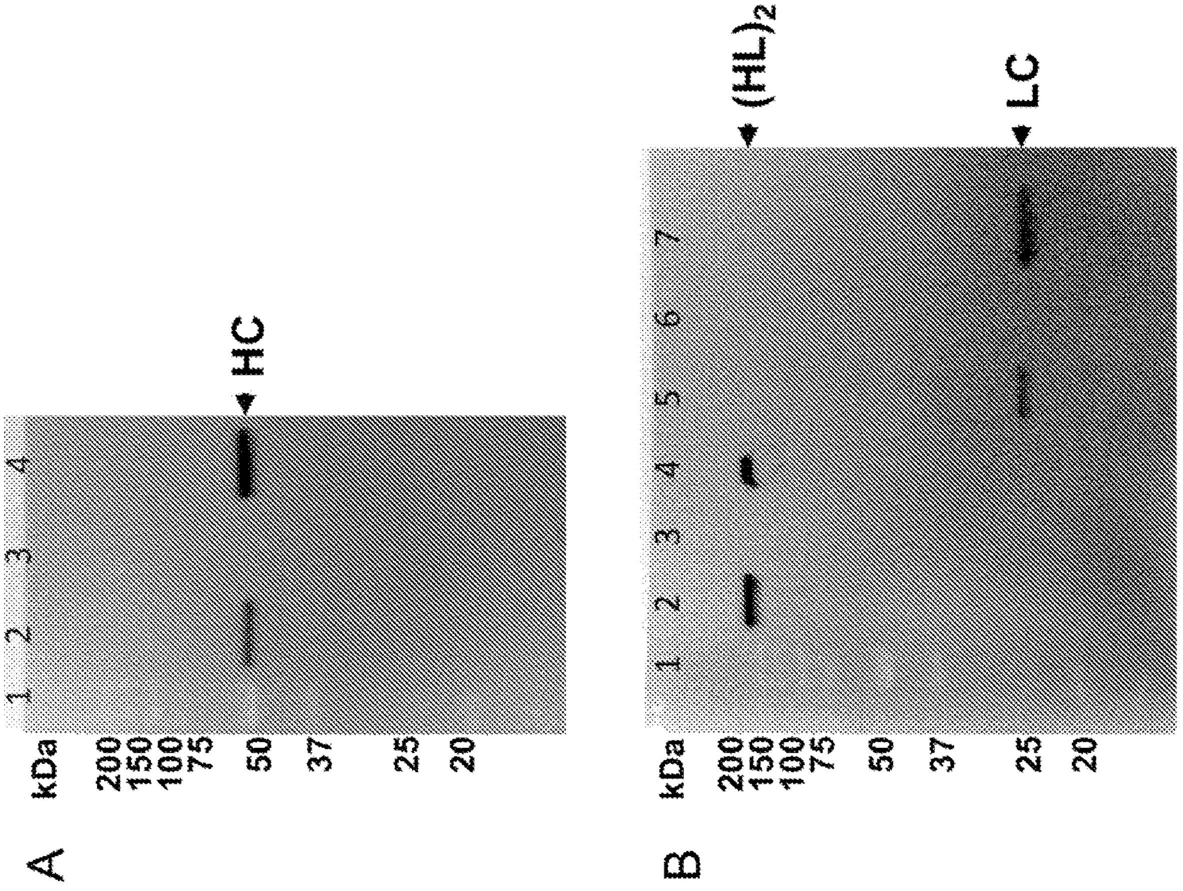
FIG. 9. Western blot analysis of pE60. pE60 was extracted from *N. benthamiana* leaves and were separated on SDS-PAGE gels under reducing (A and B lanes 5-6) or non-reducing (B lanes 2-4) conditions and blotted onto PVDF membranes. The membranes were incubated with a goat anti-human gamma chain antibody or a goat anti-human kappa chain antibody to detect heavy chain (A) or light chain (B). Lane 1, Molecular weight marker; lanes 2 and 5, Mammalian cell-produced E60 as a reference standard; lanes 3 and 6, Protein sample extracted from leaves infiltrated with buffer as a negative control; lanes 4 and 7, Sample from leaves co-infiltrated with E60 LC and E60 HC. HC: heavy chain, LC: light chain, $(HL)_2$: assembled tetrameric form of E60 antibody.

Gel electrophoresis (SDS-PAGE) and western blot were used to determine the ability of WT and ΔXF *N. benthamiana* plants in expressing and assembling E60 mAb in their cells. ΔXF is a *N. benthamiana* N-glycosylation mutant that produces glycoproteins with the mammalian-type GnGn glycan structure due to the inactivation of enzymes for plant-specific xylose and core fucose residues (Strasser et al. 2008). Western blot analysis of reduced samples indicated that E60 was expressed in WT plants with the expected molecular weight of HC (50 kDa) and LC (25 kDa) (FIG. 9). Results from non-reduced samples confirmed that HC and LC had assembled into the expected tetrameric full antibody (FIG. 9). Similar to the positive control mAb, the assembled E60 was detected as a band larger than the calculated size (150 kDa), suggesting its possible glycosylation. The expression and assembly of E60 in ΔXF plants have also been demonstrated with equivalent results (data not shown). The temporal expression pattern of E60 in plants was monitored by ELISA, indicating that the expression pattern of E60 is similar to what was observed for several mAb variants against WNV in *N. benthamiana* (He, et al. (2014). "Generation and Analysis of Novel Plant-Derived Antibody-Based Therapeutic Molecules against West Nile Virus." *PLoS ONE* 9(3): e93541 DOI:93510.91371/journal-.pone.0093541; Lai H, Engle M, Fuchs A, Keller T, Johnson S, et al. (2010) Monoclonal antibody produced in plants efficiently treats West Nile virus infection in mice. Proceedings of the National Academy of Sciences of the United States of America 107: 2419-2424; Lai, et al. (2014). "Structural and functional characterization of an anti-West Nile virus monoclonal antibody and its single-chain variant produced in glycoengineered plants." *Plant Biotechnology Journal* 12(8): 1098-1107).

Plant-Derived pHu-E16 Exhibited a Highly Homogeneous Gglycosylation Pattern pHu-E16 was expressed in both WT and ΔXF *N. benthamiana* plant line. N-glycan profile analysis revealed that 90% of pHu-E16 produced in WT plants exhibited the expected GnGnXF glycoform (FIG. 16). pHu-E16 produced in ΔXF *N. benthamiana* plant line exhibited the expected mammalian-type complex N-glycan GnGn with a high degree (~95%) of uniformity (FIG. 13A). Furthermore, no plant-specific glycan residues (i.e. β1,2-xylose and core α1,3-fucose) were detected in either ΔXF-expressed pHu-E16. Homogeneous glycans in plant-produced pHu-E16 should enhance the identification of glycoforms that reduced the risk of ADE while retaining the full therapeutic activity. In contrast, E16 produced in mammalian cells (mE16) displayed a mixture of several glycoforms (FIG. 13B and FIG. 16).

pHu-E16 scFv-$C_H^{1-3}$ Exhibited Altered N-Linked Glycosylation Pattern

A typical feature of IgG antibodies is a conserved N-glycosylation site at position $Asn^{297}$ in the $C_H^2$ domain and it is well documented that the pattern and extent of N-linked glycosylation affects the stability and function of an antibody (Houde D, Peng Y, Berkowitz S A, Engen J R (2010) Post-translational modifications differentially affect IgG1 conformation and receptor binding. Mol Cell Proteomics 9: 1716-1728). Accordingly, the N-glycoforms of pHu-E16scFv-$C_H^{1-3}$ were next examined by liquid-chromatography-electrospray ionization-mass spectrometry (LC-ESI-MS) to assess whether the extent N-linked glycosylation was similar to the parent pHu-E16. pHu-E16 exhibited the expected complex-type N-glycans (GnGnXF, FIG. 16), typical for plant-produced IgGs (Loos A, Steinkellner H (2012) IgG-Fc glycoengineering in non-mammalian expression hosts. Arch Biochem Biophys 526: 167-173). However, pHu-E16scFv-$C_H^{1-3}$ displayed oligomannosidic structures, predominantly Man8 and Man9 (FIG. 16). The predominantly endoplasmic reticulum (ER)-type N-glycans of pHu-E16scFv-$C_H^{1-3}$ were unexpected, as this molecule was targeted for secretion and not tagged with an ER-retention signal KDEL (SEQ ID NO:8). To investigate if this is a phenomenon specific to plant cells, the N-glycan profiles of equivalent Hu-E16 variants produced in mammalian cells (mHu-E16 and mHu-E16scFv-$C_H^{1-3}$) were also compared. A substantial amount of oligomannosidic glycans (oligoman, mostly M5 and M7) in mHu-E16scFv-$C_H^{1-3}$ were observed, in addition to the predominant complex-type glycans ($GnGnF^6$ and $AGnF^6$), whereas no such glycans were observed in mHu-E16 (FIG. 16). This result suggests that the unusual N-linked glycosylation pattern of scFv-$C_H^{1-3}$ is not unique to plants but also is shared by mammalian cells, even though the percentage and the particular species of oligomannosidic glycans differ between cells from the two species.

Expression and N-linked Glycosylation of a Tetravalent pHu-E16 and Other pHu-E16 Variants The success of pHu-E16 scFv-$C_H^{1-3}$ expression and assembly in plants indicates the feasibility of developing an IgG-like tetravalent MAb variant. Such novel form of anti-WNV therapeutics either can provide four WNV antigen-binding sites or function as a bifunctional MAbs that offer divalent binding to two different antigens. For example, a bifunctional MAbs could be engineered to bind a BBB receptor as its second antigen to enhance its transport into the brain, extending the window of treatment for WNV infection. Thus, to understand the basis of the difference in N-linked glycans between pHu-E16scFv-$C_H^{1-3}$ and its parent pHu-E16 and develop a potentially more efficacious WNV therapeutic, three additional pHu-E16 variants with various combinations of HC and LC components were engineered an expressed. First, pHu-E16scFv was fused to the plant-codon optimized $C_L$ (pHu-E16scFv-$C_L$). Three pHu-E16 variants were then produced in *N. benthamiana* plants by the co-expression of the following Hu-E16 construct combinations: scFv-$CH^{1-3}$/LC, HC/scFv-$C_L$, and scFv-$C_H^{1-3}$/scFv-$C_L$ (FIG. 2A). Western blot analysis after reducing gel electrophoresis confirmed that each component of the variants was produced in plants with the expected molecular weight (FIGS. 2B and C, Lanes 2-4). These protein bands are specific to the infiltrated molecular constructs, as they were not detected in samples from negative control plant leaves (FIGS. 2B and C, Lane 6). Moreover, western blotting after non-reducing gel electrophoresis reveals that the two polypeptides in each combination assembled into an IgG-like heterotetramer (FIG. 2D, Lanes 2-4 and FIG. 2A). The successful expression and assembly of pHu-E16scFv-$C_H^{1-3}$ with pHu-E16scFv-$C_L$ to form a tetravalent molecule (Tetra pHu-E16, FIG. 2B-D, Lane 3, and FIG. 1A) in plants is noteworthy, as the assembly of such large and complex MAb variants has not been reported previously. Yield analysis by ELISA established that Tetra pHu-E16 and other variants reached the highest level of production at 9 dpi. Nonetheless, the expression level varied between the three pHu-E16 variants, with HC/scFv-$C_L$'s comparable to that of the parent pHu-E16 and pHu-E16scFv-$C_H^{1-3}$ (0.69 mg/g LFW), scFv-$CH^{1-3}$/LC's at 0.43 mg/g LFW, and Tetra pHu-E16 at 0.24 mg/g LFW (FIG. 3).

In addition to developing a tetravalent pHu-E16 as a possible novel WNV therapeutic molecule, the expression of the three pHu-E16 variants also allowed the cause of the unexpected N-linked glycosylation of pHu-E16scFv-$C_H^{1-3}$ to be studied, specifically to address whether LC or the proper pairing of HC and LC affected N-linked glycosylation of MAb and its variants. Co-expression of LC of pHu-E16 significantly increased the percentage of complex-type glycans in pHu-E16scFv-$C_H^{1-3}$ (FIG. 16). In Tetra pHu-E16, the co-expression and pairing of scFv-$C_H^{1-3}$/scFv-$C_L$ also increased the amount of complex-type N-glycans (FIG. 16), albeit not to the same level as in the scFv-$C_H^{1-3}$/LC combination. In contrast, pairing of the HC of pHu-E16 with scFv-$C_L$ yielded a predominantly complex-type N-linked glycosylation pattern, similar to that of the parent pHu-E16 (FIG. 16). These results indicated the importance of LC and its pairing with HC for the complete processing of N-linked glycans on antibodies.

Purification of pHu-E16 and pE60 Variants from *N. Benthamiana* Leaves

Figure 4:
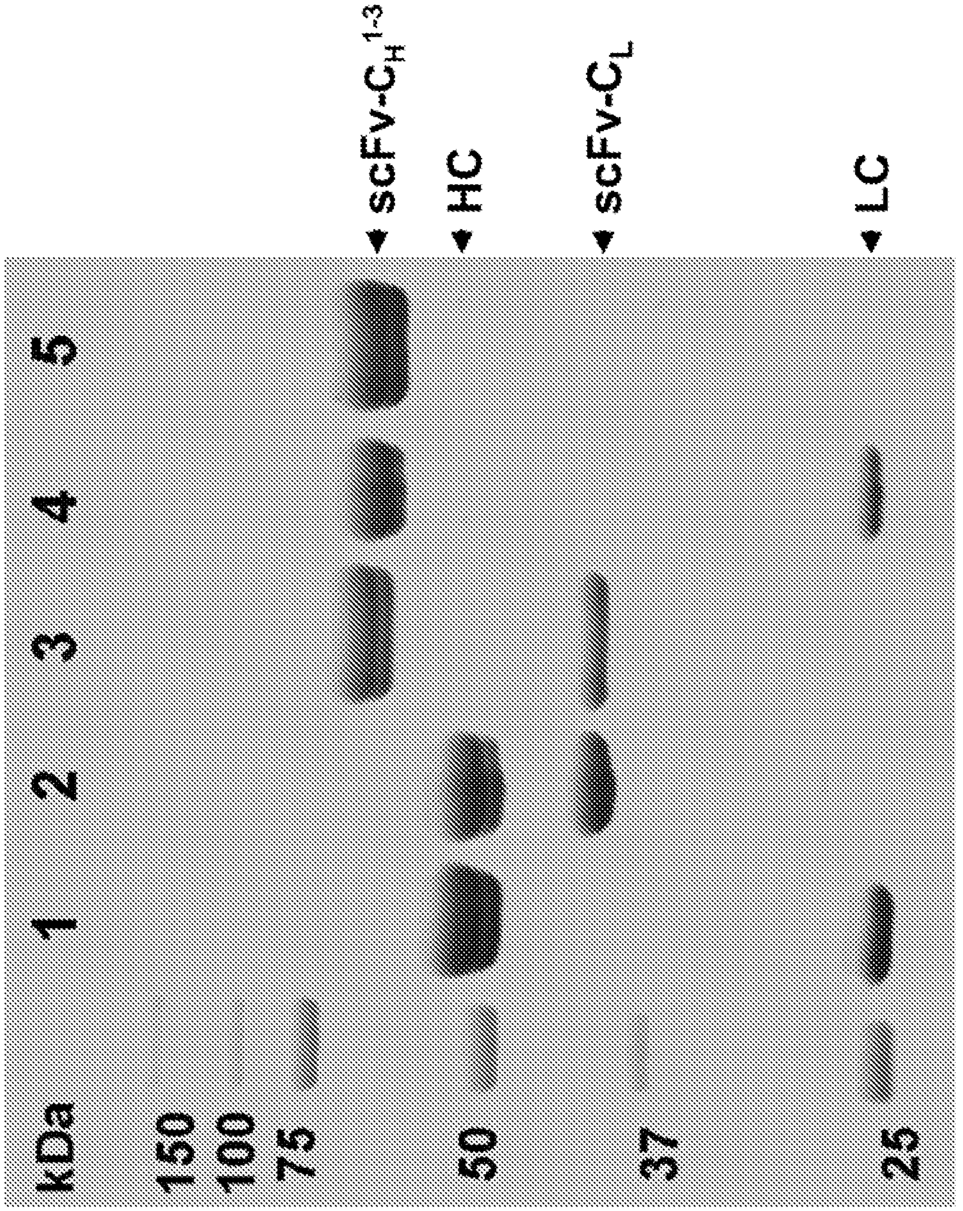
FIG. 4. Purification of pHu-E16 variants from *N. benthamiana* leaves. Leaf proteins were extracted on day 9 after agroinfiltration. pHu-E16 variants were purified and analyzed on a 4-20% gradient SDS-PAGE gel under reducing condition and visualized with Coomassie stain. Lane 1, pHu-E16 as a reference standard; lane 2, pHu-E16 HC/pHu-E16scFv-$C_L$; lane 3, Tetra pHu-E16; lane 4, pHu-E16scFv-$C_H^{1-3}$/pHu-E16 LC; lanes 5, pHu-E16scFv-$C_H^{1-3}$. One representative of several independent experiments is shown.
Figure 5:
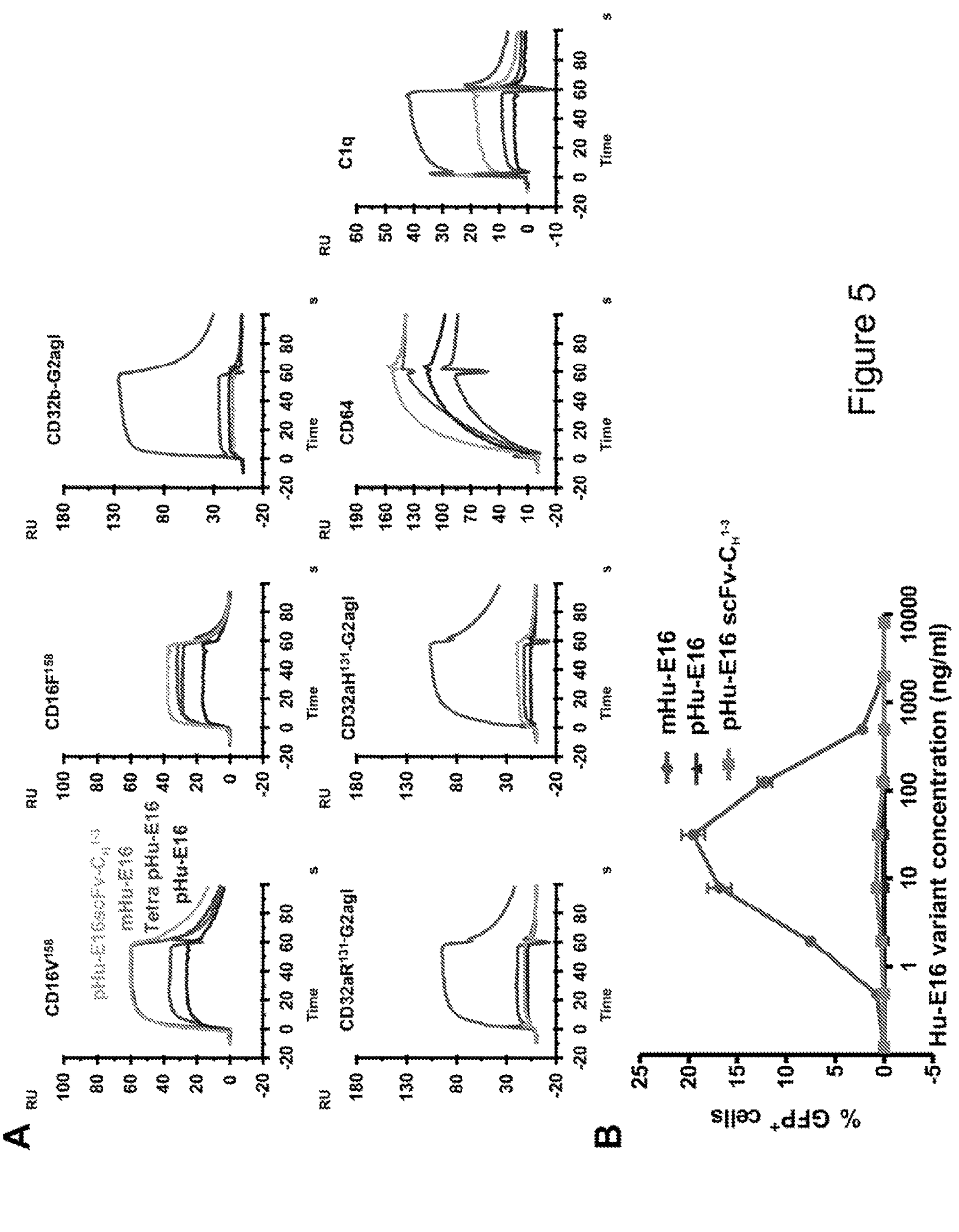
FIG. 5. FcγR and C1q binding and antibody-dependent enhancement of pHu-E16 variants. A. SPR analysis of FcγR and C1q binding. FcγRs including CD16A (CD16$V^{158}$, CD16$F^{158}$), CD32A (CD32a$R^{131}$ and CD32a$H^{131}$ fused to an aglycosylated Fc region of IgG2 (CD32a$R^{131}$-G2agl and CD32a$H^{131}$-G2agl)), CD32B (CD32b fused to an aglycosylated Fc region of IgG2 (CD32b-G2agl)) and CD64, and C1q were injected over the surfaces with Hu-E16 variants captured on immobilized WNV E protein. Buffer injection was subtracted as blank and responses were normalized to same level of captured antibodies. B. Hu-E16 variants antibody-dependent enhancement of WNV infection. Serial dilutions of Hu-E16 variants were mixed with WNV RVP and added to CD32A+K562 cells. Forty-eight hours later, cells were analyzed by flow cytometry for GFP expression.
Figure 10:
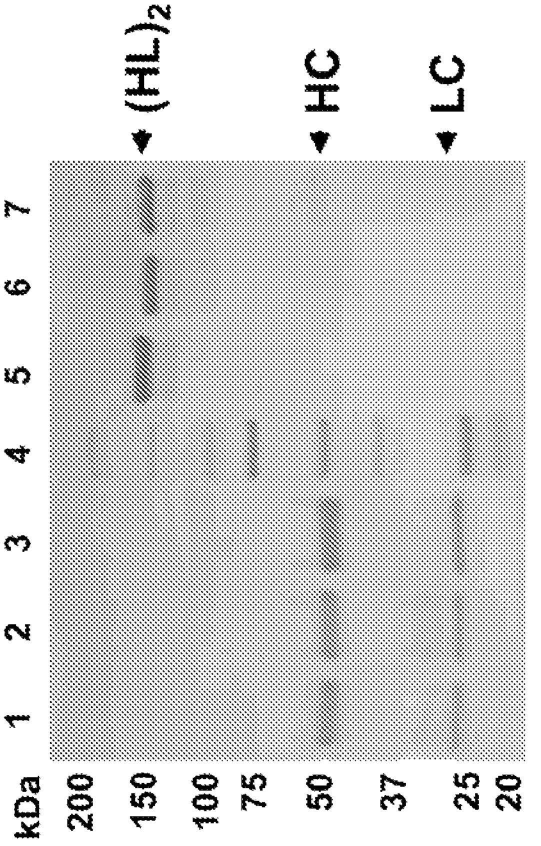
FIG. 10. Purification of E60 from *N. benthamiana* leaves. Leaf proteins were extracted from wild-type (Lanes 3 and 6) or GnGn (Lanes 2 and 7) *N. benthamiana* plants on day 9 after agroinfiltration. pE60 was purified and analyzed on a 4-20% gradient SDS-PAGE gel under reducing (Lanes 1-3) or non-reducing (Lanes 5-7) condition and visualized with Coomassie stain. Lanes 1 and 6, pE60 purified from WT plants; Lanes 2 and 7, pE60 purified from GnGn plants; Lanes 3 and 5, pHu-E16 as a reference standard. One representative of several independent experiments is shown.

For Tetra pHu-E16 and other variants and pE60 to be feasible therapeutic candidates for WNV and DENY, respectively, an efficient extraction and purification process must be developed and validated. A scalable extraction and purification process previously developed for pHu-E16 was applied to the purification of these variants (Lai H, Engle M, Fuchs A, Keller T, Johnson S, et al. (2010) Monoclonal antibody produced in plants efficiently treats West Nile virus infection in mice. Proceedings of the National Academy of Sciences of the United States of America 107: 2419-2424). Analysis of processing samples with gel electrophoresis indicate that in spite of their structural complexity, Tetra pHu-E16, pHu-E16scFv-$C_H^{1-3}$, pE60 and other variants were readily extracted from plant tissue and enriched to >90% purity by a combination of ammonium sulfate precipitation and protein A chromatography (FIG. 4 and FIG. 10). These purified pHu-E16 variants were used for the further functional characterization.

pHu-E16 Variants Show Differential Binding to Human Fcγ Receptors and C1q and Reduced Antibody-Dependent Enhancement Activity in K562 Cells N-linked glycosylation in the Fc region of an antibody affects binding to FcγRs and C1q (Houde D, Peng Y, Berkowitz S A, Engen J R (2010) Post-translational modifications differentially affect IgG1 conformation and receptor binding. Mol Cell Proteomics 9: 1716-1728). Accordingly, the binding of pHu-E16scFv-$C_H^{1-3}$ and Tetra pHu-E16 to C1q and different human FcγRs, including CD16A-$V^{158}$, CD16A-$F^{158}$, CD32A-$R^{131}$, CD32A-$H^{131}$, CD32B, and CD64, was investigated by surface plasmon resonance (SPR) analysis using pHu-E16 and mHu-E16 as references. Compared to mHu-E16, pHu-E16 showed reduced binding to all FcγRs and C1q (FIG. 5A). In comparison, pHu-E16scFv-$C_H^{1-3}$ showed slightly enhanced binding to CD64 and the low-affinity ($F^{158}$) isoform of CD16A, maintained similar binding to the high-affinity ($V^{158}$) CD16A isoform, and had reduced binding to CD32A and B (FIG. 5A). Tetra pHu-E16 showed a similar binding profile of FcγRs and C1q as pHu-E16scFv-$CH^{1-3}$, except with reduced binding to CD64 and the high affinity isoform ($V^{158}$) of CD16A (FIG. 5A).

The interaction between Fc moieties and FcγRs or C1q also regulates antibody-mediated enhancement of viral infections (ADE), a phenomenon that is relevant to disease pathogenesis of some flaviviruses (Morens D M (1994) Antibody-dependent of enhancement of infection and the pathogenesis of viral disease. Clin Inf Dis 19: 500-512; Halstead S B, Mahalingam S, Marovich M A, Ubol S, Mosser D M (2010) Intrinsic antibody-dependent enhancement of microbial infection in macrophages: disease regulation by immune complexes. Lancet Infect Dis 10: 712-722; Mehlhop E, Ansarah-Sobrinho C, Johnson S, Engle M, Fremont D H, et al. (2007) Complement protein C1q inhibits antibody-dependent enhancement of flavivirus infection in an IgG subclass-specific manner. Cell Host Microbe 2: 417-426). As such, it was investigated if plant-produced Hu-E16 variants would have a unique ADE profile in vitro compared to that of mHu-E16. Notably, all pHu-E16 variants lost their ADE activity in human K562 cells, which predominantly express CD32A, indicating the potential of plants to produce antibodies or antibody-like molecules that minimize ADE (FIG. 5B).

Antigen Binding and Neutralization Activity of pHu-E16 Variants and pE60

Figure 6:
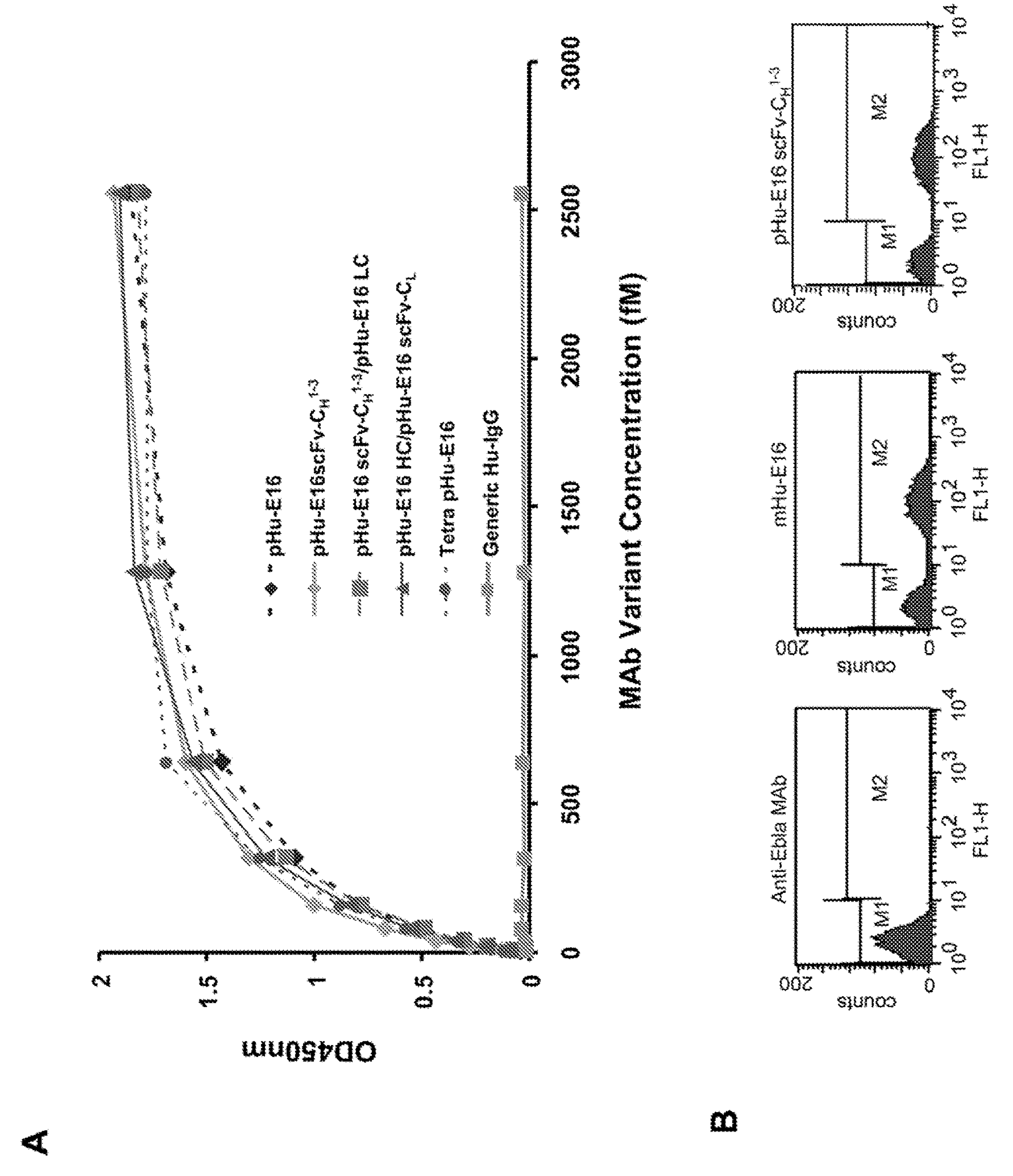
FIG. 6. Antigen binding of pHu-E16 variants to DIII of WNV E. A. ELISA analysis. Serial dilutions of pHu-E16 variants were incubated on plates coated with WNV DIII and detected with a HRP-conjugated anti-human gamma antibody. Dilutions of pHu-E16 were used in parallel as reference standards. A commercial generic human IgG (Southern Biotech) was used as a negative control. One set of representative O.D. 450 nm readings from several independent experiments is presented. B. Binding of pHu-E16scFv-$C_H^{1-3}$ to domain III of WNV E displayed on the cell surface of yeast. Yeast cells displaying domain III of WNV E protein were stained with pHu-E16scFv-$C_H^{1-3}$, mHu-E16 (positive control), or a plant-produced humanized MAb against Ebola virus GP1 protein (negative control). Yeast cells were then processed by flow cytometry. Representative data from three independent experiments are shown.
Figure 11:
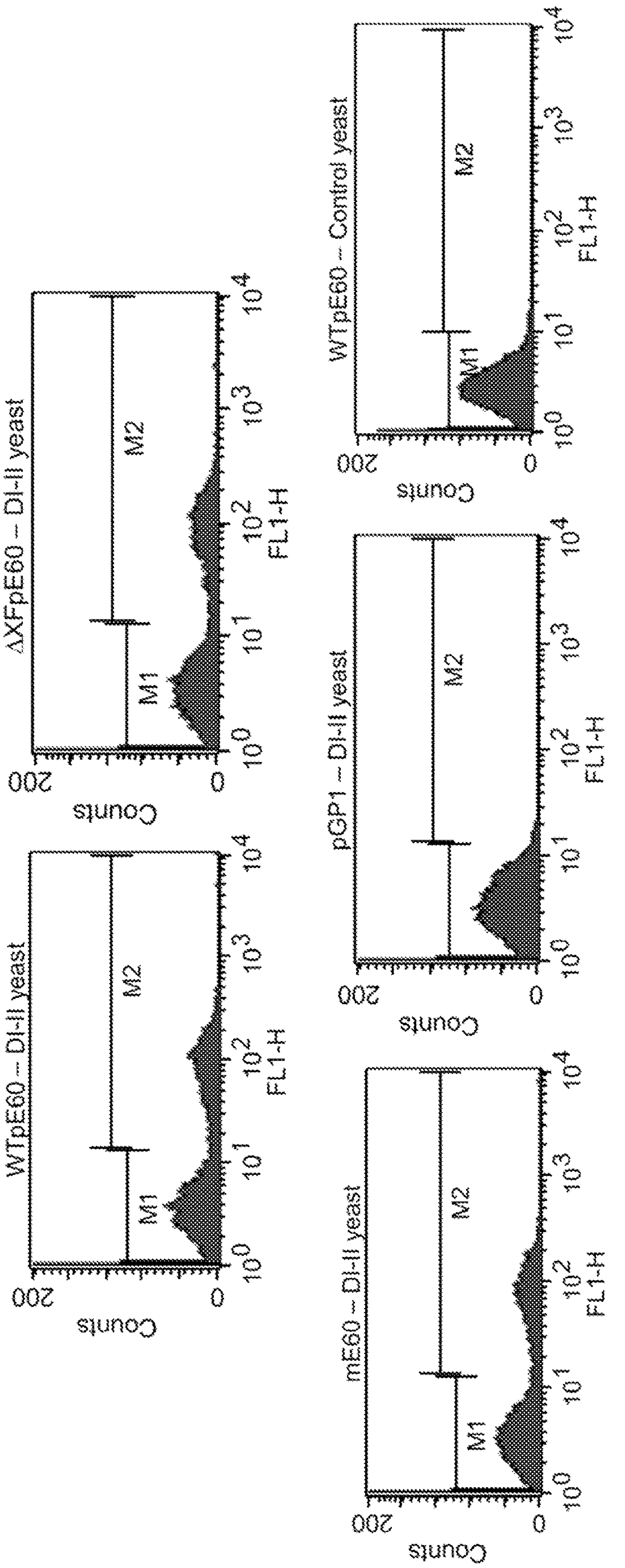
FIG. 11. Binding of plant-derived E60 to domain II of WNV E displayed on the cell surface of yeast. Negative control yeast and yeast cells displaying domain I-II of DENV E protein were stained with E60 from WT *N. benthamiana* plants (WTpE60), GnGn *N. benthamiana* plants (ΔXFpE60), Mammalian cells (mE60, positive control), or pGP1 (negative control). Yeast cells were then processed by flow cytometry. Representative data from at least three independent experiments are shown.

The binding kinetics and function of pHu-E16 variants was also assessed in several assays. The binding of pHu-E16 variants to WNV E DIII was determined by ELISA in which DIII was coated on the plate (Lai H, Engle M, Fuchs A, Keller T, Johnson S, et al. (2010) Monoclonal antibody produced in plants efficiently treats West Nile virus infection in mice. Proceedings of the National Academy of Sciences of the United States of America 107: 2419-2424). E16scFv-$C_H^{1-3}$, Tetra pHu-E16 and other pHu-E16 variants bound in a similar manner to DIII as pHu-E16 (FIG. 6A). Recognition of pHu-E16 variants for DIII was corroborated in a binding assay with yeast that displayed DIII on their surface. Flow cytometric analysis showed that the percentage of positive yeast and the mean fluorescence intensity of binding by saturating concentrations of pHu-E16scFv-$C_H^{1-3}$ and mHu-E16 were similar (FIG. 6B). Similar results were obtained for Tetra pHu-E16 and other variants (data not shown). For the DENV therapeutic candidate of pE60, flow cytometric analysis demonstrated that plant-derived pE60 exhibited similar antigen (DENY DI-II) binding specificity as its mammalian-produced counterpart (FIG. 11). The binding of these variants to WNV E DIII was quantitated by a SPR assay; as expected, E16scFv-$C_H^{1-3}$ and Tetra pHu-E16 had similar binding affinity and kinetics for WNV E protein and DIII compared to its parent mHu-E16 with KD=10 to 25 nM. These results confirm that E16scFv-$C_H^{1-3}$ and Tetra pHu-E16 retain antigen binding activity and specificity compared to pHu-E16 and mHu-E16.

Figure 7:
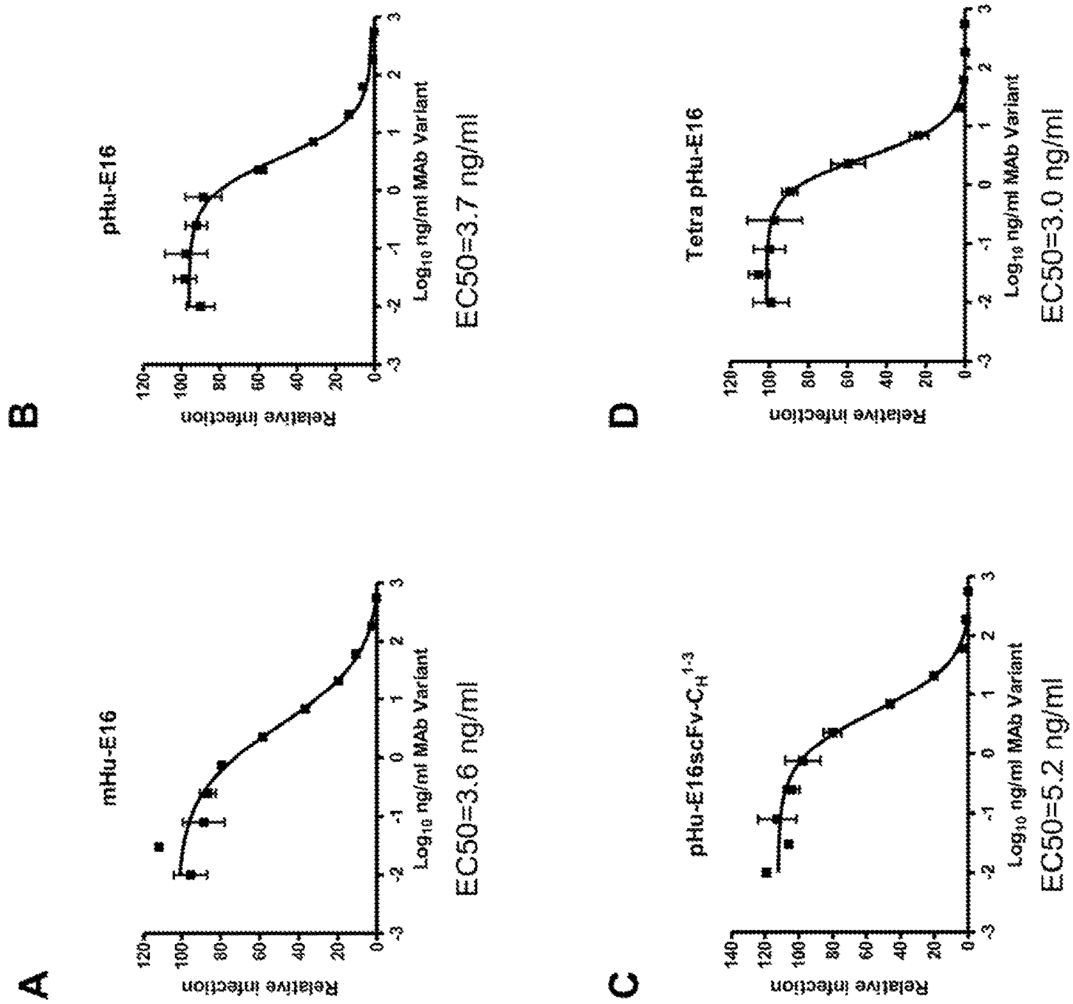
FIG. 7. Neutralization of WNV by pHu-E16 variants. WNV (strain New York 1999) was incubated with serial dilutions of A) mHu-E16 (positive control 1), or B) pHu-E16 (positive control 2), C) pHu-E16scFv-$C_H^{1-3}$, or D) Tetra pHu-E16 and used to infect Vero cells. Cells were then fixed, permeabilized, analyzed by focus reduction assay and quantitated by Biospot analysis. Mean±SEM is shown from one of several independent experiments. EC50 values are listed below the graphs.
Figure 12:
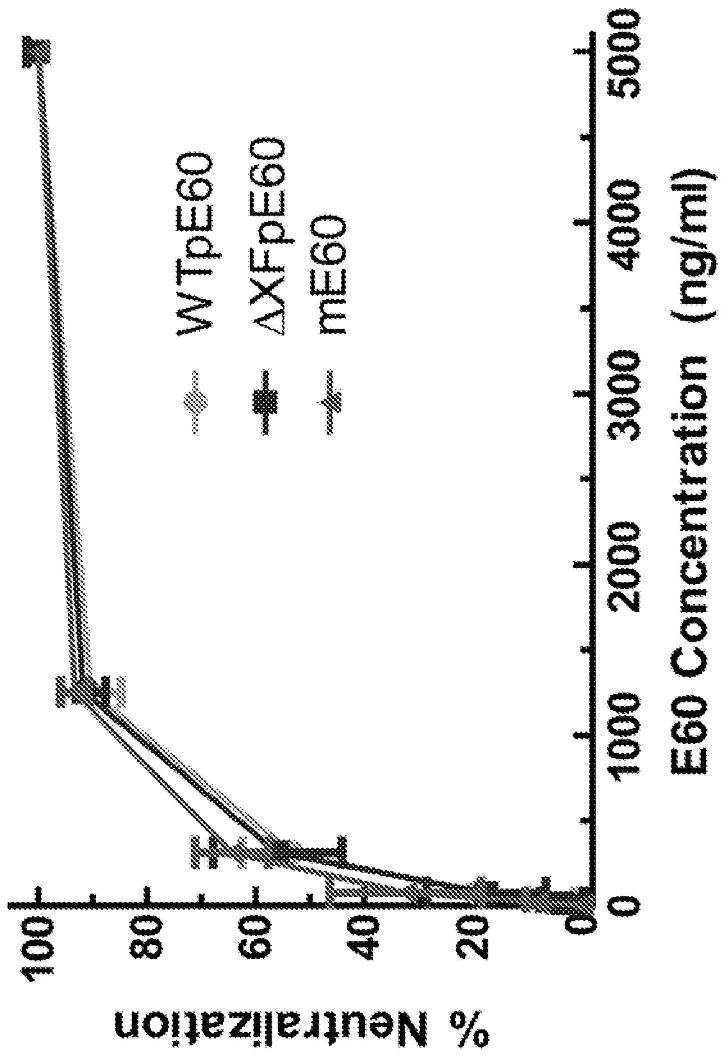
FIG. 12. Neutralization of DENV by plant-produced E60. DENY was incubated with serial dilutions of WTpE60, ΔXFpE60, and mE60 (positive control) and used to infect human U937 cells. Cells were then fixed, permeabilized, analyzed by focus reduction assay and quantitated by Biospot analysis. Mean±SEM is shown from at least two independent experiments.
Figure 14:
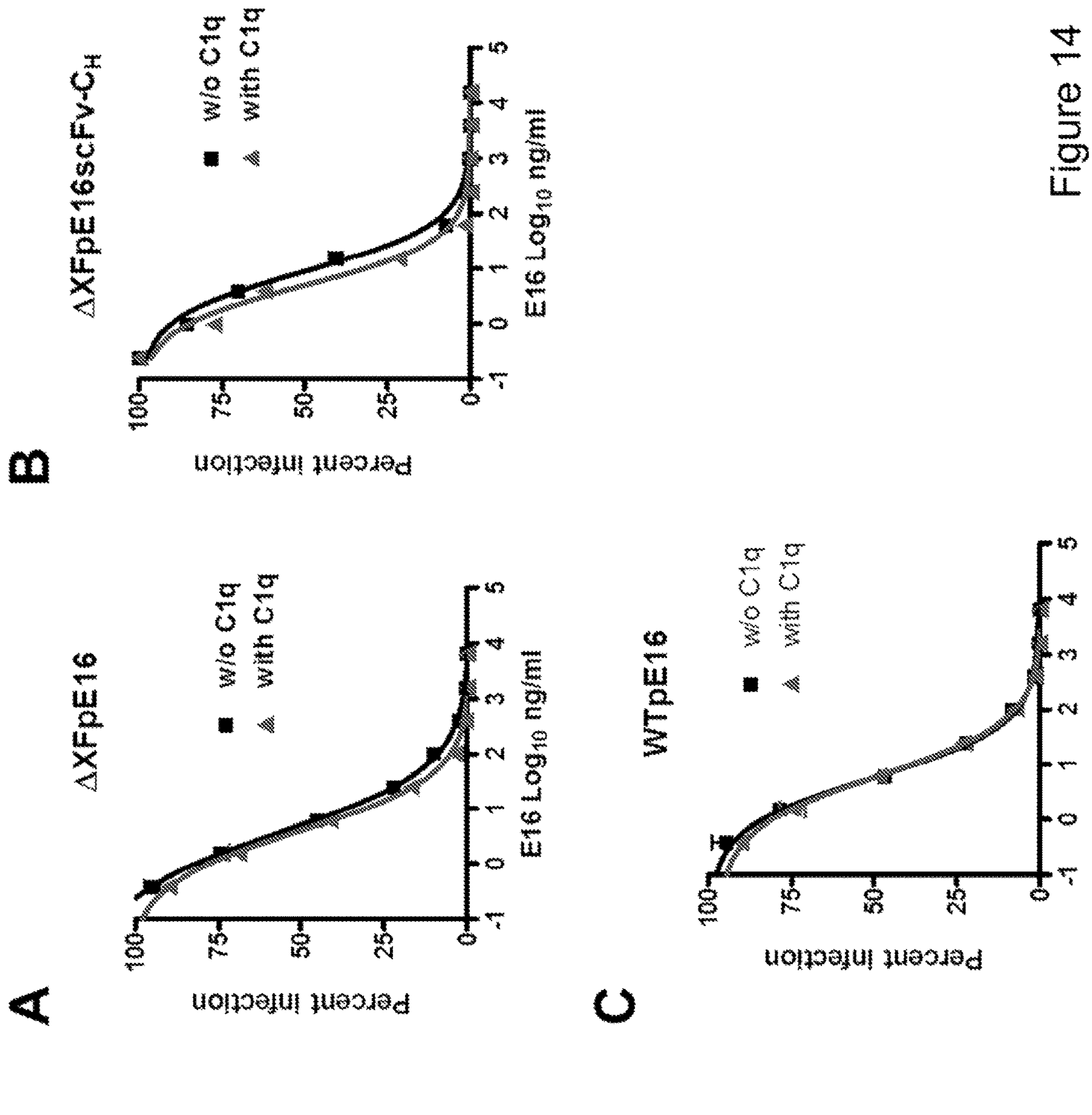
FIG. 14. Neutralization of WNV by pHu-E16 and pHu-E16scFv-$C_H^{1-3}$ produced in glycoengineered *N. benthamiana*. WNV RVPs were pre-incubated with serial dilutions of ΔXF plants-derived pHu-E16 (ΔXFpE16, A), pHu-E16scFv-$C_H^{1-3}$ (ΔXFpE16scFv-CH, B), or WT plant-derived pHu-E16 (WTpE16, C) in the presence of medium (w/o C1 q, black line) or 50 μg/ml of human C1q (with C1q, red line), and used to infect permissive Raji-DC-SIGN-R cells. After 40 hours of incubation, cells were fixed and analyzed by flow cytometry for GFP expression. Data are representative of at least two independent experiments.

To evaluate the neutralization potential of pHu-E16 variants, a focus reduction neutralization assay that measures antibody inhibition of WNV or DENY infection was used (Lai H, He J, Engle M, Diamond M S, Chen Q (2012) Robust production of virus-like particles and monoclonal antibodies with geminiviral replicon vectors in lettuce. Plant Biotechnology Journal 10: 95-104; Fuchs A, Pinto A K, Schwaeble W J, Diamond M S (2011) The lectin pathway of complement activation contributes to protection from West Nile virus infection. Virology 412: 101-109). pHu-E16scFv-$C_H^{1-3}$ and Tetra pHu-E16 neutralized WNV infection comparably to mHu-E16 and pHu-E16 (FIG. 7, EC50: mHu-E16=3.6 ng/ml, pHu-E16=3.7 ng/ml, pHu-E16scFv-$C_H^{1-3}$=5.2 ng/ml, Tetra pHu-E16=3.0 ng/ml, respectively). Thus, E16scFv-$C_H^{1-3}$ and Tetra pHu-E16 retained potent neutralizing activity against infectious WNV. Furthermore, along with pHu-E16 produced in ΔXF *N. benthamiana* plants, E16scFv-$C_H^{1-3}$ produced in ΔXF plants also retained its WNV neutralizing activity (FIG. 14). For anti-DENY MAb E60, a potent neutralizing activity was observed for both WT and ΔXF *N. benthamiana* plant-produced E60 (FIG. 12)

Figure 8:
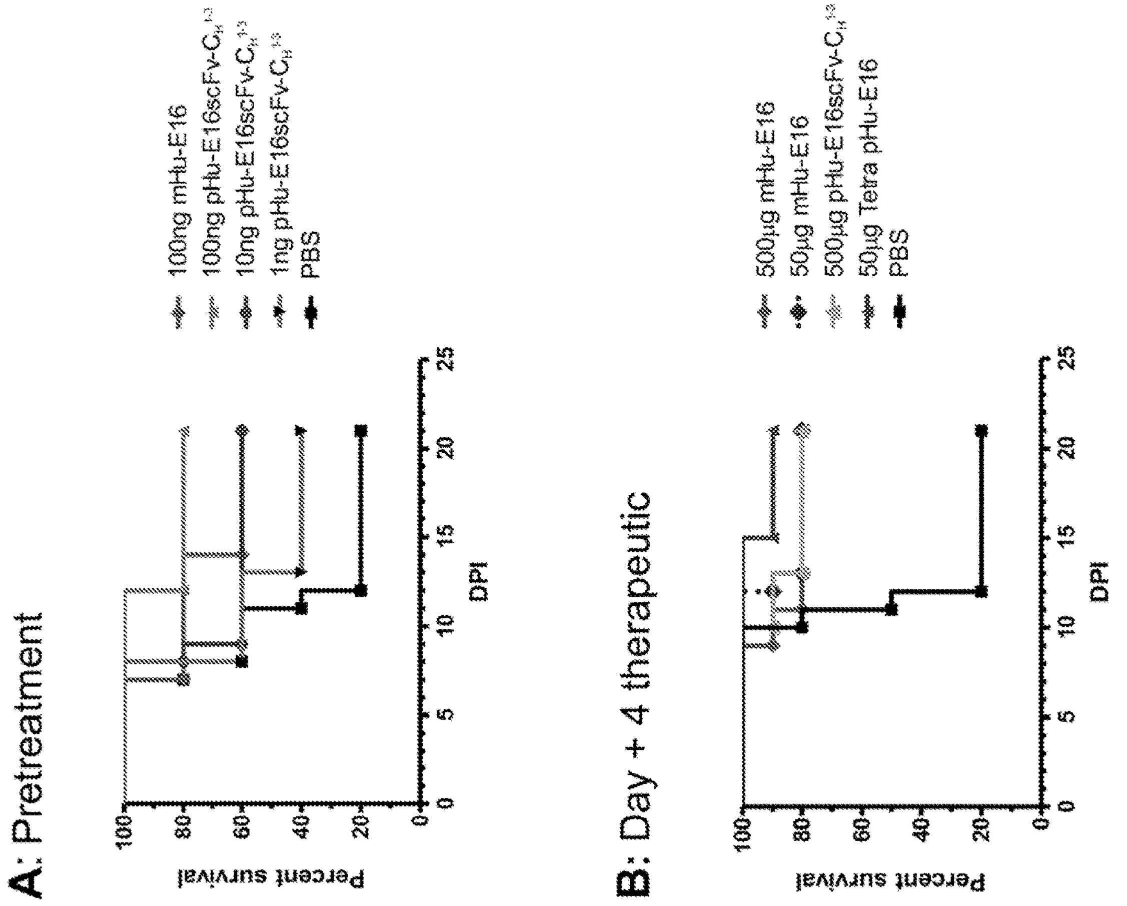
FIG. 8. pHu-E16 variants mediated protection in mice. A. Five week-old C57BL/6 mice were passively transferred saline, 100 ng of mHu-E16, or serial 10-fold increases in dose (ranging from 1 to 100 ng, n=10 mice per dose) of pHu-E16scFv-$C_H^{1-3}$ via an intraperitoneal route on the same day as subcutaneous infection with $10^2$ PFU of WNV. Survival data from at least two independent experiments were analyzed by log-rank test. B. Wild type C57BL/6 mice were infected with $10^2$ PFU of WNV and then given a single dose of the indicated doses of pHu-E16 scFv-$C_H^{1-3}$, Tetra pHu-E16 or mHu-E16 via an intraperitoneal route at day +4 after infection. Survival data from at least two independent experiments (n=10 mice per dose) were analyzed by the log-rank test.

Hu-E16 scFv-$C_H^{1-3}$ and Tetra pHu-E16 have Potent Prophylactic and Therapeutic Potential Prophylaxis and therapeutic studies were performed to evaluate the activity of pHu-E16 variants in vivo. Pretreatment studies were performed in 5 week-old wild type C57BL/6 mice (n≥10, per group) to compare the concentrations of pHu-E16scFv-$C_H^{1-3}$ and mHu-E16 that prevent WNV infection. Mice were inoculated with $10^2$ PFU of WNV (New York 2000 strain), which causes a baseline mortality of 80 to 90% in this model (Engle M, Diamond M S (2003) Antibody prophylaxis and therapy against West Nile Virus infection in wild type and immunodeficient mice. J Virol 77: 12941-12949). Increasing amounts (1 to 100 ng) of pHu-E16scFv-$C_H^{1-3}$ or 100 ng of mHu-E16 were administered as a single dose on the day of infection. Results showed that 80% of mice were protected from lethal infection when 100 ng of pHu-E16scFv-$C_H^{1-3}$ was administered ($P<0.05$), whereas the same dosage of mHu-E16 protected 60% of mice (FIG. 8A). A single injection of as low as 10 ng of pHu-E16scFv-$C_H^{1-3}$ also prevented mortality (FIG. 8A).

Post-exposure therapeutic treatments were performed by passively administering a single dose (50 or 500 μg) of pHu-E16scFv-$C_H^{1-3}$ or Tetra pHu-E16 after subcutaneous inoculation of $10^2$ PFU of WNV. Since WNV spreads to the brain in mice by day 4 after infection, the efficacy of pHu-E16 variants was investigated at this time point (FIG. 8B). Notably, 80% of mice were protected from lethal infection when 500 μg of pHu-E16scFv-$C_H^{1-3}$ was given 4 days after WNV inoculation, similar to that observed with mHu-E16 performed in parallel (FIG. 8B, $P>0.9$). A single administration of 50 μg of Tetra pHu-E16 protected up to 90% of mice from lethal infection, compared with an 80% survival rated achieved by mHu-E16 (FIG. 8B).

Figure 15:
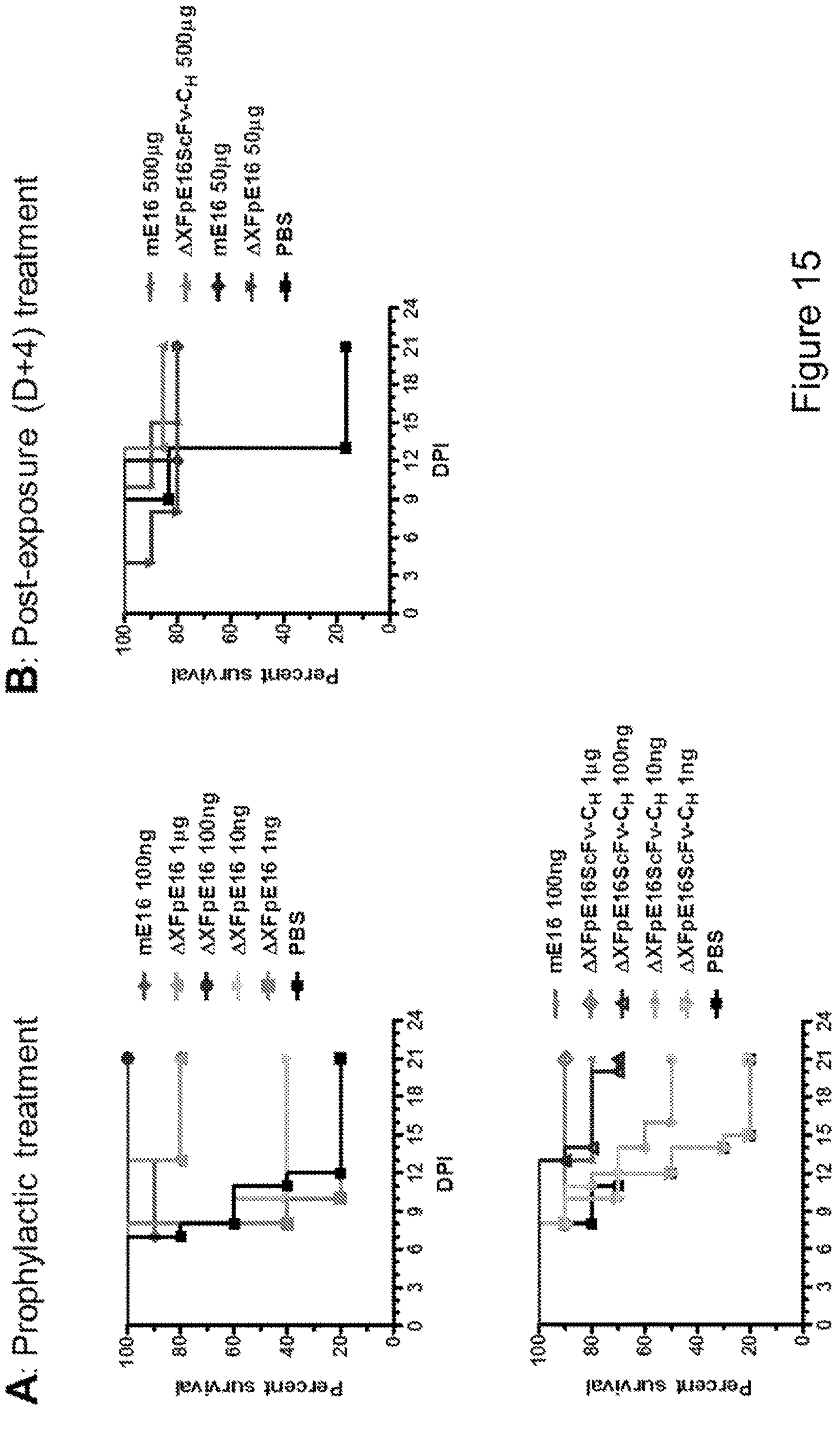
FIG. 15. ΔXFpE16 and ΔXFpE16scFv-CH mediated protection in mice. A. Five week-old C57BL/6 mice were passively transferred saline, or serial increases in dose (ranging from 1 to 1000 ng, n=10 mice per dose) of ΔXFpE16 or ΔXFpE16scFv-CH via an intraperitoneal route on the same day as subcutaneous infection with $10^2$ PFU of WNV. Survival data from at least two independent experiments were analyzed by log-rank test. mE16 (100 ng) was used in parallel as a positive control. B. Wild type C57BL/6 mice were infected with $10^2$ PFU of WNV and then given a single dose of ΔXFpE16 (50 μg), ΔXFpE16scFv-CH (500 μg) or mHu-E16 (50 μg or 500 μg) via an intraperitoneal route at day +4 after infection. Survival data from at least two independent experiments (n=10 mice per dose) were analyzed by the log-rank test.

Similarly, the prophylactic and therapeutic efficacy of glycoengineered plant (ΔXF)-derived pHu-E16 scFv-$C_H^{1-3}$ and pHu-E16 was also demonstrated in lethal WNV challenge studies in mice (FIG. 15) Overall, pHu-E16, pHu-E16 scFv-$C_H^{1-3}$ and Tetra pHu-E16 had at least equivalent prophylactic and therapeutic efficacy in mice compared to mHu-E16 regardless of whether they were produced in WT or glycoengineered plant lines.

Discussion

MAb expression was first attempted in stable transgenic plants (Hiatt A, Cafferkey R, Bowdish K (1989) Production of antibodies in transgenic plants. Nature 342: 76-78). It suffered from low yield, long lead time to generate and select transgenic plants, and unstable seed banks largely due to the randomness of transgene integration in the plant genome (position effect), the lack of control in transgene copy number, and the shortage of strong promoters to drive transgene expression (De Muynck B, Navarre C, Boutry M (2010) Production of antibodies in plants: status after twenty years. Plant Biotechnology Journal 8: 529-563). This greatly undermined the cost-saving potential of the plant expression systems. The development of transient expression systems based on deconstructed virus vectors has increased the speed and yield of MAb production in plants (Giritch A, Marillonnet S, Engler C, van Eldik G, Botterman J, et al. (2006) Rapid high-yield expression of full-size IgG antibodies in plants coinfected with noncompeting viral vectors. Proceedings of the National Academy of Sciences of the United States of America 103: 14701-14706; Chen Q, He J, Phoolcharoen W, Mason H S (2011) Geminiviral vectors based on bean yellow dwarf virus for production of vaccine antigens and monoclonal antibodies in plants. Human Vaccines 7: 331-338; Lico C, Chen Q, Santi L (2008) Viral vectors for production of recombinant proteins in plants. Journal of cellular physiology 216: 366-377; Huang Z, Chen Q, Hjelm B, Arntzen C, Mason H (2009) A DNA replicon system for rapid high-level production of virus-like particles in plants. Biotechnology and Bioengineering 103: 706-714). For example, with the MagnICON and geminiviral vectors, MAbs can be obtained within 10 days of vector infiltration into *N. benthamiana* and lettuce plants with yields up to 1 mg MAb/g LFW (Lai H, Engle M, Fuchs A, Keller T, Johnson S, et al. (2010) Monoclonal antibody produced in plants efficiently treats West Nile virus infection in mice. Proceedings of the National Academy of Sciences of the United States of America 107: 2419-2424; Lai H, He J, Engle M, Diamond M S, Chen Q (2012) Robust production of virus-like particles and monoclonal antibodies with geminiviral replicon vectors in lettuce. Plant Biotechnology Journal 10: 95-104; Huang Z, Phoolcharoen W, Lai H, Piensook K, Cardineau G, et al. (2010) High-level rapid production of full-size monoclonal antibodies in plants by a single-vector DNA replicon system. Biotechnology and bioengineering 106: 9-17; He J, Lai H, Brock C, Chen Q (2012) A Novel System for Rapid and Cost-Effective Production of Detection and Diagnostic Reagents of West Nile Virus in Plants. Journal of Biomedicine and Biotechnology 2012: 1-10; Zeitlin L, Pettitt J, Scully C, Bohorova N, Kim D, et al. (2011) Enhanced potency of a fucose-free monoclonal antibody being developed as an Ebola virus immunoprotectant. Proceedings of the National Academy of Sciences 108: 20690-20694). While MAb derivatives, such as scFv, diabodies, and RIC have been produced in plants (De Muynck B, Navarre C, Boutry M (2010) Production of antibodies in plants: status after twenty years. Plant Biotechnology Journal 8: 529-563; Phoolcharoen W, Bhoo S H, Lai H, Ma J, Arntzen C J, et al. (2011) Expression of an immunogenic Ebola immune complex in *Nicotiana benthamiana*. Plant Biotechnology Journal 9: 807-816; Phoolcharoen W, Dye J M, Kilbourne J, Piensook K, Pratt W D, et al. (2011) A nonreplicating subunit vaccine protects mice against lethal Ebola virus challenge. Proceedings of the National Academy of Sciences 108: 20695-20700), the ability of plants to express and assemble larger or more complex MAb-derived molecules such as IgG-like tetravalent MAbs or bifunctional MAbs has not been reported.

Here, the feasibility of plant cells in producing such an IgG-like tetravalent MAb against WNV based on MAb Hu-E16 was investigated. The results showed that two Hu-E16scFvs each genetically fused to the $C_H^{1-3}$ and $C_L$ fragment of IgG can be produced efficiently in both WT and glycoengineered *N. benthamiana* leaves. The Hu-E16scFv- $C_H^{1-3}$ and Hu-E16scFv-$C_L$ efficiently assembled into an IgG-like molecule. The study also demonstrated that the tetravalent pHu-E16 can be recovered efficiently to high (>90%) purity, and retain antigen-binding and neutralization activity in vitro. Most importantly, a single dose of Tetra-pHu-E16 protected mice at least equivalently as mHu-E16 against a lethal WNV infection several days after exposure. To our knowledge, this is the first example in a plant of expression and assembly of a large and complex IgG-like tetravalent functional molecule. Tetra pHu-E16 was expressed rapidly in *N. benthamiana* leaves and reached its highest level of accumulation 9 days after leaf infiltration. While its expression level is slightly lower than that of pHu-E16, this level is within the range feasible for commercial production (Chen Q (2013) Virus-like Particle Vaccines for Norovirus Gastroenteritis. In: Giese M, editor. Molecular Vaccines. Vienna: Springer, DOI:10.1007/978-3-7091-1419-3_8. pp. 153-181), and likely can be increased by further genetic optimization (De Muynck B, Navarre C, Boutry M (2010) Production of antibodies in plants: status after twenty years. Plant Biotechnology Journal 8: 529-563). The rapid accumulation and assembly of Tetra pHu-16 and the availability of a scalable and current Good Manufacturing Practice (cGMP) compliant purification scheme suggest the viability of such molecules as a platform for novel therapeutic candidate.

Another goal of this research is to further increase the efficacy of Hu-E16 MAb as a proof-of-principle for antibody treatment of viral infections in the CNS. Even though mHu-E16, pHu-E16, pHu-E16scFv-$C_H^{1-3}$, and Tetra pHu-E16 showed excellent efficacy, their window of clinical treatment will be limited via peripheral delivery systems (Lai H, Engle M, Fuchs A, Keller T, Johnson S, et al. (2010) Monoclonal antibody produced in plants efficiently treats West Nile virus infection in mice. Proceedings of the National Academy of Sciences of the United States of America 107: 2419-2424; Oliphant T, Engle M, Nybakken G, Doane C, Johnson S, et al. (2005) Development of a humanized monoclonal antibody with therapeutic potential against West Nile virus. Nature Medicine 11: 522-530). These current MAb-based therapeutic candidates cannot efficiently cross the BBB and accumulate to high levels in the brain unless there is widespread inflammation and breakdown of the BBB. Thus, it would be desirable to develop pHu-E16 variants that can cross the BBB more efficiently. One possible strategy is to develop IgG-like bifunctional MAbs that with a similar structure as the Tetra pHu-E16, but assembled from two scFvs with distinct affinity and binding to two disparate antigens. For example, one of the two scFvs could bind to a specific receptor (e.g., insulin receptor on BBB to facilitate its transport into the brain, and the other scFv would retain its binding and neutralization against WNV in the brain. The successful production and assembly of Tetra pHu-E16 and the demonstration of its therapeutic activity here bring us closer to developing such Hu-E16 bifunctional MAbs to prolong the window of its efficacy.

The N-linked glycosylation of MAbs affects its stability, FcγR and C1q binding, pharmacokinetics, effector function and efficacy (Houde D, Peng Y, Berkowitz S A, Engen J R (2010) Post-translational modifications differentially affect IgG1 conformation and receptor binding. Mol Cell Proteomics 9: 1716-1728). N-linked glycosylation occurs as a series of post-translational modification steps initiated in the ER and processed through different compartments of the Golgi complex of the host cell. Altering the structure of a protein or its folding may affect glycan modification and the corresponding cellular localization (Loos A, Van Droogenbroeck B, Hillmer S, Grass J, Pabst M, et al. (2011) Expression of antibody fragments with a controlled N-glycosylation pattern and induction of endoplasmic reticulum-derived vesicles in seeds of *Arabidopsis*. Plant Physiol 155: 2036-2048; Feige M J, Groscurth S, Marcinowski M, Shimizu Y, Kessler H, et al. (2009) An unfolded CH1 domain controls the assembly and secretion of IgG antibodies. Mol Cell 34: 569-579). However, the impact of structural variations in the native IgG on N-linked glycosylation has not been thoroughly studied. Here, the difference in the N-linked glycans of pHu-E16 IgG and its pHu-E16scFv-$C_H^{1-3}$ variant was first examined. The results revealed that their N-linked glycan profiles were different from one another. pHu-E16 exhibited the expected complex-type N-linked glycans (Loos A, Steinkellner H (2012) IgG-Fc glycoengineering in non-mammalian expression hosts. Arch Biochem Biophys 526: 167-173), confirming it was fully processed through the endomembrane system and secreted into the apoplast as designed. In contrast, pHu-E16scFv-$C_H^{1-3}$ predominantly displayed Man8 and Man9-types of oligomannosidic structures, which indicates incomplete glycan processing and suggests its aberrant localization in ER or ER-derived vesicles. A similar observation in glycoforms and aberrant subcellular deposition was reported for *Arabidopsis* (*Arabidopsis thaliana*) seed-derived 2G12scFV-Fc, a MAb variant against Human immunodeficiency virus (HIV), and to a lesser extent, for HA78scFv-Fc, an anti-hepatitis A virus MAb also produced in *Arabidopsis* seed (Loos A, Van Droogenbroeck B, Hillmer S, Grass J, Pabst M, et al. (2011) Expression of antibody fragments with a controlled N-glycosylation pattern and induction of endoplasmic reticulum-derived vesicles in seeds of *Arabidopsis*. Plant Physiol 155: 2036-2048). However, in the same study, leaf-derived HA78scFv-Fc displayed the expected complex-type N-glycans, whereas leaf-produced 2G12scFv-Fc exhibited the ER-typical oligomannosidic glycans and was functionally inactive (Loos A, Van Droogenbroeck B, Hillmer S, Grass J, Pabst M, et al. (2011) Expression of antibody fragments with a controlled N-glycosylation pattern and induction of endoplasmic reticulum-derived vesicles in seeds of *Arabidopsis*. Plant Physiol 155: 2036-2048). These observations suggest that beside the polypeptide component of scFv-Fcs, the type of plant tissue (e.g., seeds vs. leaves) and plant species may also impact the N-linked glycosylation status of scFv-Fc variants. It should be noted that the structure of 2G12scFV-Fc and HA78scFv-Fc is different from that of pHu-E16scFv-$C_H^{1-3}$, as their scFvs were fused to the Fc fragment (hinge-$C_H^{2-3}$) of IgG, thus, lacking the HC constant region 1 domain ($C_H^1$). To investigate if this were a phenomenon unique to plant cells, the N-linked glycan profiles of the equivalent Hu-E16 counterpart variants produced in mammalian cells were compared. The results indicated that in addition to the predominant complex-type glycans ($GnGnF^6$ and $AGnF^6$), mHu-E16scFv-$C_H^{1-3}$ also had a substantial amount of oligomannosidic glycans, mostly M5 and M7, whereas no such glycans were observed in the native IgG version of mHu-E16. This result suggests that at least for Hu-E16, the unusual N-linked glycosylation of scFv-$C_H^{1-3}$ is not unique to plants but shared by mammalian cells, even though the percentage and the particular species of oligomannosidic glycans varies between the two cell types.

To provide further insight for this N-glycosylation difference, three additional pHu-E16 variants were expressed with various combinations of HC and LC components. Examining whether LC or the proper pairing of HC and LC regulated the proper N-linked glycosylation of MAb and its variants was of particular interest. Co-expression of LC with pHu-E16scFv-$C_H^{1-3}$ significantly increased its level of complex N-linked glycans percentage. In Tetra pHu-E16, the co-expression and pairing of scFv-$C_L$ with scFv-$C_H^{1-3}$ also increased the amount of complex-type N-linked glycans. Furthermore, the pairing of the HC of pHu-E16 with scFv-$C_L$ resulted in a predominantly complex-type N-linked glycosylation pattern, similar to seen with the parent pHu-E16. These results support the hypothesis that $C_L$ domain of an antibody is essential for its secretion in the cell (Feige, M. J., S. Groscurth, et al. (2009). "An unfolded CH1 domain controls the assembly and secretion of IgG antibodies." Mol Cell 34(5): 569-79). It was suggested previously that HC dimers are retained in the ER by the chaperone BiP and are released only upon binding with $C_L$ to ensure its proper folding. The results corroborate this and highlight the importance of LC pairing with HC for the proper processing of antibody N-linked glycosylation. It was speculated that in the absence of LC pHu-E16scFv-$C_H^{1-3}$ was retained in the ER by BiP, preventing its transport within the endomembrane system and resulting in the observed ER-typical oligomannosidic glycoform. In contrast, co-expression of LC or pHu-E16scFv-$C_L$ enabled the $C_L$ domain to release pHu-E16scFv-$C_H^{1-3}$ from BiP and to transport it to the Golgi compartments for further assembly, glycan processing and secretion. While the N-linked glycosylation of the scFv-$C_H^{1-3}$ and scFv-Fc variant may be regulated by many factors, the results suggest that the lack of $C_L$ and its pairing with the $C_H^1$ contributes to the aberrant N-linked glycosylation and intracellular localization of pHu-E16scFv-$C_H^{1-3}$ and other previously reported scFv-Fcs, even though the degree of aberration may vary depending on the specific scFv-Fc/scFv-$C_H^{1-3}$ or the cell type in which it was produced.

In this study, wild-type (WT) *N. benthamiana* plants were first used for expressing the pHu-E16 variants. It was also demonstrated that pHu-E16 produced in WT plants have a highly homogeneous (90%) population of the expected glycoform, GnGnXF, in contrast of a more heterogeneous mixture of Hu-E16 produced in mammalian cells. While N-linked glycosylation of proteins in plants is similar to that of mammalian cells, WT plants add plant-specific β-1,2-xylose and core α-1,3-fucose residues to complex N-linked glycans and lack terminal β1,4-Gal and N-acetylneuraminic acid (Neu5Ac) residues (Gomord V, Fitchette A C, Menu-Bouaouiche L, Saint-Jore-Dupas C, Plasson C, et al. (2010) Plant-specific glycosylation patterns in the context of therapeutic protein production. Plant Biotechnology Journal 8: 564-587; Bosch D, Castilho A, Loos A, Schots A, Steinkellner H (2013) N-Glycosylation of Plant-produced Recombinant Proteins. Curr Pharm Des 19: 5503-5512). These differences in protein glycosylation between WT plant and mammalian cells were one of the reservations of plant-expression platforms for human therapies, because they could produce improper glycoforms that alter efficacy or result in plant-glycan specific immune responses that can accelerate protein clearance or cause potential adverse effects through immune complex formation. To overcome this challenge, glycosylation pathway in *N. benthamiana* and several other plants has been "humanized" through glycoengineering, for example, by genetically suppressing or eliminating enzymes for the biosynthesis of plant-specific glycans and by introducing glycoenzymes from mammalian cells (Bosch D, Castilho A, Loos A, Schots A, Steinkellner H (2013) N-Glycosylation of Plant-produced Recombinant Proteins. Curr Pharm Des 19: 5503-5512). These efforts have led to the creation of a portfolio of "humanized" plant lines that produce MAbs that lack plant-specific glycans and produce glycoforms that are essentially mammalian (Bosch D, Castilho A, Loos A, Schots A, Steinkellner H (2013) N-Glycosylation of Plant-produced Recombinant Proteins. Curr Pharm Des 19: 5503-5512). For example, a double knockout (ΔXF) *N. benthamiana* plant line, which was created by RNAi to suppress the expression of α-1,3-fucosyltransferase and β-1,2-xylosyltransferase, was used for production of an anti-Ebola MAb 13F6 (Zeitlin L, Pettitt J, Scully C, Bohorova N, Kim D, et al. (2011) Enhanced potency of a fucose-free monoclonal antibody being developed as an Ebola virus immunoprotectant. Proceedings of the National Academy of Sciences 108: 20690-20694; Strasser R, Stadlmann J, Schahs M, Stiegler G, Quendler H, et al. (2008) Generation of glyco-engineered *Nicotiana benthamiana* for the production of monoclonal antibodies with a homogeneous human-like N-glycan structure. Plant Biotechnol J 6: 392-402). 13F6 produced in the ΔXF plant line had no plant-specific N-glycans and 90% of 13F6 had the predicted mammalian glycoform GnGn (Zeitlin L, Pettitt J, Scully C, Bohorova N, Kim D, et al. (2011) Enhanced potency of a fucose-free monoclonal antibody being developed as an Ebola virus immunoprotectant. Proceedings of the National Academy of Sciences 108: 20690-20694). In contrast, mammalian cell-produced 13F6 had a mixture of 3-5 glycoforms with the most dominant glycoform (G0) ranging from 35-53%. The high glycan homogeneity of plant-made 13F6 and the lack of core fucose increased its protection of mice against a lethal Ebola virus challenge compared to the mammalian cell produced 13F6. pHu-E16, pHu-E16 scFv-$C_H^{1-3}$, Tetra-E16, and other variants were expressed in these "humanized" *N. benthamiana* lines to produce highly uniform mammalian glycoforms. Indeed, these pHu-E16 variants were robustly produced in the ΔXF *N. benthamiana* plant line, yielding MAbs with the expected mammalian glycoform of GnGn with a 95% degree of uniformity.

The N-linked glycosylation pattern in the Fc region of an antibody affects its binding to FcΔRs and C1q, and consequently alters its effector function such as antibody-dependent cell mediated cytotoxicity (ADCC) and complement-dependent cytotoxicity (CDC) (Houde D, Peng Y, Berkowitz S A, Engen J R (2010) Post-translational modifications differentially affect IgG1 conformation and receptor binding. Mol Cell Proteomics 9: 1716-1728). The highly homogenous and defined nature of N-glycans displayed by plant-derived MAbs provides the opportunity to develop MAb glycoforms that enhance the efficacy through modulating their effector function. For example, plant-produced 13F6 has a higher affinity to FcγRIII than its mammalian cell-produced counterpart, and provided better protection against Ebola virus challenge in mice presumably via enhanced ADCC activity. Here, it was found that due to their distinct N-glycoforms, pHu-E16, pHu-E16scFv-$C_H^{1-3}$, and Tetra pHu-E16 exhibited differential binding to C1q and various FcγRs including $CD16V^{158}$, $CD16F^{158}$ $CD32aR^{131}$ and $CD32aH^{131}$, CD32B, and CD64. For example, while pHu-E16 showed reduced binding to all FcγRs and C1q, pHu-E16scFv-$C_H^{1-3}$ demonstrated slightly enhanced binding to the low-affinity ($CD16F^{158}$) isoform of CD16A and CD64, and maintained similar binding to the high-affinity ($CD16V^{158}$) CD16A isoform as mHu-E16. This diversity of binding affinity to C1q and various FcγRs by an individual MAb variant molecule will allow investigation of the impact of glycan moieties on MAb effector function and the development of MAb variants that are best suited for its efficacy or safety depending on the particular clinical application.

In addition to ADCC and CDC, the interaction between Fc and FcγRs can have pathogenic consequences. For example, one of the major impediments towards developing antibody-based therapeutics for certain flavivirus infections (e.g., Dengue virus) is the at least theoretical risk of ADE, which may render anti-flavivirus MAb treated subjects more susceptible to infection. ADE occurs because sub-neutralizing concentrations of antibodies (including therapeutic MAbs) and the infecting flavivirus form complexes that bind to FcγR-bearing cells, resulting in increased virus uptake and replication (Morens DM (1994) Antibody-dependent of enhancement of infection and the pathogenesis of viral disease. Clin Inf Dis 19: 500-512; Halstead S B, Mahalingam S, Marovich M A, Ubol S, Mosser D M (2010) Intrinsic antibody-dependent enhancement of microbial infection in macrophages: disease regulation by immune complexes. Lancet Infect Dis 10: 712-722; Mehlhop E, Ansarah-Sobrinho C, Johnson S, Engle M, Fremont D H, et al. (2007) Complement protein C1q inhibits antibody-dependent enhancement of flavivirus infection in an IgG subclass-specific manner. Cell Host Microbe 2: 417-426). Thus, whether the unique binding of pHu-E16 variants to FcγRs affected ADE was investigated. The results demonstrated that all pHu-E16 variants lost ADE activity on CD32A+ K562 cells. Thus, plant complex-type N-glycans or the mammalian form of oligomannosidic glycans carried by plant-produced pHu-E16 variants cannot induce the development of ADE on cells bearing CD32A, consistent with their loss of binding in vitro by SPR. In a separate experiment, it was observed that ADE also was eliminated for a glycoengineered plant-derived pHu-E16 that carried the mammalian glycoform of GnGn. These results collectively demonstrate the potential of plant-made MAbs and their variants to be used as therapeutics against ADE-prone viruses. While it was previously reported that an aglycosylated version of a MAb can eliminate the risk of ADE (Balsitis S J, Williams K L, Lachica R, Flores D, Kyle J L, et al. (2010) Lethal Antibody Enhancement of Dengue Disease in Mice Is Prevented by Fc Modification. PLoS Pathog 6: e1000790; Williams K L, Sukupolvi-Petty S, Beltramello M, Johnson S, Sallusto F, et al. (2013) Therapeutic efficacy of antibodies lacking Fcgamma receptor binding against lethal dengue virus infection is due to neutralizing potency and blocking of enhancing antibodies [corrected]. PLoS Pathog 9: e1003157), the complete removal of N-linked glycans and the resulting abolishment of binding to C1q also may compromise the efficacy of a MAb, which uses CDC activity. Plant-derived MAb glycolvariants that minimize ADE but retain C1q binding might have better efficacy than their aglycosylated counterparts. While ADE is not a critical issue for WNV infection, it is highly relevant to its closely related Dengue virus, and some coronaviruses, paramyxoviruses, and lentiviruses (Santi L, Batchelor L, Huang Z, Hjelm B, Kilbourne J, et al. (2008) An efficient plant viral expression system generating orally immunogenic Norwalk virus-like particles. Vaccine 26: 1846-1854).

Accordingly, a plant-derived anti-DENV MAb (E60) as a therapeutic candidate against all 4 serotypes of DENV was also developed. Our results demonstrated that E60 and its scFv-$C_H^{1-3}$ variants can be expressed at high levels in both WT and ΔXF *N. benthamiana* plants. These plant-derived E60s were easily purified to high homogeneity with scalable and cGMP compliant downstream processing scheme. Furthermore, they retained the specific binding and the potent neutralizing activities as E60 produced in mammalian cells, but with greatly reduced or eliminated ADE activity.

In summary, it was demonstrated for the first time the ability of plant cells to express and assemble MAb and its variants against both WNV and DENV, including a large and complex IgG-like tetravalent MAb variant. The demonstration of producing MAb variants with highly specific and homogeneous mammalian glycosylation patterns in plants supports the feasibility of designing MAbs with tailor-made N-glycosylation for their optimized safety or efficacy. The demonstration of anti-WNV and anti-DENV MAbs which retain their in vitro and in vivo therapeutic function, yet lacking ADE, may overcome the major impediment for the development of MAb-based therapeutics against flavivirus and lead to safer antibody-based therapeutics against flavivirus and other viruses prone to ADE.

Materials and Methods

Expression of pHu-E16 and E60 MAb variants in *N. benthamiana* leaves

A plasmid containing the pHu-E16 MAb sequence (Lai H, Engle M, Fuchs A, Keller T, Johnson S, et al. (2010) Monoclonal antibody produced in plants efficiently treats West Nile virus infection in mice. Proceedings of the National Academy of Sciences of the United States of America 107: 2419-2424) was used as template for the construction of the pHu-E16scFv. Primers H5 (5' GAATTCACAA TGGGATGG 3' (SEQ ID NO:9)) and H3 (5' CCTCCTGAAG TTGAACCAGA AGACACAGTA ACAGTAG 3' (SEQ ID NO:10)) were used to amplify the pHu-E16 $V_H$, and primers L5 (5' GGTTCAACTT CAGGAGGAGG ATCAGGTGGT GGTTCAGGAG GTGGAGGATC TTCT GATATC GTTATGACAC AATC 3' (SEQ ID NO:11)) and L3 (5' TGCTAGCTT TGATCTCCAA CTTAGTTCC 3' (SEQ ID NO:12)) were used to amplify the pHu-E16 $V_L$. Subsequently, the $V_H$ and $V_L$. sequences were linked together by overlapping PCR. The product was cloned using EcoRI and NheI sites into a plasmid, which already contains the coding sequence of the $C_H^{1-3}$ or $C_L$ to yield EcoRI-pHu-E16scFv-$C_H^{1-3}$-BamHI or EcoRI-pHu-E16scFv-$C_L$-BamHI constructs. pHu-E16scFv-$C_H^{1-3}$ and E16scFv-$C_L$ coding sequences were then cloned into plant expression vector pICH11599 and pICH21595, respectively with EcoRI and BamHI. The construction of pHu-E16 HC and pHu-E16 LC in pICH11599 and pICH21595 has been described previously (Lai H, Engle M, Fuchs A, Keller T, Johnson S, et al. (2010) Monoclonal antibody produced in plants efficiently treats West Nile virus infection in mice. Proceedings of the National Academy of Sciences of the United States of America 107: 2419-2424). None of the pHu-E16 constructs contains the ER-retention signal KDEL (SEQ ID NO:8).

For E60, a plasmid containing the sequence of the HC of E60 (Williams, et al. (2013). "Therapeutic efficacy of antibodies lacking Fcgamma receptor binding against lethal dengue virus infection is due to neutralizing potency and blocking of enhancing antibodies [corrected]." *PLoS Pathog* 9(2): e1003157) was used as template with primers 5'-TTGGTTGCAACAGCTACTGGTGTTCATTCTGAGGTCCAGGTGCAACAG-3' (SEQ ID NO:13) and 5'-AGAATTCACAATGGGATGGTCTTGTATCATCCTTTTCTTGGTTGCAACAGC-3' (SEQ ID NO:14) to generate the HC variable region ($V_H$) of E60. Similarly, the LC variable region ($V_L$) was amplified with primers 5'-TTGGTTGCAACAGCTACTGG TGTTCA TTCTGA CATCCTG ATGACCCAATC-3' (SEQ ID NO:15) and 5'-AGAATTCACAATGGGATGGTCTTGTATCA TCCTTT TCTTGG TTGCAACAGC-3' (SEQ ID NO:16) from a plasmid containing the E60 LC gene (Williams, et al. (2013). "Therapeutic efficacy of antibodies lacking Fcgamma receptor binding against lethal dengue virus infection is due to neutralizing potency and blocking of enhancing antibodies [corrected]." *PLoS Pathog* 9(2): e1003157). The $V_H$ and $V_L$ PCR products were then cloned using EcoRI and NheI sites into plasmids pIgG1-CH and pIgG-kCL (He, et al. (2014). "Generation and Analysis of Novel Plant-Derived Antibody-Based Therapeutic Molecules against West Nile Virus." *PLoS ONE* 9(3): e93541 DOI: 93510.91371/journal.pone.0093541), respectively.

Plant expression vectors were individually transformed into *A. tumefaciens* GV3101 by electroporation as previously described (Santi L, Batchelor L, Huang Z, Hjelm B, Kilbourne J, et al. (2008) An efficient plant viral expression system generating orally immunogenic Norwalk virus-like particles. Vaccine 26: 1846-1854). Wild-type *N. benthamiana* plants were grown and Agroinfiltrated or co-Agroinfiltrated with GV3101 strains containing the pHu-E16scFv-$C_H^{1-3}$, pHu-E16scFv-$C_H^{1-3}$/LC, HC/pHu-E16scFv-$C_L$ or pHu-E16scFv-$C_H^{1-3}$/pHu-E16scFv-$C_L$ 3' modules along with their respective 5' modules and an integrase construct as described previously to express pHu-E16 variants (Lai H, Engle M, Fuchs A, Keller T, Johnson S, et al. (2010) Monoclonal antibody produced in plants efficiently treats West Nile virus infection in mice. Proceedings of the National Academy of Sciences of the United States of America 107: 2419-2424; Lai H, Chen Q (2012) Bioprocessing of plant-derived virus-like particles of Norwalk virus capsid protein under current Good Manufacture Practice regulations. Plant Cell Reports 31: 573-584).

Extraction and Purification of pHu-E16 and E60 Variants from Plant Leaves

For evaluating the temporal pattern of pHu-E16 and E60 variant expression, Agroinfiltrated leaves were harvested 5, 6, 7, 8, 9, and 10 dpi. Leaves were harvested 9 dpi for other protein analysis. Extraction and purification of pHu-E16 or E60 variants from plant leaves were performed with a method previously reported for pHu-E16 MAb (Lai H, Engle M, Fuchs A, Keller T, Johnson S, et al. (2010) Monoclonal antibody produced in plants efficiently treats West Nile virus infection in mice. Proceedings of the National Academy of Sciences of the United States of America 107: 2419-2424). Briefly, leaves were homogenized in extraction buffer (PBS, 1 mM EDTA, 10 mg/ml sodium ascorbate, 10 μg/ml leupeptin, 0.3 mg/ml PMSF). The crude plant extract was clarified by centrifugation at 17,700×g for 30 min at 4° C. pHu-E16 variants in clarified protein extract were purified by a two-step purification process comprised of ammonium sulfate precipitation and protein A affinity chromatography.

SDS-PAGE, Western Blot, ELISA and Flow Cytometry with Yeast Surface Display

Protein samples were subjected to 10% SDS-PAGE under reducing (5% v/v β-mercaptoethanol) or to 4-20% gradient SDS-PAGE under non-reducing conditions. Gels were stained with Coomassie blue or used to transfer proteins onto PVDF membranes. Horseradish peroxidase (HRP)-conjugated antibodies against human-kappa LC or gamma HC (Southern Biotech) were used for western blot analysis as previously described (Lai H, Engle M, Fuchs A, Keller T, Johnson S, et al. (2010) Monoclonal antibody produced in plants efficiently treats West Nile virus infection in mice. Proceedings of the National Academy of Sciences of the United States of America 107: 2419-2424). pHu-E16 variant expression and antigen binding was examined with an ELISA as described (Lai H, Engle M, Fuchs A, Keller T, Johnson S, et al. (2010) Monoclonal antibody produced in plants efficiently treats West Nile virus infection in mice. Proceedings of the National Academy of Sciences of the United States of America 107: 2419-2424). Briefly, DIII (amino acids 296-415) of the New York 1999 strain of WNV purified from E. coli (Oliphant T, Nybakken G E, Austin S K, Xu Q, Bramson J, et al. (2007) Induction of epitope-specific neutralizing antibodies against West Nile virus. J Virol 81: 11828-11839) was immobilized on microtiter plates. After incubation with plant protein extract or purified pHu-E16 variants, an HRP-conjugated anti-human-gamma HC antibody (Southern Biotech) was used as the detection antibody. The plates were developed with TMB substrate (KPL Inc). mHu-E16 (Oliphant T, Engle M, Nybakken G, Doane C, Johnson S, et al. (2005) Development of a humanized monoclonal antibody with therapeutic potential against West Nile virus. Nature Medicine 11: 522-530) and pHu-E16 (Lai H, Engle M, Fuchs A, Keller T, Johnson S, et al. (2010) Monoclonal antibody produced in plants efficiently treats West Nile virus infection in mice. Proceedings of the National Academy of Sciences of the United States of America 107: 2419-2424) were used as reference standards. Yeast displaying WNV DIII or DENV DI-II on their surface were generated, stained with MAb variants, and analyzed with a Becton Dickinson FACSCalibur flow cytometer as described (Lai H, Engle M, Fuchs A, Keller T, Johnson S, et al. (2010) Monoclonal antibody produced in plants efficiently treats West Nile virus infection in mice. Proceedings of the National Academy of Sciences of the United States of America 107: 2419-2424 Oliphant T, Engle M, Nybakken G, Doane C, Johnson S, et al. (2005) Development of a humanized monoclonal antibody with therapeutic potential against West Nile virus. Nature Medicine 11: 522-530).

N-Linked Glycan Analysis

The N-linked glycosylation profile was determined by LC-ESI-MS as previously published (Stadlmann J, Pabst M, Kolarich D, Kunert R, Altmann F (2008) Analysis of immunoglobulin glycosylation by LC-ESI-MS of glycopeptides and oligosaccharides. Proteomics 8: 2858-2871). Briefly, purified MAb variants were separated by reducing SDS-PAGE, stained with Coomassie, and the HC-containing band was excised from the gel. Upon S-alkylation and tryptic or tryptic/GluC digestion, fragments were eluted from the gel with 50% acetonitrile and separated on a Reversed Phase Column (150×0.32 mm BioBasic-18, Thermo Scientific) with a gradient of 1%-80% acetonitrile. Glycopeptides were analyzed with a quadruple time-of-flight (Q-TOF) Ultima Global mass spectrometer (Waters, Milford, Mass., USA). Spectra were summed and deconvoluted for identification of glycoforms. Glycans were annotated according to the ProGlycAn nomenclature (www.proglycan.com).

Surface Plasmon Resonance

Binding activity measurement of MAb variants for human C1q and FcγRs (CD16A-$158^{val}$ ($CD16V^{158}$), CD16A-$158^{phe}$($CD16F^{158}$) CD32A-$131^{arg}$ ($CD32aR^{131}$), CD32A-$131^{his}$ ($CD32aH^{131}$), CD32B, and CD64) was performed by SPR on a BIAcore 3000 biosensor (GE, Healthcare). WNV E protein was immobilized on the CM-5 sensor chip (~3000RU) by an amine coupling kit as recommended by the manufacturer. Hu-E16 variants were bound to the E protein surface at approximately 700RU followed by injection of C1q at 50 nmol/L or the soluble monomeric receptors CD16A-$158^{val}$, CD16A-$158^{phe}$ at concentrations of 500 nmol/L, respectively, and flow rate of 30 μl/min for 60 sec with dissociation time 60 sec. Dimeric Fc-G2 (N297Q) fusions of human CD32B, CD32A-$131^{arg}$, and CD32A-$131^{his}$, or human soluble CD64 were injected at 200 nmol/L or at 50 nmol/L, respectively. Each receptor was injected in duplicate. Between experiments, the naked antigen surface was regenerated by pulse injection of 10 mM glycine pH 1.5. All binding experiments were performed in 10 mM Hepes, pH 7.4, 150 mM NaCl, 3 mM EDTA, and 0.005% P20 surfactant.

Antibody-Dependent Enhancement Assay

The enhancing activity of the MAbs was determined with CD32A$^+$ K562 cells (Pierson T C, Xu Q, Nelson S, Oliphant T, Nybakken G E, et al. (2007) The Stoichiometry of Antibody-Mediated Neutralization and Enhancement of West Nile Virus Infection. Cell host & microbe 1: 135-145) in at least three independent experiments in triplicate using a high-throughput flow cytometry-based assay with GFP pseudo-infectious WNV replicon particles essentially as described (Pierson T C, Xu Q, Nelson S, Oliphant T, Nybakken G E, et al. (2007) The Stoichiometry of Antibody-Mediated Neutralization and Enhancement of West Nile Virus Infection. Cell host & microbe 1: 135-145). K562 erythroleukemic cells were obtained from the American Type Cell Collection (ATCC CCL-243).

WNV and DENY Neutralization

A focus reduction neutralization assay was used to assess the neutralizing activity of pHu-E16 or E60 variants against WNV/DENV essentially as previously described (Fuchs A, Pinto A K, Schwaeble W J, Diamond M S (2011) The lectin pathway of complement activation contributes to protection from West Nile virus infection. Virology 412: 101-109). Neutralization curves were generated using Prism software to express the percent reduction of spot numbers in samples pre-incubated with mAb compared to wells with virus pre-incubated with medium alone, and EC50 values calculated.

Efficacy of MAbs in Vivo

This study was carried out in strict accordance with the recommendations in the Guide for the Care and Use of Laboratory Animals of the National Institutes of Health. Injections were performed under anesthesia that was induced and maintained with ketamine hydrochloride and xylazine, and all efforts were made to minimize suffering. C57BL/6 mice were housed in a pathogen-free mouse facility. Mice received a single dose of purified pHu-E16scFv-$C_H^{1-3}$, Tetra pHu-E16, or mHu-E16 by intraperitoneal injection the same day or four days after footpad infection with $10^2$ PFU of WNV strain 3000.0259. Kaplan-Meier analysis of survival data was performed using the log-rank test. IC50 analyses were performed by non-linear regression and statistical significances were determined using analysis of variance (ANOVA) and F-tests.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A ΔXF *N. benthamiana* plant-produced monoclonal antibody (MAb) specific for West Nile Virus (WNV), the MAb comprising a defined and highly-uniform N-glycoform, wherein the N-glycoform is Man5, Man7, Man8 and/or Man9;

wherein the MAb comprises pHu-E16scFv-CH1-3, wherein the MAb lacks a KDEL sequence, wherein the MAb has reduced antibody-dependent enhancement (ADE) as compared to a mammalian-produced MAb, wherein the MAb has equivalent antigen binding affinity and kinetics, neutralization activity, and in vivo therapeutic activity against a target virus infection as compared to a corresponding antibody produced from non-plant cells, and wherein the MAb comprises a heavy chain (HC) further comprising one or more amino acid mutations that affect Fc receptor or/and C1q binding, wherein the mutations are located at L234, L235 and/or G237 in a human IgG1 isotype HC, or at equivalent locations that correspond to, or align with these positions in a different MAb isotype or subtype, wherein L234, L235 and G237 are equivalent to L255, L256 and G258, respectively, in SEQ ID NO:34.

2. The plant-produced MAb of claim 1, wherein the N-glycoform selectively binds to Fc receptors or C1q.

3. The plant-produced MAb of claim 1, wherein the MAb is pHu-E16scFv-CH1-3.

4. The plant-produced MAb of claim 1, wherein the MAb is Tetra pHu-E16.

5. The plant-produced MAb of claim 1, wherein the HC is a human IgG1 isotype and the mutations are selected from L234AL235A and L234AL235AG237A, or equivalent mutations that correspond to, or align with these positions.

6. The plant-produced MAb of claim 1, wherein the N-glycoform is Man7 and/or Man8.

7. A ΔXF *N. benthamiana* plant-produced monoclonal antibody (MAb) specific for dengue virus (DENV), the MAb comprising a defined and highly-uniform N-glycoform, wherein the N-glycoform is GnGnXF, GnGn or oligomannosidic;

wherein the MAb is pE60 or a single chain variant of DV MAb E60 (scFv-Fc fusion molecule), wherein the MAb lacks a KDEL sequence, wherein the MAb has reduced antibody-dependent enhancement (ADE) as compared to a mammalian-produced MAb, wherein the MAb has equivalent antigen binding affinity and kinetics, neutralization activity, and in vivo therapeutic activity against a target virus infection as compared to a corresponding antibody produced from non-plant cells, wherein the MAb comprises a heavy chain (HC) further comprising one or more amino acid mutations that affect Fc receptor or/and C1q binding, wherein the mutations are located at L234, L235 and/or G237 in a human IgG1 isotype HC, or at equivalent locations that correspond to, or align with these positions in a different MAb isotype or subtype, wherein L234, L235 and G237 are equivalent to L255, L256 and G258, respectively, in SEQ ID NO:34.

8. The plant-produced MAb of claim 7, wherein the HC comprises two or three amino acid mutations.

9. The plant-produced MAb of claim 8, wherein the mutations are L234A and L235A or L234A, L235A and G237A, or equivalent mutations that correspond to, or align with these positions.

10. The plant-produced Mab of claim 7, wherein the N-glycoform is GnGn.

11. The plant-produced Mab of claim 7, wherein the N-glycoform is GnGnXF.

12. The plant-produced Mab of claim 7, wherein the N-glycoform has an oligomannosidic structure.

13. The plant-produced MAb of claim 12, wherein the N-glycoform is Man5, Man7, Man8, and/or Man9.

14. The plant-produced MAb of claim 7, wherein the MAb comprises:

1) a heavy chain comprising SEQ ID NO:18, SEQ ID NO:22 or SEQ ID NO:24;

2) a heavy chain, wherein the heavy chain comprises an amino acid sequence encoded by SEQ ID NO:5, SEQ ID NO:17, SEQ ID NO:21 or SEQ ID NO:23;

3) a light chain, wherein the light chain comprises an amino acid sequence encoded by SEQ ID NO:4;

4) an amino acid sequence encoded by SEQ ID NO:6, SEQ ID NO:25, SEQ ID NO:29 or SEQ ID NO:31; and/or 5) an amino acid sequence comprising SEQ ID NO:26, SEQ ID NO:30 or SEQ ID NO:32.

15. The plant-produced MAb of claim 7, wherein the MAb comprises a light chain, the light chain comprising an alanine-serine (AS) peptide between the variable and constant domains of the light chain.

16. The plant-produced MAb of claim 1, wherein the MAb comprises an amino acid sequence encoded by SEQ ID NO:3.

* * * * *

SEQUENCE LISTING

```
<160> NUMBER OF SEQ ID NOS: 41

<210> SEQ ID NO 1
<211> LENGTH: 702
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

atgggatggt cttgtatcat ccttttcttg gttgcaacag ctactggtgt tcattctgat      60

atcgttatga cacaatctcc agattctttg gctgtttctc ttggagagag ggctactatc     120

aattgcaagg cttctcaaga tgtttctact gctgttgctt ggtaccaaca gaaacctgga     180

cagccaccaa aacttcttat ctcttgggca tctactaggc acactggagt tccagataga     240
```

-continued

```
ttttctggat ctggatctgg aacagatttc actcttacta tctcatctct tcaagctgag    300

gatgttgcag tttattactg tcagcaacat tatacaactc cacttacttt cggacaagga    360

actaagttgg agatcaaaag aactgttgct gcaccatctg ttttcatctt ccctccatct    420

gatgagcagt tgaaatctgg aactgcttct gttgtgtgcc ttcttaataa cttctatcct    480

agagaggcta aagttcagtg gaaggtggat aacgcacttc aatctggtaa ctctcaagag    540

tctgttacag agcaagattc taaggactca acttactctc tttcatctac acttactttg    600

tcaaaagcag attacgagaa acacaaagtt tacgcatgcg aagttactca tcaaggactt    660

tcttcaccag ttacaaagtc tttcaataga ggagagtgtt aa                        702
```

<210> SEQ ID NO 2
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
atgggatggt cttgtatcat ccttttcttg gttgcaacag ctactggtgt tcattctcaa     60

gttcaattgg tgcagtcagg tgctgaggtg aagaaaccag gtgcttcagt taaggtttct    120

tgtaaggctt ctggttacac attcacagat tattggattg aatgggtgag acaagctcct    180

ggtcagggtc ttgagtggat gggagatatt ctttgtggaa ctggaagaac tagatacaac    240

gagaaactta aggctagagt tactatgact gctgatacct ctacatctac tgcttacatg    300

gaacttagat ctttgagatc agatgacact gctgtgtact attgtgctag gtcagcttct    360

tatggagact acgctgacta ttggggacaa ggtactactg ttactgtgtc ttctgcttct    420

accaagggac cttctgtttt tccacttgct ccttcttcta agtctacttc tggtggaact    480

gctgctttgg gttgtttggt gaaagattac tttcctgagc cagtgaccgt ttcttggaac    540

tcaggtgctc ttacatctgg tgttcatact ttcccagctg ttcttcaatc ttcaggactt    600

tactcacttt cttctgttgt taccgttcct tcttcaagct tgggcactca gacctacatc    660

tgcaatgtga atcacaaacc cagcaacacc aaggttgaca agaaagttga gcccaagtct    720

tgtgacaaga ctcatacgtg tccaccgtgc ccagcacctg aacttcttgg aggaccgtca    780

gtcttcttgt ttcctccaaa gcctaaggat accttgatga tctccaggac tcctgaagtc    840

acatgtgtag ttgtggatgt gagccatgaa gatcctgagg tgaagttcaa ctggtatgtg    900

gatggtgtgg aagtgcacaa tgccaagaca aagccgagag aggaacagta caacagcacg    960

tacagggttg tctcagttct cactgttctc catcaagatt ggttgaatgg caaagagtac   1020

aagtgcaagg tctccaacaa agccctccca gcccccattg agaagaccat ttccaaagcg   1080

aaagggcaac cccgtgaacc acaagtgtac acacttcctc catctcgcga tgaactgacc   1140

aagaaccagg tcagcttgac ttgcctggtg aaaggcttct atccctctga catagctgta   1200

gagtgggaga gcaatgggca accggagaac aactacaaga ctacacctcc cgttctcgat   1260

tctgacggct ccttcttcct ctacagcaag ctcacagtgg acaagagcag gtggcaacaa   1320

gggaatgtct tctcatgctc cgtgatgcat gaggctcttc acaatcacta cacacagaag   1380

agtctctcct tgtctccggg taaatga                                        1407
```

<210> SEQ ID NO 3
<211> LENGTH: 1781
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 3

```
atgggatggt cttgtatcat ccttttcttg gttgcaacag ctactggtgt tcattctcaa     60

gttcaattgg tgcagtcagg tgctgaggtg aagaaaccag gtgcttcagt taaggtttct    120

tgtaaggctt ctggttacac attcacagat tattggattg aatgggtgag acaagctcct    180

ggtcagggtc ttgagtggat gggagatatt ctttgtggaa ctggaagaac tagatacaac    240

gagaaactta aggctagagt tactatgact gctgatacct ctacatctac tgcttacatg    300

gaacttagat ctttgagatc agatgacact gctgtgtact attgtgctag gtcagcttct    360

tatggagact acgctgacta ttggggacaa ggtactactg ttactgtgtc ttctggttca    420

acttcaggag gaggatcagg tggtggttca ggaggtggag gatcttctga tatcgttatg    480

acacaatctc cagattcttt ggctgtttct cttggagaga gggctactat caattgcaag    540

gcttctcaag atgtttctac tgctgttgct tggtaccaac agaaacctgg acagccacca    600

aaacttctta tctcttgggc atctactagg cacactggag ttccagatag attttctgga    660

tctggatctg gaacagattt cactcttact atctcatctc ttcaagctga ggatgttgca    720

gtttattact gtcagcaaca ttatacaact ccacttactt tcggacaagg aactaagttg    780

gagatcaaag ctagcaccaa gggaccttct gtttttccac ttgctccttc ttctaagtct    840

acttctggtg gaactgctgc tttgggttgt ttggtgaaag attactttcc tgagccagtg    900

accgtttctt ggaactcagg tgctcttaca tctggtgttc atactttccc agctgttctt    960

caatcttcag gactttactc actttcttct gttgttaccg ttccttcttc aagcttgggc   1020

actcagacct acatctgcaa tgtgaatcac aaacccagca acaccaaggt tgacaagaaa   1080

gttgagccca agtcttgtga caagactcat acgtgtccac cgtgcccagc acctgaactt   1140

cttggaggac cgtcagtctt cttgtttcct ccaaagccta aggatacctt gatgatctcc   1200

aggactcctg aagtcacatg tgtagttgtg gatgtgagcc atgaagatcc tgaggtgaag   1260

ttcaactggt atgtggatgg tgtggaagtg cacaatgcca agacaaagcc gagagaggaa   1320

cagtacaaca gcacgtacag ggttgtctca gttctcactg ttctccatca agattggttg   1380

aatggcaaag agtacaagtg caaggtctcc aacaaaccct cccagccccc attgagaaga   1440

ccatttccaa agcgaaaggg caaccccgtg aaccacaagt gtacacactt cctccatctc   1500

gcgatgaact gaccaagaac caggtcagct tgacttgcct ggtgaaaggc ttctatccct   1560

ctgacatagc tgtagagtgg gagagcaatg ggcaaccgga gaacaactac aagactacac   1620

ctcccgttct cgattctgac ggctccttct tcctctacag caagctcaca gtggacaaga   1680

gcaggtggca acaagggaat gtcttctcat gctccgtgat gcatgaggct cttcacaatc   1740

actacacaca gaagagtctc tccttgtctc cgggtaaatg a                        1781
```

<210> SEQ ID NO 4
<211> LENGTH: 708
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 4

```
atgggatggt cttgtatcat ccttttcttg gttgcaacag ctactggtgt tcattctgac     60
```

-continued atcctgatga cccaatctcc atcctccatg tctgtatctc tgggagactc agtcagcatc 120
acttgccatg caagtcaggg cattagcggt aatatagggt ggttgcagca gaaaccaggg 180
aaatcattta agggcctgat ctatcatgga accaacttgg aagagggagt tccatcaagg 240
ttcagtggca gtggatctgg agcagattat tctctcacca tcagcagcct ggagtctgaa 300
gattttgcag actattactg tgtacagtat ggtcagtttc ctccgacgtt cggtggaggc 360
accaagctgg aaatcaaagc tagcagaact gttgctgcac catctgtttt catcttccct 420
ccatctgatg agcagttgaa atctggaact gcttctgttg tgtgccttct taataacttc 480
tatcctagag aggctaaagt tcagtggaag gtggataacg cacttcaatc tggtaactct 540
caagagtctg ttacagagca agattctaag gactcaactt actctctttc atctacactt 600
actttgtcaa aagcagatta cgagaaacac aaagtttacg catgcgaagt tactcatcaa 660
ggactttctt caccagttac aaagtctttc aatagaggag agtgttaa 708

<210> SEQ ID NO 5
<211> LENGTH: 1404
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5
atgggatggt cttgtatcat ccttttcttg gttgcaacag ctactggtgt tcattctgag 60
gtccaggtgc aacagtctgg acctgaactg gtgacgcctg ggcctcagt gaagatatcc 120 tgcaagactt ctggatacac tttcactgaa tataccgtcc actgggtgaa gcagagccat 180
ggaaagagcc ttgagtggat tggaggcatt aatcctacca gtggtggtac taactacaac 240
cagaggttca ggggcaaggc cacattgact gtagacaggt cctccagcac agcctacatg 300
gagctccgca gcctgacatc tgaggattct gcagtctatt tttgtgcagg aaccctctat 360
ggctaccctt ttgacttctg gggccaaggc accactctca cagtctcctc agctagcacc 420
aagggacctt ctgtttttcc acttgctcct tcttctaagt ctacttctgg tggaactgct 480
gctttgggtt gtttggtgaa agattacttt cctgagccag tgaccgtttc ttggaactca 540
ggtgctctta catctggtgt tcatactttc ccagctgttc ttcaatcttc aggactttac 600
tcactttctt ctgttgttac cgttccttct tcaagcttgg gcactcagac ctacatctgc 660
aatgtgaatc acaaacccag caacaccaag gttgacaaga aagttgagcc caagtcttgt 720
gacaagactc atacgtgtcc accgtgccca gcacctgaac ttcttggagg accgtcagtc 780
ttcttgtttc ctccaaagcc taaggatacc ttgatgatct ccaggactcc tgaagtcaca 840
tgtgtagttg tggatgtgag ccatgaagat cctgaggtga agttcaactg gtatgtggat 900
ggtgtggaag tgcacaatgc caagacaaag ccgagagagg aacagtacaa cagcacgtac 960
agggttgtct cagttctcac tgttctccat caagattggt tgaatggcaa agagtacaag 1020
tgcaaggtct ccaacaaagc cctcccagcc cccattgaga agaccatttc caaagcgaaa 1080
gggcaacccc gtgaaccaca agtgtacaca cttcctccat ctcgcgatga actgaccaag 1140
aaccaggtca gcttgacttg cctggtgaaa ggcttctatc cctctgacat agctgtagag 1200
tgggagagca atgggcaacc ggagaacaac tacaagacta cacctcccgt tctcgattct 1260
gacggctcct tcttcctcta cagcaagctc acagtggaca agagcaggtg gcaacaaggg 1320
aatgtcttct catgctccgt gatgcatgag gctcttcaca atcactacac acagaagagt 1380
ctctccttgt ctccgggtaa atga 1404

<210> SEQ ID NO 6
<211> LENGTH: 1832
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6
atgggatggt cttgtatcat ccttttcttg gttgcaacag ctactggtgt tcattctgag 60
gtccaggtgc aacagtctgg acctgaactg gtgacgcctg gggcctcagt gaagatatcc 120
tgcaagactt ctggatacac tttcactgaa tataccgtcc actgggtgaa gcagagccat 180
ggaaagagcc ttgagtggat tggaggcatt aatcctacca gtggtggtac taactacaac 240
cagaggttca ggggcaaggc cacattgact gtagacaggt cctccagcac agcctacatg 300
gagctccgca gcctgacatc tgaggattct gcagtctatt tttgtgcagg aaccctctat 360
ggctaccctt ttgacttctg gggccaaggc accactctca cagtctcctc aggttcaact 420
tcaggaggag gatcaggtgg tggttcagga ggtggaggat cttctggatg gtcttgtatc 480
atccttttct tggttgcaac agctactggt gttcattctg acatcctgat gacccaatct 540
ccatcctcca tgtctgtatc tctgggagac tcagtcagca tcacttgcca tgcaagtcag 600
ggcattagcg gtaatatagg gtggttgcag cagaaaccag ggaaatcatt taagggcctg 660
atctatcatg gaaccaactt ggaagaggga gttccatcaa ggttcagtgg cagtggatct 720
ggagcagatt attctctcac catcagcagc ctggagtctg aagattttgc agactattac 780
tgtgtacagt atggtcagtt tcctccgacg ttcggtggag gcaccaagct ggaaatcaaa 840
gcagcaccaa gggaccttct gtttttccac ttgctccttc ttctaagtct acttctggtg 900
gaactgctgc tttgggttgt ttggtgaaag attactttcc tgagccagtg accgtttctt 960
ggaactcagg tgctcttaca tctggtgttc atactttccc agctgttctt caatcttcag 1020
gactttactc actttcttct gttgttaccg ttccttcttc aagcttgggc actcagacct 1080
acatctgcaa tgtgaatcac aaacccagca acaccaaggt tgacaagaaa gttgagccca 1140
agtcttgtga caagactcat acgtgtccac cgtgcccagc acctgaactt cttggaggac 1200
cgtcagtctt cttgtttcct ccaaagccta aggatacctt gatgatctcc aggactcctg 1260
aagtcacatg tgtagttgtg gatgtgagcc atgaagatcc tgaggtgaag ttcaactggt 1320
atgtggatgg tgtggaagtg cacaatgcca agacaaagcc gagagaggaa cagtacaaca 1380
gcacgtacag ggttgtctca gttctcactg ttctccatca agattggttg aatggcaaag 1440
agtacaagtg caaggtctcc aacaaagccc tcccagcccc cattgagaag accatttcca 1500
aagcgaaagg gcaaccccgt gaaccacaag tgtacacact tcctccatct cgcgatgaac 1560
tgaccaagaa ccaggtcagc ttgacttgcc tggtgaaagg cttctatccc tctgacatag 1620
ctgtagagtg ggagagcaat gggcaaccgg agaacaacta caagactaca cctcccgttc 1680
tcgattctga cggctccttc ttcctctaca gcaagctcac agtggacaag agcaggtggc 1740
aacaagggaa tgtcttctca tgctccgtga tgcatgaggc tcttcacaat cactacacac 1800
agaagagtct ctccttgtct ccgggtaaat ga 1832

<210> SEQ ID NO 7
<211> LENGTH: 4

-continued

<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: His or Lys

<400> SEQUENCE: 7

Xaa Asp Glu Leu
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Lys Asp Glu Leu
1

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
gaattcacaa tgggatgg 18

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
cctcctgaag ttgaaccaga agacacagta acagtag 37

<210> SEQ ID NO 11
<211> LENGTH: 74
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
ggttcaactt caggaggagg atcaggtggt ggttcaggag gtggaggatc ttctgatatc 60
gttatgacac aatc 74

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
tgctagcttt gatctccaac ttagttcc 28

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
ttggttgcaa cagctactgg tgttcattct gaggtccagg tgcaacag 48

<210> SEQ ID NO 14
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
agaattcaca atgggatggt cttgtatcat ccttttcttg gttgcaacag c 51

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
ttggttgcaa cagctactgg tgttcattct gacatcctga tgacccaatc 50

<210> SEQ ID NO 16
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
agaattcaca atgggatggt cttgtatcat ccttttcttg gttgcaacag c 51

<210> SEQ ID NO 17
<211> LENGTH: 1419
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17
gaattcacaa tgggatggtc ttgtatcatc cttttcttgg ttgcaacagc tactggtgtt 60
cattctgagg tccaggtgca acagtctgga cctgaactgg tgacgcctgg ggcctcagtg 120
aagatatcct gcaagacttc tggatacact ttcactgaat ataccgtcca ctgggtgaag 180
cagagccatg gaaagagcct tgagtggatt ggaggcatta atcctaccag tggtggtact 240
aactacaacc agaggttcag gggcaaggcc acattgactg tagacaggtc ctccagcaca 300
gcctacatgg agctccgcag cctgacatct gaggattctg cagtctattt ttgtgcagga 360

-continued

```
accctctatg gctacccttt tgacttctgg ggccaaggca ccactctcac agtctcctca    420

gctagcacca agggaccttc tgtttttcca cttgctcctt cttctaagtc tacttctggt    480

ggaactgctg ctttgggttg tttggtgaaa gattactttc ctgagccagt gaccgtttct    540

tggaactcag gtgctcttac atctggtgtt catactttcc cagctgttct tcaatcttca    600

ggactttact cactttcttc tgttgttacc gttccttctt caagcttggg cactcagacc    660

tacatctgca atgtgaatca caaacccagc aacaccaagg ttgacaagaa agttgagccc    720

aagtcttgtg acaagactca tacgtgtcca ccgtgcccag cacctgaact tcttggagga    780

ccgtcagtct tcttgtttcc tccaaagcct aaggatacct tgatgatctc caggactcct    840

gaagtcacat gtgtagttgt ggatgtgagc catgaagatc ctgaggtgaa gttcaactgg    900

tatgtggatg gtgtggaagt gcacaatgcc aagacaaagc cgagagagga acagtacaac    960

agcacgtaca gggttgtctc agttctcact gttctccatc aagattggtt gaatggcaaa   1020

gagtacaagt gcaaggtctc caacaaagcc ctcccagccc ccattgagaa gaccatttcc   1080

aaagcgaaag ggcaaccccg tgaaccacaa gtgtacacac ttcctccatc tcgcgatgaa   1140

ctgaccaaga accaggtcag cttgacttgc ctggtgaaag gcttctatcc ctctgacata   1200

gctgtagagt gggagagcaa tggcaaccg gagaacaact acaagactac acctcccgtt    1260

ctcgattctg acggctcctt cttcctctac agcaagctca cagtggacaa gagcaggtgg   1320

caacaaggga atgtcttctc atgctccgtg atgcatgagg ctcttcacaa tcactacaca   1380

cagaagagtc tctccttgtc tccgggtaaa tgaggatcc                          1419
```

<210> SEQ ID NO 18
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Met Gly Trp Ser Cys Ile Ile Leu Phe Leu Val Ala Thr Ala Thr Gly
1               5                   10                  15

Val His Ser Glu Val Gln Val Gln Gln Ser Gly Pro Glu Leu Val Thr
            20                  25                  30

Pro Gly Ala Ser Val Lys Ile Ser Cys Lys Thr Ser Gly Tyr Thr Phe
        35                  40                  45

Thr Glu Tyr Thr Val His Trp Val Lys Gln Ser His Gly Lys Ser Leu
    50                  55                  60

Glu Trp Ile Gly Gly Ile Asn Pro Thr Ser Gly Gly Thr Asn Tyr Asn
65                  70                  75                  80

Gln Arg Phe Arg Gly Lys Ala Thr Leu Thr Val Asp Arg Ser Ser Ser
                85                  90                  95

Thr Ala Tyr Met Glu Leu Arg Ser Leu Thr Ser Glu Asp Ser Ala Val
            100                 105                 110

Tyr Phe Cys Ala Gly Thr Leu Tyr Gly Tyr Pro Phe Asp Phe Trp Gly
        115                 120                 125

Gln Gly Thr Thr Leu Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175
```

```
Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465
```

<210> SEQ ID NO 19
<211> LENGTH: 1419
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
gaattcacaa tgggatggtc ttgtatcatc cttttcttgg ttgcaacagc tactggtgtt     60

cattctgagg tccaggtgca acagtctgga cctgaactgg tgacgcctgg ggcctcagtg    120

aagatatcct gcaagacttc tggatacact ttcactgaat ataccgtcca ctgggtgaag    180

cagagccatg gaaagagcct tgagtggatt ggaggcatta atcctaccag tggtggtact    240

aactacaacc agaggttcag gggcaaggcc acattgactg tagacaggtc ctccagcaca    300
```

-continued

```
gcctacatgg agctccgcag cctgacatct gaggattctg cagtctattt ttgtgcagga    360

accctctatg gctacccttt tgacttctgg ggccaaggca ccactctcac agtctcctca    420

gctagcacca agggaccttc tgtttttcca cttgctcctt cttctaagtc tacttctggt    480

ggaactgctg ctttgggttg tttggtgaaa gattactttc ctgagccagt gaccgtttct    540

tggaactcag gtgctcttac atctggtgtt catactttcc cagctgttct tcaatcttca    600

ggactttact cactttcttc tgttgttacc gttccttctt caagcttggg cactcagacc    660

tacatctgca atgtgaatca caaacccagc aacaccaagg ttgacaagaa agttgagccc    720

aagtcttgtg acaagactca tacgtgtcca ccgtgcccag cacctgaact tcttggagga    780

ccgtcagtct tcttgtttcc tccaaagcct aaggatacct tgatgatctc caggactcct    840

gaagtcacat gtgtagttgt ggatgtgagc catgaagatc ctgaggtgaa gttcaactgg    900

tatgtggatg gtgtggaagt gcacaatgcc aagacaaagc cgagagagga acagtaccaa    960

agcacgtaca gggttgtctc agttctcact gttctccatc aagattggtt gaatggcaaa   1020

gagtacaagt gcaaggtctc caacaaagcc ctcccagccc ccattgagaa gaccatttcc   1080

aaagcgaaag ggcaaccccg tgaaccacaa gtgtacacac ttcctccatc tcgcgatgaa   1140

ctgaccaaga accaggtcag cttgacttgc ctggtgaaag gcttctatcc ctctgacata   1200

gctgtagagt gggagagcaa tgggcaaccg gagaacaact acaagactac acctcccgtt   1260

ctcgattctg acggctcctt cttcctctac agcaagctca cagtggacaa gagcaggtgg   1320

caacaaggga atgtcttctc atgctccgtg atgcatgagg ctcttcacaa tcactacaca   1380

cagaagagtc tctccttgtc tccgggtaaa tgaggatcc                          1419
```

```
<210> SEQ ID NO 20
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Gly Trp Ser Cys Ile Ile Leu Phe Leu Val Ala Thr Ala Thr Gly
1               5                   10                  15

Val His Ser Glu Val Gln Val Gln Gln Ser Gly Pro Glu Leu Val Thr
            20                  25                  30

Pro Gly Ala Ser Val Lys Ile Ser Cys Lys Thr Ser Gly Tyr Thr Phe
        35                  40                  45

Thr Glu Tyr Thr Val His Trp Val Lys Gln Ser His Gly Lys Ser Leu
    50                  55                  60

Glu Trp Ile Gly Gly Ile Asn Pro Thr Ser Gly Gly Thr Asn Tyr Asn
65                  70                  75                  80

Gln Arg Phe Arg Gly Lys Ala Thr Leu Thr Val Asp Arg Ser Ser Ser
                85                  90                  95

Thr Ala Tyr Met Glu Leu Arg Ser Leu Thr Ser Glu Asp Ser Ala Val
            100                 105                 110

Tyr Phe Cys Ala Gly Thr Leu Tyr Gly Tyr Pro Phe Asp Phe Trp Gly
        115                 120                 125

Gln Gly Thr Thr Leu Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160
```

```
Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Gln Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465


<210> SEQ ID NO 21
<211> LENGTH: 1419
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

gaattcacaa tgggatggtc ttgtatcatc cttttcttgg ttgcaacagc tactggtgtt      60

cattctgagg tccaggtgca acagtctgga cctgaactgg tgacgcctgg ggcctcagtg     120

aagatatcct gcaagacttc tggatacact ttcactgaat ataccgtcca ctgggtgaag     180

cagagccatg gaaagagcct tgagtggatt ggaggcatta atcctaccag tggtggtact     240
```

```
aactacaacc agaggttcag gggcaaggcc acattgactg tagacaggtc ctccagcaca    300

gcctacatgg agctccgcag cctgacatct gaggattctg cagtctattt ttgtgcagga    360

accctctatg gctacccttt tgacttctgg ggccaaggca ccactctcac agtctcctca    420

gctagcacca agggaccttc tgtttttcca cttgctcctt cttctaagtc tacttctggt    480

ggaactgctg ctttgggttg tttggtgaaa gattactttc ctgagccagt gaccgtttct    540

tggaactcag gtgctcttac atctggtgtt catactttcc cagctgttct tcaatcttca    600

ggactttact cactttcttc tgttgttacc gttccttctt caagcttggg cactcagacc    660

tacatctgca atgtgaatca caaacccagc aacaccaagg ttgacaagaa agttgagccc    720

aagtcttgtg acaagactca tacgtgtcca ccgtgcccag cacctgaagc tgctggagga    780

ccgtcagtct tcttgtttcc tccaaagcct aaggatacct tgatgatctc caggactcct    840

gaagtcacat gtgtagttgt ggatgtgagc catgaagatc ctgaggtgaa gttcaactgg    900

tatgtggatg gtgtggaagt gcacaatgcc aagacaaagc cgagagagga acagtacaac    960

agcacgtaca gggttgtctc agttctcact gttctccatc aagattggtt gaatggcaaa   1020

gagtacaagt gcaaggtctc caacaaagcc ctcccagccc ccattgagaa gaccatttcc   1080

aaagcgaaag ggcaaccccg tgaaccacaa gtgtacacac ttcctccatc tcgcgatgaa   1140

ctgaccaaga accaggtcag cttgacttgc ctggtgaaag gcttctatcc ctctgacata   1200

gctgtagagt gggagagcaa tggcaaccg gagaacaact acaagactac acctcccgtt   1260

ctcgattctg acggctcctt cttcctctac agcaagctca cagtggacaa gagcaggtgg   1320

caacaaggga atgtcttctc atgctccgtg atgcatgagg ctcttcacaa tcactacaca   1380

cagaagagtc tctccttgtc tccgggtaaa tgaggatcc                          1419
```

<210> SEQ ID NO 22
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Met Gly Trp Ser Cys Ile Ile Leu Phe Leu Val Ala Thr Ala Thr Gly
1               5                   10                  15

Val His Ser Glu Val Gln Val Gln Gln Ser Gly Pro Glu Leu Val Thr
            20                  25                  30

Pro Gly Ala Ser Val Lys Ile Ser Cys Lys Thr Ser Gly Tyr Thr Phe
        35                  40                  45

Thr Glu Tyr Thr Val His Trp Val Lys Gln Ser His Gly Lys Ser Leu
    50                  55                  60

Glu Trp Ile Gly Gly Ile Asn Pro Thr Ser Gly Gly Thr Asn Tyr Asn
65                  70                  75                  80

Gln Arg Phe Arg Gly Lys Ala Thr Leu Thr Val Asp Arg Ser Ser Ser
                85                  90                  95

Thr Ala Tyr Met Glu Leu Arg Ser Leu Thr Ser Glu Asp Ser Ala Val
            100                 105                 110

Tyr Phe Cys Ala Gly Thr Leu Tyr Gly Tyr Pro Phe Asp Phe Trp Gly
        115                 120                 125

Gln Gly Thr Thr Leu Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
```

-continued

```
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Ala Ala Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465
```

<210> SEQ ID NO 23
<211> LENGTH: 1419
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
gaattcacaa tgggatggtc ttgtatcatc cttttcttgg ttgcaacagc tactggtgtt      60

cattctgagg tccaggtgca acagtctgga cctgaactgg tgacgcctgg ggcctcagtg     120

aagatatcct gcaagacttc tggatacact ttcactgaat ataccgtcca ctgggtgaag     180
```

-continued

```
cagagccatg gaaagagcct tgagtggatt ggaggcatta atcctaccag tggtggtact    240

aactacaacc agaggttcag gggcaaggcc acattgactg tagacaggtc ctccagcaca    300

gcctacatgg agctccgcag cctgacatct gaggattctg cagtctattt ttgtgcagga    360

accctctatg gctacccttt tgacttctgg ggccaaggca ccactctcac agtctcctca    420

gctagcacca agggaccttc tgtttttcca cttgctcctt cttctaagtc tacttctggt    480

ggaactgctg ctttgggttg tttggtgaaa gattactttc ctgagccagt gaccgtttct    540

tggaactcag gtgctcttac atctggtgtt catactttcc cagctgttct tcaatcttca    600

ggactttact cactttcttc tgttgttacc gttccttctt caagcttggg cactcagacc    660

tacatctgca atgtgaatca caaacccagc aacaccaagg ttgacaagaa agttgagccc    720

aagtcttgtg acaagactca tacgtgtcca ccgtgcccag cacctgaagc tgctggagca    780

ccgtcagtct tcttgtttcc tccaaagcct aaggatacct tgatgatctc caggactcct    840

gaagtcacat gtgtagttgt ggatgtgagc catgaagatc ctgaggtgaa gttcaactgg    900

tatgtggatg gtgtggaagt gcacaatgcc aagacaaagc cgagagagga acagtacaac    960

agcacgtaca gggttgtctc agttctcact gttctccatc aagattggtt gaatggcaaa   1020

gagtacaagt gcaaggtctc caacaaagcc ctcccagccc ccattgagaa gaccatttcc   1080

aaagcgaaag ggcaaccccg tgaaccacaa gtgtacacac ttcctccatc tcgcgatgaa   1140

ctgaccaaga accaggtcag cttgacttgc ctggtgaaag gcttctatcc ctctgacata   1200

gctgtagagt gggagagcaa tgggcaaccg gagaacaact acaagactac acctcccgtt   1260

ctcgattctg acggctcctt cttcctctac agcaagctca cagtggacaa gagcaggtgg   1320

caacaaggga atgtcttctc atgctccgtg atgcatgagg ctcttcacaa tcactacaca   1380

cagaagagtc tctccttgtc tccgggtaaa tgaggatcc                          1419
```

<210> SEQ ID NO 24
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Met Gly Trp Ser Cys Ile Ile Leu Phe Leu Val Ala Thr Ala Thr Gly
1               5                   10                  15

Val His Ser Glu Val Gln Val Gln Gln Ser Gly Pro Glu Leu Val Thr
            20                  25                  30

Pro Gly Ala Ser Val Lys Ile Ser Cys Lys Thr Ser Gly Tyr Thr Phe
        35                  40                  45

Thr Glu Tyr Thr Val His Trp Val Lys Gln Ser His Gly Lys Ser Leu
    50                  55                  60

Glu Trp Ile Gly Gly Ile Asn Pro Thr Ser Gly Gly Thr Asn Tyr Asn
65                  70                  75                  80

Gln Arg Phe Arg Gly Lys Ala Thr Leu Thr Val Asp Arg Ser Ser Ser
                85                  90                  95

Thr Ala Tyr Met Glu Leu Arg Ser Leu Thr Ser Glu Asp Ser Ala Val
            100                 105                 110

Tyr Phe Cys Ala Gly Thr Leu Tyr Gly Tyr Pro Phe Asp Phe Trp Gly
        115                 120                 125

Gln Gly Thr Thr Leu Thr Val Ser Ser Ala Ser Thr Lys Gly Pro Ser
    130                 135                 140
```

```
Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Ala Ala Gly
                245                 250                 255

Ala Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465
```

<210> SEQ ID NO 25
<211> LENGTH: 1794
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
gaattcacaa tgggatggtc ttgtatcatc cttttcttgg ttgcaacagc tactggtgtt      60

cattctgagg tccaggtgca acagtctgga cctgaactgg tgacgcctgg ggcctcagtg     120
```

-continued

```
aagatatcct gcaagacttc tggatacact ttcactgaat ataccgtcca ctgggtgaag    180

cagagccatg gaaagagcct tgagtggatt ggaggcatta atcctaccag tggtggtact    240

aactacaacc agaggttcag gggcaaggcc acattgactg tagacaggtc ctccagcaca    300

gcctacatgg agctccgcag cctgacatct gaggattctg cagtctattt ttgtgcagga    360

accctctatg gctacccttt tgacttctgg ggccaaggca ccactctcac agtctcctca    420

ggttcaactt caggaggagg atcaggtggt ggttcaggag gtggaggatc ttctgacatc    480

ctgatgaccc aatctccatc ctccatgtct gtatctctgg gagactcagt cagcatcact    540

tgccatgcaa gtcagggcat tagcggtaat atagggtggt tgcagcagaa accagggaaa    600

tcatttaagg gcctgatcta tcatggaacc aacttggaag agggagttcc atcaaggttc    660

agtggcagtg gatctggagc agattattct ctcaccatca gcagcctgga gtctgaagat    720

tttgcagact attactgtgt acagtatggt cagtttcctc cgacgttcgg tggaggcacc    780

aagctggaaa tcaaagctag caccaaggga ccttctgttt ttccacttgc tccttcttct    840

aagtctactt ctggtggaac tgctgctttg ggttgtttgg tgaaagatta ctttcctgag    900

ccagtgaccg tttcttggaa ctcaggtgct cttacatctg gtgttcatac tttcccagct    960

gttcttcaat cttcaggact ttactcactt tcttctgttg ttaccgttcc ttcttcaagc   1020

ttgggcactc agacctacat ctgcaatgtg aatcacaaac ccagcaacac caaggttgac   1080

aagaaagttg agcccaagtc ttgtgacaag actcatacgt gtccaccgtg cccagcacct   1140

gaacttcttg gaggaccgtc agtcttcttg tttcctccaa agcctaagga taccttgatg   1200

atctccagga ctcctgaagt cacatgtgta gttgtggatg tgagccatga agatcctgag   1260

gtgaagttca actggtatgt ggatggtgtg gaagtgcaca atgccaagac aaagccgaga   1320

gaggaacagt acaacagcac gtacagggtt gtctcagttc tcactgttct ccatcaagat   1380

tggttgaatg gcaaagagta caagtgcaag gtctccaaca aagccctccc agcccccatt   1440

gagaagacca tttccaaagc gaaagggcaa ccccgtgaac cacaagtgta cacacttcct   1500

ccatctcgcg atgaactgac caagaaccag gtcagcttga cttgcctggt gaaaggcttc   1560

tatccctctg acatagctgt agagtgggag agcaatgggc aaccggagaa caactacaag   1620

actacacctc ccgttctcga ttctgacggc tccttcttcc tctacagcaa gctcacagtg   1680

gacaagagca ggtggcaaca agggaatgtc ttctcatgct ccgtgatgca tgaggctctt   1740

cacaatcact acacacagaa gagtctctcc ttgtctccgg gtaaatgagg atcc         1794
```

<210> SEQ ID NO 26
<211> LENGTH: 592
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Met Gly Trp Ser Cys Ile Ile Leu Phe Leu Val Ala Thr Ala Thr Gly
1               5                   10                  15

Val His Ser Glu Val Gln Val Gln Gln Ser Gly Pro Glu Leu Val Thr
            20                  25                  30

Pro Gly Ala Ser Val Lys Ile Ser Cys Lys Thr Ser Gly Tyr Thr Phe
        35                  40                  45

Thr Glu Tyr Thr Val His Trp Val Lys Gln Ser His Gly Lys Ser Leu
    50                  55                  60
```

-continued

```
Glu Trp Ile Gly Gly Ile Asn Pro Thr Ser Gly Gly Thr Asn Tyr Asn
65                  70                  75                  80

Gln Arg Phe Arg Gly Lys Ala Thr Leu Thr Val Asp Arg Ser Ser Ser
                85                  90                  95

Thr Ala Tyr Met Glu Leu Arg Ser Leu Thr Ser Glu Asp Ser Ala Val
            100                 105                 110

Tyr Phe Cys Ala Gly Thr Leu Tyr Gly Tyr Pro Phe Asp Phe Trp Gly
        115                 120                 125

Gln Gly Thr Thr Leu Thr Val Ser Ser Gly Ser Thr Ser Gly Gly Gly
    130                 135                 140

Ser Gly Gly Gly Ser Gly Gly Gly Gly Ser Ser Asp Ile Leu Met Thr
145                 150                 155                 160

Gln Ser Pro Ser Ser Met Ser Val Ser Leu Gly Asp Ser Val Ser Ile
                165                 170                 175

Thr Cys His Ala Ser Gln Gly Ile Ser Gly Asn Ile Gly Trp Leu Gln
            180                 185                 190

Gln Lys Pro Gly Lys Ser Phe Lys Gly Leu Ile Tyr His Gly Thr Asn
        195                 200                 205

Leu Glu Glu Gly Val Pro Ser Arg Phe Ser Gly Ser Gly Ser Gly Ala
    210                 215                 220

Asp Tyr Ser Leu Thr Ile Ser Ser Leu Glu Ser Glu Asp Phe Ala Asp
225                 230                 235                 240

Tyr Tyr Cys Val Gln Tyr Gly Gln Phe Pro Pro Thr Phe Gly Gly Gly
                245                 250                 255

Thr Lys Leu Glu Ile Lys Ala Ser Thr Lys Gly Pro Ser Val Phe Pro
            260                 265                 270

Leu Ala Pro Ser Ser Lys Ser Thr Ser Gly Gly Thr Ala Ala Leu Gly
        275                 280                 285

Cys Leu Val Lys Asp Tyr Phe Pro Glu Pro Val Thr Val Ser Trp Asn
    290                 295                 300

Ser Gly Ala Leu Thr Ser Gly Val His Thr Phe Pro Ala Val Leu Gln
305                 310                 315                 320

Ser Ser Gly Leu Tyr Ser Leu Ser Ser Val Val Thr Val Pro Ser Ser
                325                 330                 335

Ser Leu Gly Thr Gln Thr Tyr Ile Cys Asn Val Asn His Lys Pro Ser
            340                 345                 350

Asn Thr Lys Val Asp Lys Lys Val Glu Pro Lys Ser Cys Asp Lys Thr
        355                 360                 365

His Thr Cys Pro Pro Cys Pro Ala Pro Glu Leu Leu Gly Gly Pro Ser
    370                 375                 380

Val Phe Leu Phe Pro Pro Lys Pro Lys Asp Thr Leu Met Ile Ser Arg
385                 390                 395                 400

Thr Pro Glu Val Thr Cys Val Val Val Asp Val Ser His Glu Asp Pro
                405                 410                 415

Glu Val Lys Phe Asn Trp Tyr Val Asp Gly Val Glu Val His Asn Ala
            420                 425                 430

Lys Thr Lys Pro Arg Glu Glu Gln Tyr Asn Ser Thr Tyr Arg Val Val
        435                 440                 445

Ser Val Leu Thr Val Leu His Gln Asp Trp Leu Asn Gly Lys Glu Tyr
    450                 455                 460

Lys Cys Lys Val Ser Asn Lys Ala Leu Pro Ala Pro Ile Glu Lys Thr
465                 470                 475                 480

Ile Ser Lys Ala Lys Gly Gln Pro Arg Glu Pro Gln Val Tyr Thr Leu
```

-continued

```
                485                 490                 495

Pro Pro Ser Arg Asp Glu Leu Thr Lys Asn Gln Val Ser Leu Thr Cys
            500                 505                 510

Leu Val Lys Gly Phe Tyr Pro Ser Asp Ile Ala Val Glu Trp Glu Ser
        515                 520                 525

Asn Gly Gln Pro Glu Asn Asn Tyr Lys Thr Thr Pro Pro Val Leu Asp
    530                 535                 540

Ser Asp Gly Ser Phe Phe Leu Tyr Ser Lys Leu Thr Val Asp Lys Ser
545                 550                 555                 560

Arg Trp Gln Gln Gly Asn Val Phe Ser Cys Ser Val Met His Glu Ala
                565                 570                 575

Leu His Asn His Tyr Thr Gln Lys Ser Leu Ser Leu Ser Pro Gly Lys
            580                 585                 590


<210> SEQ ID NO 27
<211> LENGTH: 1794
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

gaattcacaa tgggatggtc ttgtatcatc cttttcttgg ttgcaacagc tactggtgtt     60

cattctgagg tccaggtgca acagtctgga cctgaactgg tgacgcctgg ggcctcagtg    120

aagatatcct gcaagacttc tggatacact ttcactgaat ataccgtcca ctgggtgaag    180

cagagccatg gaaagagcct tgagtggatt ggaggcatta atcctaccag tggtggtact    240

aactacaacc agaggttcag gggcaaggcc acattgactg tagacaggtc ctccagcaca    300

gcctacatgg agctccgcag cctgacatct gaggattctg cagtctattt ttgtgcagga    360

accctctatg gctacccttt tgacttctgg ggccaaggca ccactctcac agtctcctca    420

ggttcaactt caggaggagg atcaggtggt ggttcaggag gtggaggatc ttctgacatc    480

ctgatgaccc aatctccatc ctccatgtct gtatctctgg gagactcagt cagcatcact    540

tgccatgcaa gtcagggcat tagcggtaat atagggtggt tgcagcagaa accagggaaa    600

tcatttaagg gcctgatcta tcatggaacc aacttggaag agggagttcc atcaaggttc    660

agtggcagtg gatctggagc agattattct ctcaccatca gcagcctgga gtctgaagat    720

tttgcagact attactgtgt acagtatggt cagtttcctc cgacgttcgg tggaggcacc    780

aagctggaaa tcaaagctag caccaaggga ccttctgttt ttccacttgc tccttcttct    840

aagtctactt ctggtggaac tgctgctttg ggttgtttgg tgaaagatta ctttcctgag    900

ccagtgaccg tttcttggaa ctcaggtgct cttacatctg gtgttcatac tttcccagct    960

gttcttcaat cttcaggact ttactcactt tcttctgttg ttaccgttcc ttcttcaagc   1020

ttgggcactc agacctacat ctgcaatgtg aatcacaaac ccagcaacac caaggttgac   1080

aagaaagttg agcccaagtc ttgtgacaag actcatacgt gtccaccgtg cccagcacct   1140

gaacttcttg gaggaccgtc agtcttcttg tttcctccaa agcctaagga taccttgatg   1200

atctccagga ctcctgaagt cacatgtgta gttgtggatg tgagccatga agatcctgag   1260

gtgaagttca actggtatgt ggatggtgtg gaagtgcaca atgccaagac aaagccgaga   1320

gaggaacagt accaaagcac gtacagggtt gtctcagttc tcactgttct ccatcaagat   1380

tggttgaatg gcaaagagta caagtgcaag gtctccaaca aagccctccc agcccccatt   1440
```

-continued

```
gagaagacca tttccaaagc gaaagggcaa ccccgtgaac cacaagtgta cacacttcct   1500

ccatctcgcg atgaactgac caagaaccag gtcagcttga cttgcctggt gaaaggcttc   1560

tatccctctg acatagctgt agagtgggag agcaatgggc aaccggagaa caactacaag   1620

actacacctc ccgttctcga ttctgacggc tccttcttcc tctacagcaa gctcacagtg   1680

gacaagagca ggtggcaaca agggaatgtc ttctcatgct ccgtgatgca tgaggctctt   1740

cacaatcact acacacagaa gagtctctcc ttgtctccgg gtaaatgagg atcc         1794
```

<210> SEQ ID NO 28
<211> LENGTH: 592
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Met Gly Trp Ser Cys Ile Ile Leu Phe Leu Val Ala Thr Ala Thr Gly
1               5                   10                  15

Val His Ser Glu Val Gln Val Gln Gln Ser Gly Pro Glu Leu Val Thr
            20                  25                  30

Pro Gly Ala Ser Val Lys Ile Ser Cys Lys Thr Ser Gly Tyr Thr Phe
        35                  40                  45

Thr Glu Tyr Thr Val His Trp Val Lys Gln Ser His Gly Lys Ser Leu
    50                  55                  60

Glu Trp Ile Gly Gly Ile Asn Pro Thr Ser Gly Gly Thr Asn Tyr Asn
65                  70                  75                  80

Gln Arg Phe Arg Gly Lys Ala Thr Leu Thr Val Asp Arg Ser Ser Ser
                85                  90                  95

Thr Ala Tyr Met Glu Leu Arg Ser Leu Thr Ser Glu Asp Ser Ala Val
            100                 105                 110

Tyr Phe Cys Ala Gly Thr Leu Tyr Gly Tyr Pro Phe Asp Phe Trp Gly
        115                 120                 125

Gln Gly Thr Thr Leu Thr Val Ser Ser Gly Ser Thr Ser Gly Gly Gly
    130                 135                 140

Ser Gly Gly Gly Ser Gly Gly Gly Gly Ser Ser Asp Ile Leu Met Thr
145                 150                 155                 160

Gln Ser Pro Ser Ser Met Ser Val Ser Leu Gly Asp Ser Val Ser Ile
                165                 170                 175

Thr Cys His Ala Ser Gln Gly Ile Ser Gly Asn Ile Gly Trp Leu Gln
            180                 185                 190

Gln Lys Pro Gly Lys Ser Phe Lys Gly Leu Ile Tyr His Gly Thr Asn
        195                 200                 205

Leu Glu Glu Gly Val Pro Ser Arg Phe Ser Gly Ser Gly Ser Gly Ala
    210                 215                 220

Asp Tyr Ser Leu Thr Ile Ser Ser Leu Glu Ser Glu Asp Phe Ala Asp
225                 230                 235                 240

Tyr Tyr Cys Val Gln Tyr Gly Gln Phe Pro Pro Thr Phe Gly Gly Gly
                245                 250                 255

Thr Lys Leu Glu Ile Lys Ala Ser Thr Lys Gly Pro Ser Val Phe Pro
            260                 265                 270

Leu Ala Pro Ser Ser Lys Ser Thr Ser Gly Gly Thr Ala Ala Leu Gly
        275                 280                 285

Cys Leu Val Lys Asp Tyr Phe Pro Glu Pro Val Thr Val Ser Trp Asn
    290                 295                 300
```

Ser Gly Ala Leu Thr Ser Gly Val His Thr Phe Pro Ala Val Leu Gln
305 310 315 320

Ser Ser Gly Leu Tyr Ser Leu Ser Ser Val Val Thr Val Pro Ser Ser
325 330 335

Ser Leu Gly Thr Gln Thr Tyr Ile Cys Asn Val Asn His Lys Pro Ser
340 345 350

Asn Thr Lys Val Asp Lys Lys Val Glu Pro Lys Ser Cys Asp Lys Thr
355 360 365

His Thr Cys Pro Pro Cys Pro Ala Pro Glu Leu Leu Gly Gly Pro Ser
370 375 380

Val Phe Leu Phe Pro Pro Lys Pro Lys Asp Thr Leu Met Ile Ser Arg
385 390 395 400

Thr Pro Glu Val Thr Cys Val Val Val Asp Val Ser His Glu Asp Pro
405 410 415

Glu Val Lys Phe Asn Trp Tyr Val Asp Gly Val Glu Val His Asn Ala
420 425 430

Lys Thr Lys Pro Arg Glu Glu Gln Tyr Gln Ser Thr Tyr Arg Val Val
435 440 445

Ser Val Leu Thr Val Leu His Gln Asp Trp Leu Asn Gly Lys Glu Tyr
450 455 460

Lys Cys Lys Val Ser Asn Lys Ala Leu Pro Ala Pro Ile Glu Lys Thr
465 470 475 480

Ile Ser Lys Ala Lys Gly Gln Pro Arg Glu Pro Gln Val Tyr Thr Leu
485 490 495

Pro Pro Ser Arg Asp Glu Leu Thr Lys Asn Gln Val Ser Leu Thr Cys
500 505 510

Leu Val Lys Gly Phe Tyr Pro Ser Asp Ile Ala Val Glu Trp Glu Ser
515 520 525

Asn Gly Gln Pro Glu Asn Asn Tyr Lys Thr Thr Pro Pro Val Leu Asp
530 535 540

Ser Asp Gly Ser Phe Phe Leu Tyr Ser Lys Leu Thr Val Asp Lys Ser
545 550 555 560

Arg Trp Gln Gln Gly Asn Val Phe Ser Cys Ser Val Met His Glu Ala
565 570 575

Leu His Asn His Tyr Thr Gln Lys Ser Leu Ser Leu Ser Pro Gly Lys
580 585 590

<210> SEQ ID NO 29
<211> LENGTH: 1794
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 29
gaattcacaa tgggatggtc ttgtatcatc cttttcttgg ttgcaacagc tactggtgtt 60
cattctgagg tccaggtgca acagtctgga cctgaactgg tgacgcctgg ggcctcagtg 120
aagatatcct gcaagacttc tggatacact ttcactgaat ataccgtcca ctgggtgaag 180
cagagccatg gaaagagcct tgagtggatt ggaggcatta atcctaccag tggtggtact 240
aactacaacc agaggttcag gggcaaggcc acattgactg tagacaggtc ctccagcaca 300
gcctacatgg agctccgcag cctgacatct gaggattctg cagtctattt ttgtgcagga 360
accctctatg gctacccttt tgacttctgg ggccaaggca ccactctcac agtctcctca 420

```
ggttcaactt caggaggagg atcaggtggt ggttcaggag gtggaggatc ttctgacatc    480

ctgatgaccc aatctccatc ctccatgtct gtatctctgg gagactcagt cagcatcact    540

tgccatgcaa gtcagggcat tagcggtaat atagggtggt tgcagcagaa accagggaaa    600

tcatttaagg gcctgatcta tcatggaacc aacttggaag agggagttcc atcaaggttc    660

agtggcagtg gatctggagc agattattct ctcaccatca gcagcctgga gtctgaagat    720

tttgcagact attactgtgt acagtatggt cagtttcctc cgacgttcgg tggaggcacc    780

aagctggaaa tcaaagctag caccaaggga ccttctgttt ttccacttgc tccttcttct    840

aagtctactt ctggtggaac tgctgctttg ggttgtttgg tgaaagatta ctttcctgag    900

ccagtgaccg tttcttggaa ctcaggtgct cttacatctg gtgttcatac tttcccagct    960

gttcttcaat cttcaggact ttactcactt tcttctgttg ttaccgttcc ttcttcaagc   1020

ttgggcactc agacctacat ctgcaatgtg aatcacaaac ccagcaacac caaggttgac   1080

aagaaagttg agcccaagtc ttgtgacaag actcatacgt gtccaccgtg cccagcacct   1140

gaagctgctg gaggaccgtc agtcttcttg tttcctccaa agcctaagga taccttgatg   1200

atctccagga ctcctgaagt cacatgtgta gttgtggatg tgagccatga agatcctgag   1260

gtgaagttca actggtatgt ggatggtgtg gaagtgcaca atgccaagac aaagccgaga   1320

gaggaacagt acaacagcac gtacagggtt gtctcagttc tcactgttct ccatcaagat   1380

tggttgaatg gcaaagagta caagtgcaag gtctccaaca aagccctccc agcccccatt   1440

gagaagacca tttccaaagc gaaagggcaa ccccgtgaac cacaagtgta cacacttcct   1500

ccatctcgcg atgaactgac caagaaccag gtcagcttga cttgcctggt gaaaggcttc   1560

tatccctctg acatagctgt agagtgggag agcaatgggc aaccggagaa caactacaag   1620

actacacctc ccgttctcga ttctgacggc tccttcttcc tctacagcaa gctcacagtg   1680

gacaagagca ggtggcaaca agggaatgtc ttctcatgct ccgtgatgca tgaggctctt   1740

cacaatcact acacacagaa gagtctctcc ttgtctccgg gtaaatgagg atcc         1794
```

```
<210> SEQ ID NO 30
<211> LENGTH: 592
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Gly Trp Ser Cys Ile Ile Leu Phe Leu Val Ala Thr Ala Thr Gly
1               5                   10                  15

Val His Ser Glu Val Gln Val Gln Gln Ser Gly Pro Glu Leu Val Thr
            20                  25                  30

Pro Gly Ala Ser Val Lys Ile Ser Cys Lys Thr Ser Gly Tyr Thr Phe
        35                  40                  45

Thr Glu Tyr Thr Val His Trp Val Lys Gln Ser His Gly Lys Ser Leu
    50                  55                  60

Glu Trp Ile Gly Gly Ile Asn Pro Thr Ser Gly Gly Thr Asn Tyr Asn
65                  70                  75                  80

Gln Arg Phe Arg Gly Lys Ala Thr Leu Thr Val Asp Arg Ser Ser Ser
                85                  90                  95

Thr Ala Tyr Met Glu Leu Arg Ser Leu Thr Ser Glu Asp Ser Ala Val
            100                 105                 110
```

-continued

```
Tyr Phe Cys Ala Gly Thr Leu Tyr Gly Tyr Pro Phe Asp Phe Trp Gly
        115                 120                 125

Gln Gly Thr Thr Leu Thr Val Ser Ser Gly Ser Thr Ser Gly Gly Gly
    130                 135                 140

Ser Gly Gly Gly Ser Gly Gly Gly Gly Ser Ser Asp Ile Leu Met Thr
145                 150                 155                 160

Gln Ser Pro Ser Ser Met Ser Val Ser Leu Gly Asp Ser Val Ser Ile
                165                 170                 175

Thr Cys His Ala Ser Gln Gly Ile Ser Gly Asn Ile Gly Trp Leu Gln
            180                 185                 190

Gln Lys Pro Gly Lys Ser Phe Lys Gly Leu Ile Tyr His Gly Thr Asn
        195                 200                 205

Leu Glu Glu Gly Val Pro Ser Arg Phe Ser Gly Ser Gly Ser Gly Ala
    210                 215                 220

Asp Tyr Ser Leu Thr Ile Ser Ser Leu Glu Ser Glu Asp Phe Ala Asp
225                 230                 235                 240

Tyr Tyr Cys Val Gln Tyr Gly Gln Phe Pro Pro Thr Phe Gly Gly Gly
                245                 250                 255

Thr Lys Leu Glu Ile Lys Ala Ser Thr Lys Gly Pro Ser Val Phe Pro
            260                 265                 270

Leu Ala Pro Ser Ser Lys Ser Thr Ser Gly Gly Thr Ala Ala Leu Gly
        275                 280                 285

Cys Leu Val Lys Asp Tyr Phe Pro Glu Pro Val Thr Val Ser Trp Asn
    290                 295                 300

Ser Gly Ala Leu Thr Ser Gly Val His Thr Phe Pro Ala Val Leu Gln
305                 310                 315                 320

Ser Ser Gly Leu Tyr Ser Leu Ser Ser Val Val Thr Val Pro Ser Ser
                325                 330                 335

Ser Leu Gly Thr Gln Thr Tyr Ile Cys Asn Val Asn His Lys Pro Ser
            340                 345                 350

Asn Thr Lys Val Asp Lys Lys Val Glu Pro Lys Ser Cys Asp Lys Thr
        355                 360                 365

His Thr Cys Pro Pro Cys Pro Ala Pro Glu Ala Ala Gly Gly Pro Ser
    370                 375                 380

Val Phe Leu Phe Pro Pro Lys Pro Lys Asp Thr Leu Met Ile Ser Arg
385                 390                 395                 400

Thr Pro Glu Val Thr Cys Val Val Val Asp Val Ser His Glu Asp Pro
                405                 410                 415

Glu Val Lys Phe Asn Trp Tyr Val Asp Gly Val Glu Val His Asn Ala
            420                 425                 430

Lys Thr Lys Pro Arg Glu Glu Gln Tyr Asn Ser Thr Tyr Arg Val Val
        435                 440                 445

Ser Val Leu Thr Val Leu His Gln Asp Trp Leu Asn Gly Lys Glu Tyr
    450                 455                 460

Lys Cys Lys Val Ser Asn Lys Ala Leu Pro Ala Pro Ile Glu Lys Thr
465                 470                 475                 480

Ile Ser Lys Ala Lys Gly Gln Pro Arg Glu Pro Gln Val Tyr Thr Leu
                485                 490                 495

Pro Pro Ser Arg Asp Glu Leu Thr Lys Asn Gln Val Ser Leu Thr Cys
            500                 505                 510

Leu Val Lys Gly Phe Tyr Pro Ser Asp Ile Ala Val Glu Trp Glu Ser
        515                 520                 525

Asn Gly Gln Pro Glu Asn Asn Tyr Lys Thr Thr Pro Pro Val Leu Asp
```

-continued

```
    530                 535                 540

Ser Asp Gly Ser Phe Phe Leu Tyr Ser Lys Leu Thr Val Asp Lys Ser
545                 550                 555                 560

Arg Trp Gln Gln Gly Asn Val Phe Ser Cys Ser Val Met His Glu Ala
                565                 570                 575

Leu His Asn His Tyr Thr Gln Lys Ser Leu Ser Leu Ser Pro Gly Lys
            580                 585                 590


<210> SEQ ID NO 31
<211> LENGTH: 1794
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

gaattcacaa tgggatggtc ttgtatcatc cttttcttgg ttgcaacagc tactggtgtt     60

cattctgagg tccaggtgca acagtctgga cctgaactgg tgacgcctgg ggcctcagtg    120

aagatatcct gcaagacttc tggatacact ttcactgaat ataccgtcca ctgggtgaag    180

cagagccatg gaaagagcct tgagtggatt ggaggcatta atcctaccag tggtggtact    240

aactacaacc agaggttcag gggcaaggcc acattgactg tagacaggtc ctccagcaca    300

gcctacatgg agctccgcag cctgacatct gaggattctg cagtctattt ttgtgcagga    360

accctctatg gctacccttt tgacttctgg ggccaaggca ccactctcac agtctcctca    420

ggttcaactt caggaggagg atcaggtggt ggttcaggag gtggaggatc ttctgacatc    480

ctgatgaccc aatctccatc ctccatgtct gtatctctgg gagactcagt cagcatcact    540

tgccatgcaa gtcagggcat tagcggtaat atagggtggt tgcagcagaa accagggaaa    600

tcatttaagg gcctgatcta tcatggaacc aacttggaag agggagttcc atcaaggttc    660

agtggcagtg gatctggagc agattattct ctcaccatca gcagcctgga gtctgaagat    720

tttgcagact attactgtgt acagtatggt cagtttcctc cgacgttcgg tggaggcacc    780

aagctggaaa tcaaagctag caccaaggga ccttctgttt ttccacttgc tccttcttct    840

aagtctactt ctggtggaac tgctgctttg ggttgtttgg tgaaagatta ctttcctgag    900

ccagtgaccg tttcttggaa ctcaggtgct cttacatctg gtgttcatac tttcccagct    960

gttcttcaat cttcaggact ttactcactt tcttctgttg ttaccgttcc ttcttcaagc   1020

ttgggcactc agacctacat ctgcaatgtg aatcacaaac ccagcaacac caaggttgac   1080

aagaaagttg agcccaagtc ttgtgacaag actcatacgt gtccaccgtg cccagcacct   1140

gaagctgctg gagcaccgtc agtcttcttg tttcctccaa agcctaagga taccttgatg   1200

atctccagga ctcctgaagt cacatgtgta gttgtggatg tgagccatga agatcctgag   1260

gtgaagttca actggtatgt ggatggtgtg gaagtgcaca atgccaagac aaagccgaga   1320

gaggaacagt acaacagcac gtacagggtt gtctcagttc tcactgttct ccatcaagat   1380

tggttgaatg gcaaagagta caagtgcaag gtctccaaca aagccctccc agcccccatt   1440

gagaagacca tttccaaagc gaaagggcaa ccccgtgaac cacaagtgta cacacttcct   1500

ccatctcgcg atgaactgac caagaaccag gtcagcttga cttgcctggt gaaaggcttc   1560

tatccctctg acatagctgt agagtgggag agcaatgggc aaccggagaa caactacaag   1620

actacacctc ccgttctcga ttctgacggc tccttcttcc tctacagcaa gctcacagtg   1680

gacaagagca ggtggcaaca agggaatgtc ttctcatgct ccgtgatgca tgaggctctt   1740
```

-continued

```
cacaatcact acacacagaa gagtctctcc ttgtctccgg gtaaatgagg atcc         1794


<210> SEQ ID NO 32
<211> LENGTH: 592
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Gly Trp Ser Cys Ile Ile Leu Phe Leu Val Ala Thr Ala Thr Gly
1               5                   10                  15

Val His Ser Glu Val Gln Val Gln Gln Ser Gly Pro Glu Leu Val Thr
            20                  25                  30

Pro Gly Ala Ser Val Lys Ile Ser Cys Lys Thr Ser Gly Tyr Thr Phe
        35                  40                  45

Thr Glu Tyr Thr Val His Trp Val Lys Gln Ser His Gly Lys Ser Leu
    50                  55                  60

Glu Trp Ile Gly Gly Ile Asn Pro Thr Ser Gly Gly Thr Asn Tyr Asn
65                  70                  75                  80

Gln Arg Phe Arg Gly Lys Ala Thr Leu Thr Val Asp Arg Ser Ser Ser
                85                  90                  95

Thr Ala Tyr Met Glu Leu Arg Ser Leu Thr Ser Glu Asp Ser Ala Val
            100                 105                 110

Tyr Phe Cys Ala Gly Thr Leu Tyr Gly Tyr Pro Phe Asp Phe Trp Gly
        115                 120                 125

Gln Gly Thr Thr Leu Thr Val Ser Ser Gly Ser Thr Ser Gly Gly Gly
    130                 135                 140

Ser Gly Gly Gly Ser Gly Gly Gly Gly Ser Ser Asp Ile Leu Met Thr
145                 150                 155                 160

Gln Ser Pro Ser Ser Met Ser Val Ser Leu Gly Asp Ser Val Ser Ile
                165                 170                 175

Thr Cys His Ala Ser Gln Gly Ile Ser Gly Asn Ile Gly Trp Leu Gln
            180                 185                 190

Gln Lys Pro Gly Lys Ser Phe Lys Gly Leu Ile Tyr His Gly Thr Asn
        195                 200                 205

Leu Glu Glu Gly Val Pro Ser Arg Phe Ser Gly Ser Gly Ser Gly Ala
    210                 215                 220

Asp Tyr Ser Leu Thr Ile Ser Ser Leu Glu Ser Glu Asp Phe Ala Asp
225                 230                 235                 240

Tyr Tyr Cys Val Gln Tyr Gly Gln Phe Pro Pro Thr Phe Gly Gly Gly
                245                 250                 255

Thr Lys Leu Glu Ile Lys Ala Ser Thr Lys Gly Pro Ser Val Phe Pro
            260                 265                 270

Leu Ala Pro Ser Ser Lys Ser Thr Ser Gly Gly Thr Ala Ala Leu Gly
        275                 280                 285

Cys Leu Val Lys Asp Tyr Phe Pro Glu Pro Val Thr Val Ser Trp Asn
    290                 295                 300

Ser Gly Ala Leu Thr Ser Gly Val His Thr Phe Pro Ala Val Leu Gln
305                 310                 315                 320

Ser Ser Gly Leu Tyr Ser Leu Ser Ser Val Val Thr Val Pro Ser Ser
                325                 330                 335

Ser Leu Gly Thr Gln Thr Tyr Ile Cys Asn Val Asn His Lys Pro Ser
            340                 345                 350
```

```
Asn Thr Lys Val Asp Lys Lys Val Glu Pro Lys Ser Cys Asp Lys Thr
        355                 360                 365

His Thr Cys Pro Pro Cys Pro Ala Pro Glu Ala Ala Gly Ala Pro Ser
    370                 375                 380

Val Phe Leu Phe Pro Pro Lys Pro Lys Asp Thr Leu Met Ile Ser Arg
385                 390                 395                 400

Thr Pro Glu Val Thr Cys Val Val Val Asp Val Ser His Glu Asp Pro
                405                 410                 415

Glu Val Lys Phe Asn Trp Tyr Val Asp Gly Val Glu Val His Asn Ala
            420                 425                 430

Lys Thr Lys Pro Arg Glu Glu Gln Tyr Asn Ser Thr Tyr Arg Val Val
        435                 440                 445

Ser Val Leu Thr Val Leu His Gln Asp Trp Leu Asn Gly Lys Glu Tyr
    450                 455                 460

Lys Cys Lys Val Ser Asn Lys Ala Leu Pro Ala Pro Ile Glu Lys Thr
465                 470                 475                 480

Ile Ser Lys Ala Lys Gly Gln Pro Arg Glu Pro Gln Val Tyr Thr Leu
                485                 490                 495

Pro Pro Ser Arg Asp Glu Leu Thr Lys Asn Gln Val Ser Leu Thr Cys
            500                 505                 510

Leu Val Lys Gly Phe Tyr Pro Ser Asp Ile Ala Val Glu Trp Glu Ser
        515                 520                 525

Asn Gly Gln Pro Glu Asn Asn Tyr Lys Thr Thr Pro Pro Val Leu Asp
    530                 535                 540

Ser Asp Gly Ser Phe Phe Leu Tyr Ser Lys Leu Thr Val Asp Lys Ser
545                 550                 555                 560

Arg Trp Gln Gln Gly Asn Val Phe Ser Cys Ser Val Met His Glu Ala
                565                 570                 575

Leu His Asn His Tyr Thr Gln Lys Ser Leu Ser Leu Ser Pro Gly Lys
            580                 585                 590
```

<210> SEQ ID NO 33
<211> LENGTH: 1422
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33

```
gaattcacaa tgggatggtc ttgtatcatc cttttcttgg ttgcaacagc tactggtgtt     60

cattctcaag ttcaattggt gcagtcaggt gctgaggtga agaaaccagg tgcttcagtt    120

aaggtttctt gtaaggcttc tggttacaca ttcacagatt attggattga atgggtgaga    180

caagctcctg gtcagggtct tgagtggatg ggagatattc tttgtggaac tggaagaact    240

agatacaacg agaaacttaa ggctagagtt actatgactg ctgatacctc tacatctact    300

gcttacatgg aacttagatc tttgagatca gatgacactg ctgtgtacta ttgtgctagg    360

tcagcttctt atggagacta cgctgactat tggggacaag gtactactgt tactgtgtct    420

tctgcttcta ccaagggacc ttctgttttt ccacttgctc cttcttctaa gtctacttct    480

ggtggaactg ctgctttggg ttgtttggtg aaagattact ttcctgagcc agtgaccgtt    540

tcttggaact caggtgctct tacatctggt gttcatactt tcccagctgt tcttcaatct    600

tcaggacttt actcactttc ttctgttgtt accgttcctt cttcaagctt gggcactcag    660
```

```
acctacatct gcaatgtgaa tcacaaaccc agcaacacca aggttgacaa gaaagttgag    720

cccaagtctt gtgacaagac tcatacgtgt ccaccgtgcc cagcacctga acttcttgga    780

ggaccgtcag tcttcttgtt tcctccaaag cctaaggata ccttgatgat ctccaggact    840

cctgaagtca catgtgtagt tgtggatgtg agccatgaag atcctgaggt gaagttcaac    900

tggtatgtgg atggtgtgga agtgcacaat gccaagacaa agccgagaga ggaacagtac    960

aacagcacgt acagggttgt ctcagttctc actgttctcc atcaagattg gttgaatggc   1020

aaagagtaca agtgcaaggt ctccaacaaa gccctcccag cccccattga gaagaccatt   1080

tccaaagcga aagggcaacc ccgtgaacca caagtgtaca cacttcctcc atctcgcgat   1140

gaactgacca agaaccaggt cagcttgact tgcctggtga aaggcttcta tccctctgac   1200

atagctgtag agtgggagag caatgggcaa ccggagaaca actacaagac tacacctccc   1260

gttctcgatt ctgacggctc cttcttcctc tacagcaagc tcacagtgga caagagcagg   1320

tggcaacaag ggaatgtctt ctcatgctcc gtgatgcatg aggctcttca caatcactac   1380

acacagaaga gtctctcctt gtctccgggt aaatgaggat cc                      1422
```

<210> SEQ ID NO 34
<211> LENGTH: 468
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Trp Ile Glu Trp Val Arg Gln Ala Pro Gly Gln Gly Leu
    50                  55                  60

Glu Trp Met Gly Asp Ile Leu Cys Gly Thr Gly Arg Thr Arg Tyr Asn
65                  70                  75                  80

Glu Lys Leu Lys Ala Arg Val Thr Met Thr Ala Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Ser Ala Ser Tyr Gly Asp Tyr Ala Asp Tyr Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220
```

-continued

```
His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465
```

<210> SEQ ID NO 35
<211> LENGTH: 1422
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 35

```
gaattcacaa tgggatggtc ttgtatcatc cttttcttgg ttgcaacagc tactggtgtt      60

cattctcaag ttcaattggt gcagtcaggt gctgaggtga agaaaccagg tgcttcagtt     120

aaggtttctt gtaaggcttc tggttacaca ttcacagatt attggattga atgggtgaga     180

caagctcctg gtcagggtct tgagtggatg ggagatattc tttgtggaac tggaagaact     240

agatacaacg agaaacttaa ggctagagtt actatgactg ctgatacctc tacatctact     300

gcttacatgg aacttagatc tttgagatca gatgacactg ctgtgtacta ttgtgctagg     360

tcagcttctt atggagacta cgctgactat tggggacaag gtactactgt tactgtgtct     420

tctgcttcta ccaagggacc ttctgttttt ccacttgctc cttcttctaa gtctacttct     480

ggtggaactg ctgctttggg ttgtttggtg aaagattact ttcctgagcc agtgaccgtt     540

tcttggaact caggtgctct tacatctggt gttcatactt tcccagctgt tcttcaatct     600
```

```
tcaggacttt actcactttc ttctgttgtt accgttcctt cttcaagctt gggcactcag    660

acctacatct gcaatgtgaa tcacaaaccc agcaacacca aggttgacaa gaaagttgag    720

cccaagtctt gtgacaagac tcatacgtgt ccaccgtgcc cagcacctga acttcttgga    780

ggaccgtcag tcttcttgtt tcctccaaag cctaaggata ccttgatgat ctccaggact    840

cctgaagtca catgtgtagt tgtggatgtg agccatgaag atcctgaggt gaagttcaac    900

tggtatgtgg atggtgtgga agtgcacaat gccaagacaa agccgagaga ggaacagtac    960

caaagcacgt acagggttgt ctcagttctc actgttctcc atcaagattg gttgaatggc   1020

aaagagtaca agtgcaaggt ctccaacaaa gccctcccag cccccattga gaagaccatt   1080

tccaaagcga aagggcaacc ccgtgaacca caagtgtaca cacttcctcc atctcgcgat   1140

gaactgacca agaaccaggt cagcttgact tgcctggtga aaggcttcta tccctctgac   1200

atagctgtag agtgggagag caatgggcaa ccggagaaca actacaagac tacacctccc   1260

gttctcgatt ctgacggctc cttcttcctc tacagcaagc tcacagtgga caagagcagg   1320

tggcaacaag ggaatgtctt ctcatgctcc gtgatgcatg aggctcttca caatcactac   1380

acacagaaga gtctctcctt gtctccgggt aaatgaggat cc                      1422
```

<210> SEQ ID NO 36
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Trp Ile Glu Trp Val Arg Gln Ala Pro Gly Gln Gly Leu
    50                  55                  60

Glu Trp Met Gly Asp Ile Leu Cys Gly Thr Gly Arg Thr Arg Tyr Asn
65                  70                  75                  80

Glu Lys Leu Lys Ala Arg Val Thr Met Thr Ala Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Ser Ala Ser Tyr Gly Asp Tyr Ala Asp Tyr Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
```

-continued

```
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Gln Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465


<210> SEQ ID NO 37
<211> LENGTH: 1422
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

gaattcacaa tgggatggtc ttgtatcatc cttttcttgg ttgcaacagc tactggtgtt     60

cattctcaag ttcaattggt gcagtcaggt gctgaggtga agaaaccagg tgcttcagtt    120

aaggtttctt gtaaggcttc tggttacaca ttcacagatt attggattga atgggtgaga    180

caagctcctg gtcagggtct tgagtggatg ggagatattc tttgtggaac tggaagaact    240

agatacaacg agaaacttaa ggctagagtt actatgactg ctgatacctc tacatctact    300

gcttacatgg aacttagatc tttgagatca gatgacactg ctgtgtacta ttgtgctagg    360

tcagcttctt atggagacta cgctgactat tggggacaag gtactactgt tactgtgtct    420

tctgcttcta ccaagggacc ttctgttttt ccacttgctc cttcttctaa gtctacttct    480

ggtggaactg ctgctttggg ttgtttggtg aaagattact ttcctgagcc agtgaccgtt    540
```

-continued

```
tcttggaact caggtgctct tacatctggt gttcatactt tcccagctgt tcttcaatct    600

tcaggacttt actcactttc ttctgttgtt accgttcctt cttcaagctt gggcactcag    660

acctacatct gcaatgtgaa tcacaaaccc agcaacacca aggttgacaa gaaagttgag    720

cccaagtctt gtgacaagac tcatacgtgt ccaccgtgcc cagcacctga agctgctgga    780

ggaccgtcag tcttcttgtt tcctccaaag cctaaggata ccttgatgat ctccaggact    840

cctgaagtca catgtgtagt tgtggatgtg agccatgaag atcctgaggt gaagttcaac    900

tggtatgtgg atggtgtgga agtgcacaat gccaagacaa agccgagaga ggaacagtac    960

aacagcacgt acagggttgt ctcagttctc actgttctcc atcaagattg gttgaatggc   1020

aaagagtaca agtgcaaggt ctccaacaaa gccctcccag cccccattga gaagaccatt   1080

tccaaagcga aagggcaacc ccgtgaacca caagtgtaca cacttcctcc atctcgcgat   1140

gaactgacca agaaccaggt cagcttgact tgcctggtga aaggcttcta tccctctgac   1200

atagctgtag agtgggagag caatgggcaa ccggagaaca actacaagac tacacctccc   1260

gttctcgatt ctgacggctc cttcttcctc tacagcaagc tcacagtgga caagagcagg   1320

tggcaacaag ggaatgtctt ctcatgctcc gtgatgcatg aggctcttca caatcactac   1380

acacagaaga gtctctcctt gtctccgggt aaatgaggat cc                      1422


<210> SEQ ID NO 38
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Trp Ile Glu Trp Val Arg Gln Ala Pro Gly Gln Gly Leu
    50                  55                  60

Glu Trp Met Gly Asp Ile Leu Cys Gly Thr Gly Arg Thr Arg Tyr Asn
65                  70                  75                  80

Glu Lys Leu Lys Ala Arg Val Thr Met Thr Ala Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Ser Ala Ser Tyr Gly Asp Tyr Ala Asp Tyr Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205
```

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Ala Ala
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 39
<211> LENGTH: 1422
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gaattcacaa tgggatggtc ttgtatcatc cttttcttgg ttgcaacagc tactggtgtt      60
cattctcaag ttcaattggt gcagtcaggt gctgaggtga agaaaccagg tgcttcagtt     120
aaggtttctt gtaaggcttc tggttacaca ttcacagatt attggattga atgggtgaga     180
caagctcctg gtcagggtct tgagtggatg ggagatattc tttgtggaac tggaagaact     240
agatacaacg agaaacttaa ggctagagtt actatgactg ctgatacctc tacatctact     300
gcttacatgg aacttagatc tttgagatca gatgacactg ctgtgtacta ttgtgctagg     360
tcagcttctt atggagacta cgctgactat tggggacaag gtactactgt tactgtgtct     420
tctgcttcta ccaagggacc ttctgttttt ccacttgctc cttcttctaa gtctacttct     480

```
ggtggaactg ctgctttggg ttgtttggtg aaagattact ttcctgagcc agtgaccgtt    540

tcttggaact caggtgctct tacatctggt gttcatactt tcccagctgt tcttcaatct    600

tcaggacttt actcactttc ttctgttgtt accgttcctt cttcaagctt gggcactcag    660

acctacatct gcaatgtgaa tcacaaaccc agcaacacca aggttgacaa gaaagttgag    720

cccaagtctt gtgacaagac tcatacgtgt ccaccgtgcc cagcacctga agctgctgga    780

gcaccgtcag tcttcttgtt tcctccaaag cctaaggata ccttgatgat ctccaggact    840

cctgaagtca catgtgtagt tgtggatgtg agccatgaag atcctgaggt gaagttcaac    900

tggtatgtgg atggtgtgga agtgcacaat gccaagacaa agccgagaga ggaacagtac    960

aacagcacgt acagggttgt ctcagttctc actgttctcc atcaagattg gttgaatggc   1020

aaagagtaca agtgcaaggt ctccaacaaa gccctcccag cccccattga gaagaccatt   1080

tccaaagcga aagggcaacc ccgtgaacca caagtgtaca cacttcctcc atctcgcgat   1140

gaactgacca agaaccaggt cagcttgact tgcctggtga aaggcttcta tccctctgac   1200

atagctgtag agtgggagag caatgggcaa ccggagaaca actacaagac tacacctccc   1260

gttctcgatt ctgacggctc cttcttcctc tacagcaagc tcacagtgga caagagcagg   1320

tggcaacaag ggaatgtctt ctcatgctcc gtgatgcatg aggctcttca caatcactac   1380

acacagaaga gtctctcctt gtctccgggt aaatgaggat cc                      1422
```

<210> SEQ ID NO 40
<211> LENGTH: 468
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Trp Ile Glu Trp Val Arg Gln Ala Pro Gly Gln Gly Leu
    50                  55                  60

Glu Trp Met Gly Asp Ile Leu Cys Gly Thr Gly Arg Thr Arg Tyr Asn
65                  70                  75                  80

Glu Lys Leu Lys Ala Arg Val Thr Met Thr Ala Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Ser Ala Ser Tyr Gly Asp Tyr Ala Asp Tyr Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190
```

```
Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Ala Ala
                245                 250                 255

Gly Ala Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465


<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Met Gly Trp Ser Cys Ile Ile Leu Phe Leu Val Ala Thr Ala Thr Gly
1               5                   10                  15

Val His Ser
```